(12) United States Patent
Conner

(10) Patent No.: US 10,813,958 B2
(45) Date of Patent: *Oct. 27, 2020

(54) USE OF ONCOLYTIC HERPES SIMPLEX VIRUS, ALONE OR IN COMBINATION WITH IMMUNE CHECK-POINT INHIBITOR, IN THE TREATMENT OF CANCER

(71) Applicant: VIRTTU BIOLOGICS LIMITED, Newhouse (GB)

(72) Inventor: Joe Conner, Newhouse (GB)

(73) Assignee: Virttu Biologics Limited, Newhouse (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,757

(22) Filed: Jan. 19, 2018

(65) Prior Publication Data

US 2018/0207212 A1   Jul. 26, 2018

Related U.S. Application Data

(63) Continuation of application No. PCT/GB2016/052175, filed on Jul. 19, 2016.

(30) Foreign Application Priority Data

Jul. 20, 2015 (GB) .................................... 1512723.6
Dec. 30, 2015 (GB) .................................... 1523091.5

(51) Int. Cl.
| | |
|---|---|
| *A61K 35/763* | (2015.01) |
| *A61K 39/395* | (2006.01) |
| *C07K 16/28* | (2006.01) |
| *A61K 45/06* | (2006.01) |
| *A61K 47/12* | (2006.01) |
| *A61K 9/00* | (2006.01) |
| *A61K 35/768* | (2015.01) |
| *A61K 9/08* | (2006.01) |
| *A61P 35/00* | (2006.01) |
| *A61K 39/00* | (2006.01) |

(52) U.S. Cl.
CPC .......... *A61K 35/763* (2013.01); *A61K 9/0019* (2013.01); *A61K 9/08* (2013.01); *A61K 35/768* (2013.01); *A61K 39/3955* (2013.01); *A61K 39/39566* (2013.01); *A61K 45/06* (2013.01); *A61K 47/12* (2013.01); *A61P 35/00* (2018.01); *C07K 16/2818* (2013.01); *A61K 2039/505* (2013.01); *A61K 2039/57* (2013.01); *C07K 2317/73* (2013.01); *C07K 2317/76* (2013.01)

(58) Field of Classification Search
CPC ...... A61K 35/763; A61K 45/06; A61K 47/12; A61K 9/0019; A61K 35/768; A61K 9/08; A61K 39/3955; A61K 39/39566; A61K 2039/57; A61K 2039/505; C07K 16/2818; C07K 2317/73; C07K 2317/76; A61P 35/00

See application file for complete search history.

(56) References Cited

U.S. PATENT DOCUMENTS

| | | |
|---|---|---|
| 9,410,139 B2 | 8/2016 | Dadaglio et al. |
| 2010/0297072 A1 | 11/2010 | DePinho |

FOREIGN PATENT DOCUMENTS

| | | | | |
|---|---|---|---|---|
| EP | 1003533 A1 | 5/2000 | | |
| WO | 2007/052029 A1 | 5/2007 | | |
| WO | WO-2012135641 A2 | * | 10/2012 | ........... C07D 239/48 |
| WO | 2013/112942 A1 | 8/2013 | | |
| WO | WO-2013167909 A1 | * | 11/2013 | ........... A61K 31/704 |
| WO | 2014/022138 A2 | 2/2014 | | |
| WO | 2014/036412 A2 | 3/2014 | | |
| WO | 2014/047350 A1 | 3/2014 | | |
| WO | WO-2014138314 A1 | * | 9/2014 | ......... A61K 38/1764 |
| WO | WO-2016009017 A1 | * | 1/2016 | ........... A61K 35/768 |
| WO | 2016/100364 A1 | 6/2016 | | |
| WO | WO-2016100364 A1 | * | 6/2016 | ........... A61K 35/763 |
| WO | WO-2017106656 A1 | * | 6/2017 | ....... A61K 39/39558 |

OTHER PUBLICATIONS

Jin H, Yan Z, Ma Y, Cao Y, He B. A herpesvirus virulence factor inhibits dendritic cell maturation through protein phosphatase 1 and Ikappa B kinase. J Virol. Apr. 2011;85(7):3397-407. Epub Jan. 19, 2011.*

Stiles KM, Whitbeck JC, Lou H, Cohen GH, Eisenberg RJ, Krummenacher C. Herpes simplex virus glycoprotein D interferes with binding of herpesvirus entry mediator to its ligands through downregulation and direct competition. J Virol. Nov. 2010;84(22):11646-60. Epub Sep. 8, 2010.*

Kitano S, Tsuji T, Liu C, Hirschhorn-Cymerman D, Kyi C, Mu Z, Allison JP, Gnjatic S, Yuan JD, Wolchok JD. Enhancement of tumor-reactive cytotoxic CD4+ T cell responses after ipilimumab treatment in four advanced melanoma patients. Cancer Immunol Res. Oct. 2013;1(4):235-44.*

ClinicalTrials.gov Study: NCT01740297: Ipilimumab With or Without Talimogene Laherparepvec in Unresected Melanoma. Ver. 23, updated Jul. 15, 2015, Sponsored by Amgen.*

Braidwood L, Graham SV, Graham A, Conner J. Oncolytic herpes viruses, chemotherapeutics, and other cancer drugs. Oncolytic Virother. Dec. 4, 2013;2:57-74.*

De Vicente JC, Rodríguez-Santamarta T, Rodrigo JP, Blanco-Lorenzo V, Allonca E, García-Pedrero JM. PD-L1 Expression in Tumor Cells Is an Independent Unfavorable Prognostic Factor in Oral Squamous Cell Carcinoma. Cancer Epidemiol Biomarkers Prev. Mar. 2019;28(3):546-554. Epub Nov. 28, 2018.*

Conner J, Braidwood L. Expression of inhibitor of growth 4 by HSV1716 improves oncolytic potency and enhances efficacy. Cancer Gene Ther. Jul. 2012;19(7):499-507. Epub May 18, 2012.*

(Continued)

*Primary Examiner* — Rachel B Gill

(74) *Attorney, Agent, or Firm* — McNeill Baur PLLC

(57) ABSTRACT

An oncolytic herpes simplex virus is disclosed for use in a method of treating cancer, the method comprising administering one or more doses of an oncolytic herpes simplex virus effective to induce a Th1 immune response in the subject, and optionally administering a therapeutically effective amount of an immune checkpoint inhibitor.

10 Claims, 64 Drawing Sheets

(56) References Cited

OTHER PUBLICATIONS

Braidwood L, Dunn PD, Hardy S, Evans TR, Brown SM. Antitumor activity of a selectively replication competent herpes simplex virus (HSV) with enzyme prodrug therapy. Anticancer Res. Jun. 2009;29(6):2159-66.*
Quigg M, Mairs RJ, Brown SM, Harland J, Dunn P, Rampling R, Livingstone A, Wilson L, Boyd M. Assessment in vitro of a novel therapeutic strategy for glioma, combining herpes simplex virus HSV1716-mediated oncolysis with gene transfer and targeted radiotherapy. Med Chem. Sep. 2005;1(5):423-9.*
Tufaro F, Marked JM. Herpesviruses as therapeutic agents. In: Arvin A, Campadelli-Fiume G, Mocarski E, et al., editors. Human Herpesviruses: Biology, Therapy, and Immunoprophylaxis. Cambridge: Cambridge University Press; 2007. Chapter 76. Available from: https://www.ncbi.nlm.nih.gov/books/NBK47378/.*
Adam C Drake, Of mice and men: what rodent models don't tell us. Cellular & Molecular Immunology. 10, 284-285 (2013).
Allen et al., Anti-tumour immunity in head and neck cancer. Cancers, vol. 7, 2397-2414 (2016).
Benencia et al, HSV Oncolytic Therapy Upregulates Interferon-Inducible Chemokines and Recruits Immune Effector Cells in Ovarian Cancer. Molecular Therapy vol. 12, No. 5, (Nov. 2005).
Benencia et al., Herpes virus oncolytic therapy reverses tumor immune dysfunction and facilitates tumor antigen presentation. Cancer Biology & Therapy 7:8, 1194-1205 (2008).
Braidwood et al., Potent efficacy signals from systemically administered oncolytic herpes simplex virus (HSV1716) in hepatocellular carcinoma xenograft models. Journal of Hepatocellular Carcinoma,1 149-161(2014).
Breitbach et al, Intravenous delivery of a multi-mechanistic cancer-targeted oncolytic poxvirus in humans. vol. 477, Nature (Sep. 2011).
Cripe et al., A phase I dose escalation study of intratumoural or intravenous herpes simplex virus-1 mutant HSV1716 in pediatric/young adult patients with refractory non-central nervous system solid tumors. XP002761994, 8th Int'l Conf. on Oncolytic Virus Therapeutics (Apr. 2014).
Cripe et al., HSV1716 (Seprehvir); NIH RAC Presentation (Jun. 2013).
Cripe et al., Pediatric cancer gone viral. Part I: strategies for utilizing oncolytic herpes simple virus-1 in children. Mol Ther Oncolytics. 2 (2015).
Cripe et al., Pediatric cancer gone viral. Part II: potential clinical application of oncolytic herpes simplex virus-1 in children. Mol Ther Oncolytics. 2 (2015).
Dipongkor et al Immunovirotherapy Combined with Immune Checkpoint Inhibitors for Treating Glioblastoma; Molecular Therapy, vol. 23 Suppl. 1, p. S248, #624 (May 2015.).
Gadhikar et al., Chk1/2 inhibition overcomes the cisplatin resistance of head and neck cancer cells secondary to the loss of cuntional p53. Mol. Cancer. Ther., vol. 12, pp. 1860-1873, (2013).
Giraldo et al., The immune contexture of primary and metastatic human tumours. Current Opinion in Immunology 27:8-15, (2014).
Haabeth, Inflammation driven by tumour-specific Th1 cells protects against B-cell cancer. Nature Communications, (dated 2010 published 2011).

Johnson, et al., Talimogene laherparepvec (T-VEC) for the treatment of advanced melanoma. Immunotherapy 76, 611-619 (2015).
Kim, Subverting the adaptive immune resistance mechanism to improve clinical responses to immune checkpoint blockade therapy. OncoImmunology, 3:12, e954868 (Dec. 2014).
L. Aurelian, Herpes Simplex Virus Type 2 Vaccines: New Ground for Optimism? Clinical and Diagnostic Laboratory Immunology, p. 437-445, (May 2004).
Learmouth et al., Neutralisation effects of pleural fluids do not predict the persistence of the oncolytic HSV Seprehvir following intrapleural administration in patients with malignant pleural mesothelioma. Virrtu Biologics.
Li et al, Virotherapy with a Type 2 Herpes Simplex Virys-Derived Oncolytic Virus Induces Potent Antitumor Immunity Against Neuroblastoma. Clin Cancer Res. 2007; 13(1) Jan. 1, 2007.
Liu et al ICP34.5 deleted herpes simplex virus with enhanced oncolytic immune stimulating, and anti-tumour properties. Gene Therapy (2003), 10, 292-303.
Mace et al., Potential for efficacy of the oncolytic herpes simple virus 1716 in patients with oral squamous cell carcinoma. Head & Neck, (Jan. 2008).
Melchjorsen et al., Activation and Evasion of Innate Antiviral Immunity by Herpes Simplex Virus. Viruses 1, 737-759 (2009).
Mestas and Hughes, of Mice and Not Men: Differences between Mouse and Human Immunology. The Journal of Immunology, 172:2731-2738 (2004).
Miller et al., Requirement of an integrated immune response for successful neuroattenuated HSV-1 therapy in an intracranial metastatic melanoma model. Mol Ther 7(6) 741-747 (Jun. 2013).
Nakano et al, Interleukin 6 and its relationship to clinical parameters in patients with malignant pleural mesothelioma. British Journal of Cancer 77 (6), 907-912 (1998).
NCT02263508 Pembrolizumab (MK-3475) With or Without Talimogene Laherparepvec in Unresected melanoma. Clinical Trials.gov Archives, (Jun. 2015).
NCT02272855 A study of Combination Treatment with HF10 and Ipilimumab in Patients with Unresectable or Metastatic Melanoma. Clinical Trials.gov Archives, (Apr. 2015).
Pardoll, The blockade of immune checkpoints in cancer immunotherapy, www.nature.com/reviews/cancer, vol. 12 (Apr. 2012).
Prestwich et al., Oncolytic viruses: a novel form of immunotherapy. Expert Rev Anticancer Ther. 8 (10): 1581-1588, (Oct. 2008).
Rahim et al. The role of interleukin-6 in malignant mesothelioma. Transl Lung Cancer Res. 4(1):55-66 (2015).
Russell et al, Oncolytic virtherapy. Nature Biotechnology: vol. 30, No. 7 (Jul. 2012).
Sagiv-Barfi et al., Therapeutic antitumor immunity by checkpoint blockade is enhanced by ibrutinib, an inhibitor of both BTK and ITK. PNAS, Published on-line, (Feb. 2015).
Seymour and Fisher, Oncolytic viruses: finally delivering. British Journal of Cancer: 114, 357-361 (2016).
Wang et al., Oncolytic herpes simplex virus treatment of metastatic breast cancer. International Journal of Oncology 40: 757-763 (2012).
Eissa, et al. "Genomic Signature of the Natural Oncolytic Herpes Simplex Virus HF10 and Its Therapeutic Role in Preclinical and Clinical Trials," Frontiers in Oncology, 7(149): 1-12 (2017).

* cited by examiner

| Patient | No. doses | Th1 response | | | | | | Pro-inflammatory | | Th2 response | | | | |
|---|---|---|---|---|---|---|---|---|---|---|---|---|---|---|
| | | IL-2 | IL-12 | IFN-γ | IP-10 | MIG | TNF-α | IL-6 | IL-1α | IL-4 | IL-10 | IFN-α | VEGF | IL-21 |
| 01 | 1 | → | - | ++ | +++ | +++ | ++ | + | - | - | + | - | → | - |
| 02 | 1 | → | → | - | → | - | +/→ | → | + | - | + | - | +++ | + |
| 03 | 1 | → | ++ | ++ | +++ | +++ | + | + | - | - | -/→ | - | +++ | → |
| 04 | 2 | → | - | +++++ | +++ | +++++ | +++ | + | - | - | + | - | → | - |
| 05 | 2 | → | - | - | - | - | → | → | - | - | -/→ | - | ++ | + |
| 06* | 2 | | | | | | | | | | | | | |
| 07 | 4 | ++ | +++ | +++++ | ++++ | +++ | + | + | - | - | ++ | - | - | → |
| 08 | 4 | ++ | ++ | +++++ | +++ | +++ | + | +++ | - | → | +++ | + | → | + |
| 09 | 4 | ++ | ++ | ++ | +++ | +++ | tba | + | tba | +++ | + | tba | +++ | + |

Fig. 1

| IFN-γ | | | |
|---|---|---|---|
| Patient | No. of doses | Level at baseline | Response |
| 01 | 1 | <0.5pg/ml | + |
| 02 | | <0.5pg/ml | - |
| 03 | | <0.5pg/ml | ++ |
| 04 | 2 | <0.5pg/ml | +++++ |
| 05 | | 1pg/ml | - |
| 06 | | No samples | tba |
| 07 | 4 | <0.5pg/ml | ++++ |
| 08 | | <0.5pg/ml | ++++ |
| 09 | | <0.5pg/ml | ++ |

Fig. 2

| IFN-α ||||
|---|---|---|---|
| Patient | No. of doses | Level at baseline | Response |
| 01 | 1 | <50pg/ml | - |
| 02 | | <10pg/ml | - |
| 03 | | <50pg/ml | - |
| 04 | 2 | <50pg/ml | - |
| 05 | | <50pg/ml | - |
| 06 | | No samples | |
| 07 | 4 | <50pg/ml | - |
| 08 | | <50pg/ml | + |
| 09 | | tba | |

Fig. 3

| IL-1α | | | |
|---|---|---|---|
| Patient | No. of doses | Level at baseline | Response |
| 01 | 1 | <3.9pg/ml | - |
| 02 | | 5pg/ml | + |
| 03 | | <3.9pg/ml | - |
| 04 | 2 | <3.9pg/ml | - |
| 05 | | <3.9pg/ml | - |
| 06 | | No samples | |
| 07 | 4 | <3.9pg/ml | - |
| 08 | | <3.9pg/ml | - |
| 09 | | tba | |

Fig. 4

| IL-2 |||| 
|---|---|---|---|
| Patient | No. of doses | Level at baseline | Response |
| 01 | 1 | 876pg/ml | - |
| 02 | | 461pg/ml | - |
| 03 | | 463pg/ml | - |
| 04 | 2 | 481pg/ml | - |
| 05 | | 587pg/ml | - |
| 06 | | No samples | |
| 07 | 4 | 387pg/ml | ++ |
| 08 | | 441pg/ml | ++ |
| 09 | | 327pg/ml | ++ |

Fig. 5

| IL-4 |||| 
|---|---|---|---|
| Patient | No. of doses | Level at baseline | Response |
| 01 | 1 | 0pg/ml | - |
| 02 | | 0pg/ml | - |
| 03 | | 0pg/ml | - |
| 04 | 2 | 0pg/ml | - |
| 05 | | 0pg/ml | - |
| 06 | | No samples | |
| 07 | 4 | 0pg/ml | - |
| 08 | | 0pg/ml | + |
| 09 | | tba | |

Fig. 6

| IL-6 ||||
|---|---|---|---|
| Patient | No. of doses | Level at baseline | Response |
| 01 | 1 | 187ng/ml | + |
| 02 |  | 340ng/ml | - |
| 03 |  | 55ng/ml | + |
| 04 | 2 | 89ng/ml | + |
| 05 |  | 193ng/ml | - |
| 06 |  | No samples |  |
| 07 | 4 | 53ng/ml | + |
| 08 |  | 60ng/ml | +++ |
| 09 |  | 59ng/ml | + |

Fig. 7

| IL-10 | | | |
|---|---|---|---|
| Patient | No. of doses | Level at baseline | Response |
| 01 | 1 | 18pg/ml | + |
| 02 | | 17pg/ml | + |
| 03 | | 21pg/ml | - |
| 04 | 2 | 21pg/ml | + |
| 05 | | 26pg/ml | - |
| 06 | | No samples | |
| 07 | 4 | 30pg/ml | ++ |
| 08 | | 40pg/ml | +++ |
| 09 | | 17pg/ml | + |

Fig. 8

| IL-12 | | | |
|---|---|---|---|
| Patient | No. of doses | Level at baseline | Response |
| 01 | 1 | 108pg/ml | - |
| 02 | | 136pg/ml | ↓ |
| 03 | | 297pg/ml | ++ |
| 04 | 2 | 330pg/ml | - |
| 05 | | 61pg/ml | - |
| 06 | | No samples | |
| 07 | 4 | 126pg/ml | +++ |
| 08 | | 165pg/ml | ++ |
| 09 | | 60pg/ml | ++ |

Fig. 9

| IL-21 | | | |
|---|---|---|---|
| Patient | No. of doses | Level at baseline | Response |
| 01 | 1 | 188pg/ml | - |
| 02 | | 187pg/ml | + |
| 03 | | 220pg/ml | ↓ |
| 04 | 2 | 242pg/ml | - |
| 05 | | 204pg/ml | + |
| 06 | | No samples | |
| 07 | 4 | 462pg/ml | ↓ |
| 08 | | 211pg/ml | + |
| 09 | | 334pg/ml | + |

Fig. 10

| TNF-α | | | |
|---|---|---|---|
| Patient | No. of doses | Level at baseline | Response |
| 01 | 1 | <0.5pg/ml | + |
| 02 | | 4pg/ml | +/- |
| 03 | | 2.5pg/ml | + |
| 04 | 2 | 3pg/ml | +++ |
| 05 | | <0.5pg/ml | - |
| 06 | | No samples | |
| 07 | 4 | <0.5pg/ml | + |
| 08 | | <0.5pg/ml | + |
| 09 | | tba | |

Fig. 11

| IP-10 | | | |
|---|---|---|---|
| Patient | No. of doses | Level at baseline | Response |
| 01 | 1 | 222pg/ml | +++ |
| 02 | | 182pg/ml | - |
| 03 | | 11,903pg/ml | +++ |
| 04 | 2 | 237pg/ml | +++ |
| 05 | | 371pg/ml | - |
| 06 | | No samples | |
| 07 | 4 | 5149pg/ml | ++++ |
| 08 | | 49pg/ml | +++ |
| 09 | | 24.2pg/ml | +++ |

Fig. 12

| MIG ||||
|---------|-------------|------------------|----------|
| Patient | No. of doses | Level at baseline | Response |
| 01 | 1 | 21,572pg/ml | +++ |
| 02 | | 25,141pg/ml | - |
| 03 | | 47,219pg/ml | +++ |
| 04 | 2 | 34,449pg/ml | ++++ |
| 05 | | 31,083pg/ml | - |
| 06 | | No samples | |
| 07 | 4 | 46,667pg/ml | +++ |
| 08 | | 29,791pg/ml | +++ |
| 09 | | 30,844pg/ml | ++++ |

Fig. 13

| VEGF | | | |
|---|---|---|---|
| Patient | No. of doses | Level at baseline | Response |
| 01 | 1 | 1660pg/ml | - |
| 02 | | 2500pg/ml | +++ |
| 03 | | 330pg/ml | +++ |
| 04 | 2 | 1070pg/ml | - |
| 05 | | 2000pg/ml | ++ |
| 06 | | No samples | |
| 07 | 4 | 210pg/ml | - |
| 08 | | 1060pg/ml | - |
| 09 | | 75pg/ml | +++ |

Fig. 14

| Cytokine Th1 response versus patient survival | | | | |
|---|---|---|---|---|
| | | Survival ≥1 yr | | Survival <1yr |
| | | Th1 response | No Th1 response | Th1 response | No Th1 response |
| Data at 20 July 2015 | No of patients* | 4 (mean =16.75 mths) | 1 (13 mths) | 1 (10 mths) | 1 (4 mths) |
| Data at 25 May 2016 | No of patients# | 6** (median = 19 months) | 1 (13 mths) | 1*** (10 mths) | 2 (4 mths) |

Fig. 19

| High (ng/ml) | Low (pg/ml) | undetected |
|---|---|---|
| IL-6, IL-8, IL-27, CXCL9 (MIG), VEGF | IL-2, IL-10, IL-12, IL-21, CXCL10 (IP10), CXCL11 (I-TAC) | IFNγ, IFNα, IL-1α, IL-4, TNFα, GM-CSF |

Fig. 20

| doses | IFNγ | IP10 | MIG | I-TAC | VEGF | TNFα | IL2 | IL6 | IL8 | IL10 | IL12 |
|---|---|---|---|---|---|---|---|---|---|---|---|
| Pt 01 | ++ | +++ | +++ | +++ | → | +++ | → | + | + | + | - |
| Pt 02  1 | - | → | - | - | +++ | → | → | → | → | + | → |
| Pt 03 | +++ | +++ | +++ | +++ | +++ | +++ | → | + | + | -/↓ | +++ |
| Pt 04 | +++++ | +++ | +++ | +++ | → | +++ | → | + | → | + | ++ |
| Pt 05  2 | - | - | - | + | ++ | → | → | → | - | -/↓ | - |
| Pt 06 | - | +++ | +++ | nd | ++ | - | - | → | - | - | - |
| Pt 07 | +++++ | +++ | +++ | +++ | - | +++ | +++ | + | +++ | +++ | +++ |
| Pt 08  4 | + | +++ | +++ | +++ | → | ++ | +++ | +++ | +++ | +++ | ++ |
| Pt 09 | + | +++ | +++ | +++ | +++ | - | +++ | + | +++ | + | + |

= cytokine/chemokine associated with aTh1 response   - = unchanged, + = weak to +++++ = strong response,
↓ = decrease, nd = not done

Fig. 23

| Doses | | IFNα | IL1α | IL4 | IL21 | IL27 | GM-CSF |
|---|---|---|---|---|---|---|---|
| Pt 01 | | - | - | - | - | ↓ | - |
| Pt 02 | 1 | - | + | - | + | ↓ | - |
| Pt 03 | | - | - | - | ↓ | ↓ | - |
| Pt 04 | | - | - | - | - | - | - |
| Pt 05 | 2 | ++ | - | - | + | + | - |
| Pt 06 | | + | - | nd | nd | nd | - |
| Pt 07 | 4 | + | - | - | ↓ | ++ | - |
| Pt 08 | | - | + | + | + | - | - |
| Pt 09 | | - | - | - | + | - | - | nd = not done, + = increase, - = unchanged, ↓ = decrease

Fig. 24

| Pt no | No of doses | status | HSV DNA in pleural fluids | Pleural fluid Th1 response |
|---|---|---|---|---|
| 01001 | | seropositive | - | +++ |
| 01002 | 1 | seropositive | +++++ | - |
| 01003 | | seropositive | - | ++ |
| 01004 | | seropositive | - | ++++ |
| 01005 | 2 | seropositive | + | - |
| 01006 | | seropositive | +++ | ++ |
| 01007 | | seropositive | +++ | +++ |
| 01008 | 4 | seronegative | ++++ | +++++ |
| 01009 | | seropositive | + | ++ |

- = unchanged, + = weak to +++++ = strong response

Fig. 25

| | Doses | HSV DNA in pleural fluid | Pleural Fluid Th1 | Immune cells | Granzyme B |
|---|---|---|---|---|---|
| Pt 01 | 1 | - | +++ | nd | +++ |
| Pt 02 | 1 | +++++ | - | nd | - |
| Pt 03 | 1 | - | ++ | nd | +++ |
| Pt 04 | 2 | - | ++++ | ++ | +++ |
| Pt 05 | 2 | + | - | ↓ | - |
| Pt 06 | 2 | +++ | ++ | nd | ++++ |
| Pt 07 | 4 | +++ | +++ | +++ | ++++ |
| Pt 08 | 4 | ++++ | +++++ | +++ | ++ |
| Pt 09 | 4 | + | ++ | ++ | + |

Fig. 56

- = unchanged, + = weak to +++++ = strong response, ↓ = decrease, nd = not determined

| Patient no. | No. of doses | Pleural fluid Th1 response | Novel anti-tumour IgG response |
|---|---|---|---|
| 01001 | 1 | +++ | - |
| 01002 | 1 | - | - |
| 01903 | 1 | ++ | - |
| 01004 | 2 | ++++ | +++ |
| 01005 | 2 | - | - |
| 01006 | 2 | ++ | ++ |
| 01007 | 4 | +++ | +++ |
| 01008 | 4 | +++++ | ++ |
| 01009 | 4 | ++ | + |

Fig. 57

| Time | Patient HSV06 | Patient HSV09 | Patient HSV10 |
|---|---|---|---|
| Baseline | Neg | Neg | Neg |
| Day 0 Pre Infusion | Neg | Neg | Neg |
| Day 0 Post Infusion | | | |
| 3 hours | Neg | Neg | Neg |
| 6 hours | Neg | Neg | Neg |
| 18 hours | Neg | Neg | Neg |
| 24 hours | Neg | Neg | Neg |
| Day 4 | Pos | Pos | Neg |
| Day 7 | Pos | Neg | Neg |
| Day 14 | Pos | Neg | Neg |

Fig. 58

| | HSV06 | HSV09 | HSV10 | HSV13 | HSV07 | HSV08 | HSV11 | HSV12 |
|---|---|---|---|---|---|---|---|---|
| Route of administration | IV | IV | IV | IV | ITu | ITu | ITu | ITu |
| Baseline | neg | neg | neg | neg | neg | neg | neg | neg |
| Day +1 | neg | neg | neg | neg | neg | neg | neg | neg |
| Day +4 | Pos | Pos | neg | neg | Pos | Pos | Pos | Pos |
| Day +7 | Pos | neg | neg | neg | neg | nd | Pos | Pos |
| Day +14 | Pos | neg | nd | neg | neg | nd | neg | nd |
| Day +28 | | | | Pos | | | | |

Fig. 59

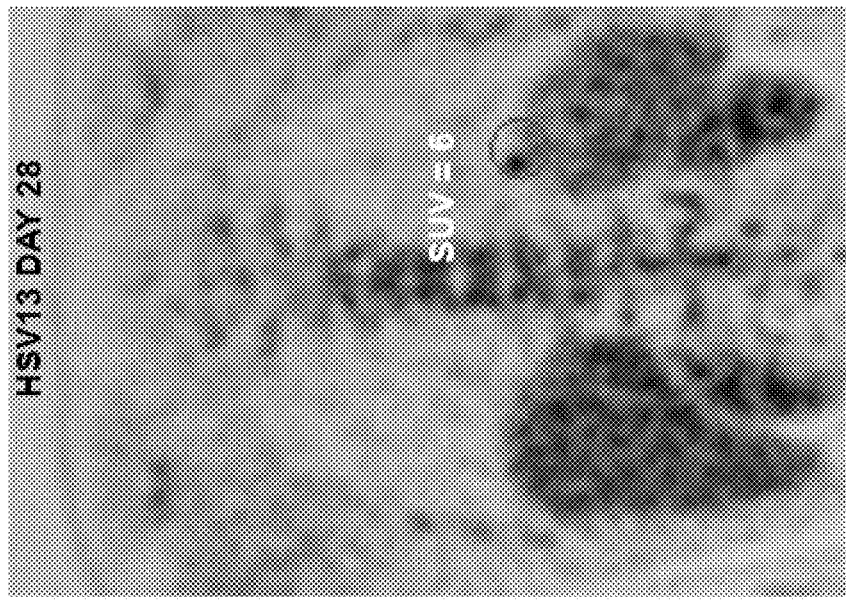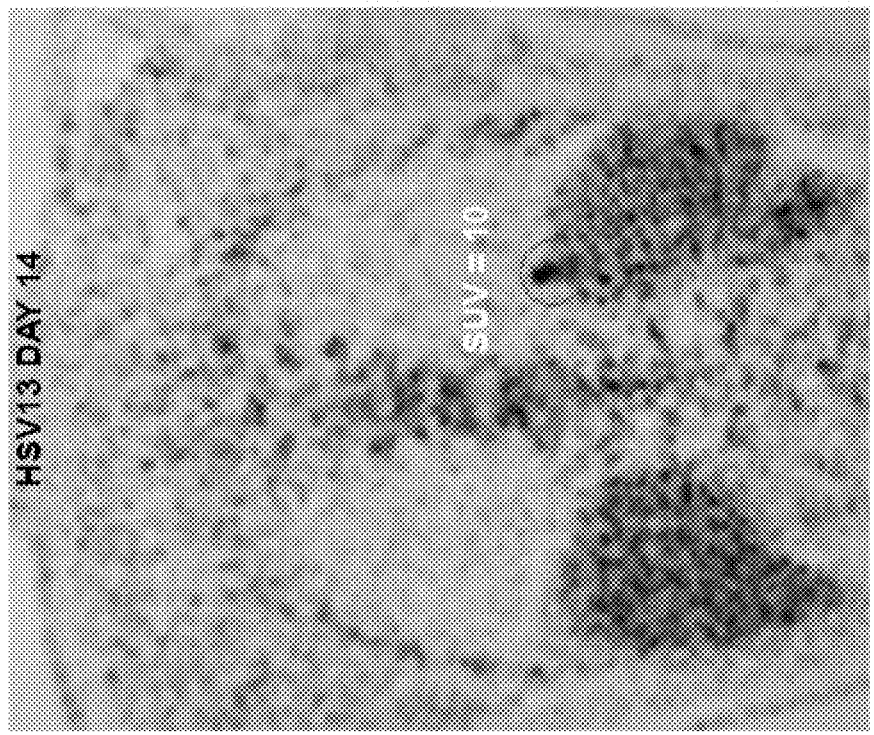
Fig. 60

USE OF ONCOLYTIC HERPES SIMPLEX VIRUS, ALONE OR IN COMBINATION WITH IMMUNE CHECK-POINT INHIBITOR, IN THE TREATMENT OF CANCER

RELATED APPLICATIONS

This application is a continuation of International Patent Application No. PCT/GB2016/052175, filed Jul. 19, 2016, which claims priority to and the benefit of United Kingdom patent application No. 1512723.6 filed on 20 Jul. 2015 and United Kingdom patent application No. 1523091.5 filed on 30 Dec. 2015. The entire contents of these applications are incorporated herein by reference.

FIELD OF THE INVENTION

The present invention relates to the use of an oncolytic herpes simplex virus, and optionally an immune checkpoint inhibitor, in the treatment of cancer.

BACKGROUND TO THE INVENTION

Oncolytic virotherapy concerns the use of lytic viruses which selectively infect and kill cancer cells. Some oncolytic viruses are promising therapies as they display exquisite selection for replication in cancer cells and their self-limiting propagation within tumors results in fewer toxic side effects. Several oncolytic viruses have shown great promise in the clinic (Bell, J., Oncolytic Viruses: An Approved Product on the Horizon? Mol Ther. 2010; 18(2): 233-234).

Cancer cells normally acquire antigenicity that can be recognised by the adaptive immune system as non-self and lead to generation of an immune response involving proliferation of antigen-specific lymphocytes. Tumors are now established to co-opt certain immune checkpoint pathways as a mechanism of immune resistance against T-cells specific for tumor antigens (Drew M. Pardoll, The blockade of immune checkpoints in cancer immunotherapy. Nature Reviews Cancer Vol. 12 Apr. 2012 252-264).

Tumor infiltration with M2-phenotype macrophages and myeloid derived suppressor cells (MDSC) promotes tumor progression whereas infiltration of memory cytotoxic T cells and T helper 1 (Th1) T lymphocytes are often associated with a good clinical outcome and good response to immunotherapy. Therefore, one aim of immunotherapies is to modify the context of immune, inflammatory and angiogenic elements to favour a strong Th1 cytotoxic microenvironment (Giraldo et al., The immune contexture of primary and metastatic human tumors. Current Opinion in Immunology 2014, 27:8-15).

Haabeth et al (Inflammation driven by tumor-specific Th1 cells protects against B-cell cancer. Nature Communications. 2:240 15 Mar. 2011 [DOI:10.1038/ncomms1239]) also report that successful cancer immunosurveillance mediated by tumor-specific CD4$^+$ T cells is consistently associated with elevated levels of both proinflammatory (IL-1α, IL-1β and IL-6) and Th1 associated (interferon-γ (IFN-γ), IL-2 and IL-12) cytokines. They describe cancer eradication as a collaboration between tumor specific Th1 cells and tumor infiltrating, antigen presenting macrophages in which Th1 cells induce secretion of IL-1β and IL-6 by macrophages and Th1 associated IFN-γ renders macrophages directly cytotoxic to cancer cells and causes them to secrete the angiostatic chemokines CXCL9/MIG (monokine induced by IFN-γ) and CXCL10/IP-10 (IFN-γ inducible protein 10), and conclude that inflammation driven by tumor specific Th1 cells may prevent rather than promote cancer. Haabeth et al also report a panel of nine cytokines consistently associated with successful cancer immunosurveillance, including proinflammatory (IL-1α, IL-1β and IL-6) and Th1 associated (IL-2, IL-3, IL-12, IFN-γ, CXCL9 and CXCL10) cytokines.

Whilst the pattern of cytokine production that characterises the T helper type 1 (Th1) and type 2 (Th2) responses is reasonably well understood, it is much less clear how the direction of differentiation towards Th1 or Th2 is decided.

Herpes simplex virus type 1 has evolved several strategies to evade the production and function of interferons (IFNs) and cytokines generated by the innate immune system (which plays a role in activation of the adaptive immune response). HSV counteracts the production of IFN, diminishes IFN-signalling, and blocks the actions of PKR and activation of the 2'-5' A system through several viral products, including ICP0, ICP27, ICP34.5 and vhs (Melchjorsen et al., Activation and Evasion of Innate Antiviral Immunity by Herpes Simplex Virus. *Viruses* 2009, 1, 737-759; doi: 10.3390/v1030737; L. Aurelian., Herpes Simplex Virus Type 2 Vaccines: New Ground for Optimism? Clinical and Diagnostic Laboratory Immunology, May 2004, p. 437-445).

Young J Kim (Subverting the adaptive immune resistance mechanism to improve clinical responses to immune checkpoint blockade therapy. OncoImmunology 3:12 e954868; December 2014) describes a mechanistic and clinical rationale for combining IFN-γ Th1 inducing cancer vaccines with the blockade of the immune checkpoint protein Programmed cell death 1 (PD-1, also called CD279), and indicates that strategies to increase tumor-infiltrating cytotoxic T lymphocyte anticancer activities with immune checkpoint inhibitors may convert anti-PD-1 blockade non-responders to responders, thereby circumventing immune evasion.

Sagiv-Barfi et al reported that ibrutinib, an inhibitor of ITK, an essential enzyme in Th2 T cells can shift the balance between Th1 and Th2 T cells towards Th1 and thereby enhance anti-tumor responses. They describe the combination of anti-PD-L1 antibody and ibrutinib to suppress tumor growth in mouse models of lymphoma that are intrinsically insensitive to ibrutinib, as well as in models of breast and colon cancer (Sagiv-Barfi et al., Therapeutic antitumor immunity by checkpoint blockade is enhanced by ibrutinib, an inhibitor of both BTK and ITK. PNAS E966-972 Published online Feb. 17, 2015).

Oreja-Guevara et al (TH1/TH2 Cytokine profile in relapsing-remitting multiple sclerosis patients treated with Glatiramer acetate or Natalizumab. BMC series open, inclusive and trusted 2012 12:95 DOI: 10.1186/1471-2377-12-95) report that the balance between T helper cells, Th2- and Th1 related cytokines plays a key role in multiple sclerosis and that a shift from a Th1 towards a Th2 cytokine profile could have a beneficial effect on the clinical course of the disease.

Sredni et al (Journal of National Cancer Institute, Vol. 88, no. 18, Sep. 18, 1996) report that the immune response to malignant growths is regulated by distinct patterns of Th2 cytokine production, and investigated the ability of ammonium trichloro[dioxethylene O,O']tellurate (AS101) as an agent capable of re-directing the response towards Th1.

Accordingly, there are advantages for treatment of tumors associated with promoting a Th1 response in the tumor microenvironment, and further ways of establishing such a treatment-favourable environment are required.

When it comes to developing treatments for human patients that involve directed stimulation of parts of the human immune system studies of the effect of oncolytic virus on the immune response in mice must be treated with caution owing to acknowledged differences in immune response between mouse models and humans (Mestas and Hughes., J Immunol 2004; 172:2731-2738).

WO2014/036412 describes the treatment of stage IIIb to stage IV melanoma by a method comprising administering to a patient with stages IIIb to IV melanoma an effective amount of an immune checkpoint inhibitor and a herpes simplex virus, wherein the herpes simplex virus lacks functional ICP34.5 genes, lacks a functional ICP47 gene and comprises a gene encoding human GM-CSF.

SUMMARY OF THE INVENTION

Oncolytic Herpes Simplex Virus Monotherapy

In some aspects, the present invention concerns the use of an oncolytic herpes simplex virus to treat cancer, wherein the subject receives the oncolytic herpes simplex virus and does not receive an immune checkpoint inhibitor as part of the programme of treatment.

The present invention concerns methods of treating or preventing cancer in a subject in need of treatment, the methods comprising administering oncolytic herpes simplex virus to induce a sustained Th1 immune response in the subject.

The present invention also concerns methods of preventing metastasis of cancer in a subject in need of treatment, the methods comprising inducing a sustained Th1 immune response in the subject.

The inventors have identified that induction of a Th1 response through administration of an effective amount of oncolytic herpes simplex virus is effective to trigger an anti-tumor Th1 response in the subject. They have also identified that the anti-tumor Th1 response has a memory effect, and may be used to vaccinate the subject against relapse of the cancer at both primary and distal sites.

In aspects and embodiments of the present invention a method of treating cancer in a subject in need of treatment is provided, the method comprising administering an oncolytic herpes simplex virus (HSV) in sufficient quantity and over a sufficient period of time to induce a sustained Th1 immune response in the subject, thereby contributing to (i) treatment of the cancer at the site of administration, and/or (ii) treatment of the cancer at distal locations, and/or (iii) preventing or reducing metastasis of the cancer, and/or (iv) preventing or reducing relapse of the cancer.

A single administration of oncolytic HSV may be insufficient to generate a sustained Th1 immune response. A course of treatment involving administration of multiple doses of oncolytic HSV may be required to generate and/or maintain a sustained Th1 response. The sustained Th1 response is preferably capable of treating the cancer, and/or preventing metastasis and/or preventing relapse of the cancer. The sustained Th1 response preferably produces a memory Th1 response in the subject in respect of the specific cancer cells against which the Th1 response is induced.

In the context of treatment of a metastatic cancer, treatment may be of cancers or tumors of a given cell type. The treatment may involve eliciting a systemic anti-tumor Th1 immune response in the subject, who may be at risk of developing single or multiple metastatic cancers or tumors of the given cell type. Administration of oncolytic herpes simplex virus may therefore induce a Th1 immune response that is specific for the tumor cell type and that kills cells of inoculated tumor and non-inoculated tumors.

Not all subjects respond to administration of oncolytic HSV by induction of a Th1 response and subjects may therefore be monitored to determine their response to treatment with the oncolytic HSV. Subjects who respond may continue treatment with oncolytic HSV at a dose and/or dosage regime designed to maintain the sustained Th1 response. Subjects who do not respond to treatment by generation of a Th1 response may discontinue treatment with oncolytic HSV, or may transition to combination treatment with oncolytic HSV and one or more additional chemotherapeutic agents.

In preferred embodiments the oncolytic HSV is an HSV that is modified with respect to wild-type so as to inactivate at least one $\gamma_1 34.5$ gene copy, most preferably both copies of the $\gamma_1 34.5$ gene. The oncolytic HSV is preferably not modified to inactivate other HSV genes. The oncolytic HSV is preferably not modified to express any non-HSV genes. In some preferred embodiments the oncolytic HSV is HSV1716.

In one aspect of the present invention an oncolytic herpes simplex virus for use in a method of treating cancer is provided, the method comprising administering one or more doses of an oncolytic herpes simplex virus to the subject effective to induce a sustained Th1 immune response in the subject.

In one aspect of the present invention a method of treating cancer in a subject in need of treatment is provided, the method comprising administering one or more doses of an oncolytic herpes simplex virus to the subject effective to induce a sustained Th1 immune response in the subject.

In one aspect of the present invention the use of an oncolytic herpes simplex virus in the manufacture of a medicament for use in a method of treating cancer in a subject in need of treatment is provided, the method comprising administering one or more doses of an oncolytic herpes simplex virus to the subject effective to induce a sustained Th1 immune response in the subject.

In one aspect of the present invention a n oncolytic herpes simplex virus for use in a method of treating cancer in a subject and preventing relapse of the cancer is provided, the method comprising administering to a subject having a cancer one or more doses of an oncolytic herpes simplex virus effective to induce a sustained Th1 immune response in the subject.

In one aspect of the present invention a method of treating cancer in a subject and preventing relapse of the cancer is provided, the method comprising administering to a subject having a cancer one or more doses of an oncolytic herpes simplex virus effective to induce a sustained Th1 immune response in the subject.

In one aspect of the present invention the use of an oncolytic herpes simplex virus in the manufacture of a medicament for use in a method of treating cancer in a subject and preventing relapse of the cancer is provided, the method comprising administering to a subject having a cancer one or more doses of an oncolytic herpes simplex virus effective to induce a sustained Th1 immune response in the subject.

In one aspect of the present invention a n oncolytic herpes simplex virus for use in a method of preventing relapse of a cancer in a subject is provided, the method comprising administering to a subject having a cancer or having been cured of a cancer one or more doses of an oncolytic herpes simplex virus effective to induce a sustained Th1 immune response in the subject.

In one aspect of the present invention a method of preventing relapse of a cancer in a subject is provided, the method comprising administering to a subject having a cancer or having been cured of a cancer one or more doses of an oncolytic herpes simplex virus effective to induce a sustained Th1 immune response in the subject.

In one aspect of the present invention the use of an oncolytic herpes simplex virus in the manufacture of a medicament for use in a method of preventing relapse of a cancer in a subject is provided, the method comprising administering to a subject having a cancer or having been cured of a cancer one or more doses of an oncolytic herpes simplex virus effective to induce a sustained Th1 immune response in the subject.

In one aspect of the present invention an oncolytic herpes simplex virus for use in a method of preventing metastasis of a cancer in a subject is provided, the method comprising administering to a subject having a cancer one or more doses of an oncolytic herpes simplex virus effective to induce a sustained Th1 immune response in the subject. In one aspect of the present invention a method of preventing metastasis of a cancer in a subject is provided, the method comprising administering to a subject having a cancer one or more doses of an oncolytic herpes simplex virus effective to induce a sustained Th1 immune response in the subject.

In one aspect of the present invention the use of an oncolytic herpes simplex virus in the manufacture of a medicament for use in a method of preventing metastasis of a cancer in a subject is provided, the method comprising administering to a subject having a cancer one or more doses of an oncolytic herpes simplex virus effective to induce a sustained Th1 immune response in the subject.

The method may comprise administering more than one dose of oncolytic herpes simplex virus.

The method may comprise administering 2, 3, or 4 doses of oncolytic herpes simplex virus to the subject at regular intervals. The subject may receive a weekly or fortnightly dose of oncolytic herpes simplex virus for one of at least 2, 3, 4, 5, 6, 7, 8, weeks or 1, 2, 3, 4, 5, or 6 months.

The method may comprise administration of a herpes simplex virus for a period of time sufficient to induce a sustained Th1 response in the subject.

The method may comprise administration of an oncolytic herpes simplex virus for a period of time sufficient to induce a sustained Th1 response in the subject, in which period of time the subject does not receive an immune checkpoint inhibitor.

The method may comprise administration of the oncolytic herpes simplex virus by infusion to the blood.

The method may further comprise the step of determining the presence of a Th1 response in the subject. Such determination may be conducted at desired intervals by analysing the level of cytokine expression in a sample taken from a subject. As such monitoring of the existence and/or status of a Th1 response may be conducted, daily, weekly, fortnightly, monthly or yearly as desired and/or consider appropriate by a medical practitioner.

Determining the presence of a Th1 response may comprise measuring the level of IFNγ, IL-2 and/or IL-12 in a sample obtained from a subject. In some preferred embodiments determining the presence of a Th1 response may comprise measuring the level of IL-2 and/or IL-12 in a sample obtained from a subject.

The subject may be a human and optionally a human child. Subjects to be treated may have been diagnosed as having a cancer, be considered at risk of developing a cancer, have been cured of cancer and considered at risk of relapse.

In some preferred embodiments the oncolytic herpes simplex virus is a mutant of HSV-1 strain 17 or is HSV1716. Optionally the oncolytic herpes simplex virus does not express GMCSF, and/or encodes a functional ICP47 and/or ICP6 gene.

In some embodiments the cancer is a solid tumor, optionally not a melanoma.

Optionally, in some embodiments the herpes simplex virus does not express GMCSF, and/or the herpes simplex virus encodes a functional ICP47 and/or ICP6 gene, and/or the cancer is not a melanoma.

In some embodiments the subject has been treated with an oncolytic herpes simplex virus and is, or has been, selected as having a Th1 immune response.

In some embodiments the method may comprise administering one or more doses of the oncolytic herpes simplex virus effective to induce a Th1 immune response.

Accordingly, in one aspect of the present invention a method of treating cancer in a subject in need of treatment is provided, the method comprising administering one or more doses of an oncolytic herpes simplex virus effective to induce a Th1 immune response in the subject.

An oncolytic herpes simplex virus for use in a method of treating cancer is provided, the method comprising administering one or more doses of an oncolytic herpes simplex virus effective to induce a Th1 immune response in the subject.

Use of an oncolytic herpes simplex virus in the manufacture of a medicament for use in a method of treatment of cancer is provided, wherein the method of treatment comprises administering one or more doses of an oncolytic herpes simplex virus effective to induce a Th1 immune response in the subject.

In some embodiments the method may comprise administering one or more doses of the oncolytic herpes simplex virus effective to induce a Th1 immune response.

In some embodiments the method may comprise the step of determining the presence of a Th1 immune response in the subject.

In some embodiments the method may comprise the step of selecting a subject in which a Th1 immune response is induced or elicited by the oncolytic herpes simplex virus.

Accordingly, in one aspect of the present invention a method of treating cancer in a subject in need of treatment is provided, the method comprising administering one or more doses of an oncolytic herpes simplex virus to the subject, and determining the presence of a Th1 immune response in the subject.

An oncolytic herpes simplex virus for use in a method of treating cancer is provided, the method comprising administering one or more doses of an oncolytic herpes simplex virus to the subject, and determining the presence of a Th1 immune response in the subject.

An immune checkpoint inhibitor for use in a method of treating cancer is provided, the method comprising administering one or more doses of an oncolytic herpes simplex virus to the subject, and determining the presence of a Th1 immune response in the subject.

Use of an oncolytic herpes simplex virus in the manufacture of a medicament for use in a method of treatment of cancer is provided, the method comprising administering one or more doses of an oncolytic herpes simplex virus to the subject, and determining the presence of a Th1 immune response in the subject.

In some embodiments administration of the oncolytic herpes simplex virus is for a period of time sufficient to induce or elicit a Th1 response in the subject.

In some embodiments all copies of the ICP34.5 gene in the genome of the oncolytic herpes simplex virus are modified such that the ICP34.5 gene is incapable of expressing a functional ICP34.5 gene product. As such the oncolytic herpes simplex virus may be an ICP34.5 null mutant.

In some embodiments one or both of the ICP34.5 genes in the genome of the oncolytic herpes simplex virus are modified such that the ICP34.5 gene is incapable of expressing a functional ICP34.5 gene product.

In some embodiments the oncolytic herpes simplex virus is a mutant of HSV-1 strain 17. In preferred embodiments the oncolytic herpes simplex virus is HSV1716 (ECACC Accession No. V92012803). HSV1716 is also called SEP-REHVIR®. In some embodiments the herpes simplex virus is a mutant of HSV-1 strain 17 mutant 1716.

In some embodiments an immune checkpoint inhibitor is an inhibitor of at least one of CTLA4, PD-1, PD-L1, TIM-3 or LAG-3.

Optionally, in some embodiments the oncolytic herpes simplex virus does not express GMCSF. Optionally, in some embodiments the oncolytic herpes simplex virus encodes a functional ICP47 gene. Optionally, in some embodiments the oncolytic herpes simplex virus encodes a functional ICP6 gene. Optionally, in some embodiments the oncolytic herpes simplex virus is not a herpes simplex virus that lacks functional ICP34.5 genes and lacks a functional ICP47 gene and comprises a gene encoding human GM-CSF.

Optionally, in some embodiments the cancer is not a melanoma. Optionally, in some embodiments the cancer is not a primary melanoma. Optionally, in some embodiments the cancer is not a metastatic (secondary) melanoma. Optionally, in some embodiments the cancer is not stage Mb to stage IV melanoma.

The dose of oncolytic herpes simplex virus administered may be at least $1\times10^6$ iu. In some embodiments, a dose of oncolytic herpes simplex virus is administered over a period of 3 hours or less. In some embodiments, the administered oncolytic herpes simplex virus is formulated as about 0.5 ml to about 5 ml of a suspension of virus in about 200 ml to about 300 ml of lactated Ringer's solution. In some embodiments the administered oncolytic herpes simplex virus is formulated as about 1.0 ml of a suspension of virus in about 250 ml of lactated Ringer's solution.

In another aspect of the present invention an oncolytic herpes simplex virus is provided for use in a method of treating cancer in a human subject in need of treatment is provided, the method comprising administering to the human subject at least one treatment cycle of oncolytic herpes simplex virus, wherein a treatment cycle comprises, or consists of:
  (i) four doses of oncolytic herpes simplex virus over a period of about four weeks, one dose administered per week by infusion to the blood, each dose of oncolytic herpes simplex virus being in the range about $1\times10^7$ iu to about $1\times10^8$ iu; or
  (ii) four doses of oncolytic herpes simplex virus over a period of about two weeks, two doses administered per week by infusion to the blood, each dose of oncolytic herpes simplex virus being in the range about $1\times10^7$ iu to about $1\times10^8$ iu,
wherein administration of oncolytic herpes simplex virus according to the at least one treatment cycle is effective to induce a sustained Th1 immune response in the subject.

In another aspect of the present invention the use of an oncolytic herpes simplex virus for use in the manufacture of a medicament for use in a method of treating cancer in a human subject is provided, the method comprising administering to the human subject at least one treatment cycle of oncolytic herpes simplex virus, wherein a treatment cycle comprises, or consists, of:
  (i) four doses of oncolytic herpes simplex virus over a period of about four weeks, one dose administered per week by infusion to the blood, each dose of oncolytic herpes simplex virus being in the range about $1\times10^7$ iu to about $1\times10^8$ iu; or
  (ii) four doses of oncolytic herpes simplex virus over a period of about two weeks, two doses administered per week by infusion to the blood, each dose of oncolytic herpes simplex virus being in the range about $1\times10^7$ iu to about $1\times10^8$ iu,
wherein administration of oncolytic herpes simplex virus according to the at least one treatment cycle is effective to induce a sustained Th1 immune response in the subject.

In another aspect of the present invention a method of treating cancer in a human subject in need of treatment is provided, the method comprising administering to the human subject at least one treatment cycle of oncolytic herpes simplex virus, wherein a treatment cycle comprises, or consists, of:
  (i) four doses of oncolytic herpes simplex virus over a period of about four weeks, one dose administered per week by infusion to the blood, each dose of oncolytic herpes simplex virus being in the range about $1\times10^7$ iu to about $1\times10^8$ iu; or
  (ii) four doses of oncolytic herpes simplex virus over a period of about two weeks, two doses administered per week by infusion to the blood, each dose of oncolytic herpes simplex virus being in the range about $1\times10^7$ iu to about $1\times10^8$ iu,
wherein administration of oncolytic herpes simplex virus according to the at least one treatment cycle is effective to induce a sustained Th1 immune response in the subject.

In some embodiments, administration of each weekly dose of oncolytic herpes simplex virus in (i) is separated by 7±1 or 7±2 days.

In some embodiments, administration of each twice weekly dose of oncolytic herpes simplex virus in (ii) is separated by 4±1 or 4±2 days In some embodiments, the subject receives two or more treatment cycles. In some embodiments, the subject receives two or more treatment cycles consecutively. In some embodiments, the subject receives two or more treatment cycles, each treatment cycle separated by a break from treatment. The break from treatment may be about 1, 2, 3, or 4 weeks.

In some embodiments, the first 1, 2 or 3 treatment cycles comprises administration of a dosage of oncolytic herpes simplex virus that is lower than the dosage administered in later treatment cycles.

In some embodiments, the method comprises determining the presence of a Th1 response in the subject. The method may comprise measuring the level of IFNγ, IL-2 and/or IL-12 in a sample obtained from a subject. The level of IL-2 and/or IL-12 and/or IFN-γ in the subject's blood may be upregulated for more than 7 days after one or more treatment cycles of oncolytic herpes simplex virus.

The oncolytic herpes simplex virus may be a mutant of HSV-1 strain 17 or is HSV1716. In some embodiments, the oncolytic herpes simplex virus does not encode (or is not further modified to contain nucleic acid encoding) a cytokine or chemokine, an interleukin, an interferon, a tumor necrosis factor, a colony stimulating factor, an immune modulator, a member of the CC family, a member of the CXC family or a member of the CXC family. In some embodiments, oncolytic herpes simplex virus does not express GMCSF. In some embodiments, the oncolytic herpes simplex virus encodes a functional ICP47 and/or ICP6 gene.

The cancer may be a solid tumor. The cancer may be a recurrent or metastatic solid tumor. The cancer may be in a child. In some embodiments, the cancer is not a melanoma.

Oncolytic Herpes Simplex Virus and Immune Checkpoint Inhibitor Co-Therapy

In some other aspects, the present invention concerns the use of an oncolytic herpes simplex virus to treat cancer, wherein the subject receives the oncolytic herpes simplex virus and an immune checkpoint inhibitor as part of the programme of treatment.

The oncolytic herpes simplex virus and immune checkpoint inhibitor are administered as part of a method of treating cancer in the subject. They may be administered simultaneously, e.g. as a combined preparation or as separate preparations one administered immediately after the other. Alternatively, they may be administered separately and sequentially, where one agent is administered and then the other administered later after a predetermined time interval.

In one aspect of the present invention a method of treating cancer in a subject is provided, the method comprising administering a therapeutically effective amount of an immune checkpoint inhibitor to a subject in need of treatment wherein the subject has been treated with an oncolytic herpes simplex virus.

An oncolytic herpes simplex virus for use in a method of treating cancer is provided, the method comprising administering a therapeutically effective amount of an immune checkpoint inhibitor to a subject in need of treatment wherein the subject has been treated with an oncolytic herpes simplex virus.

An immune checkpoint inhibitor for use in a method of treating cancer is provided, the method comprising administering a therapeutically effective amount of an immune checkpoint inhibitor to a subject in need of treatment wherein the subject has been treated with an oncolytic herpes simplex virus.

Use of an oncolytic herpes simplex virus in the manufacture of a medicament for use in a method of treatment of cancer is provided, the method comprising administering a therapeutically effective amount of an immune checkpoint inhibitor to a subject in need of treatment wherein the subject has been treated with an oncolytic herpes simplex virus.

Use of an immune checkpoint inhibitor in the manufacture of a medicament for use in a method of treatment of cancer is provided, the method comprising administering a therapeutically effective amount of an immune checkpoint inhibitor to a subject in need of treatment wherein the subject has been treated with an oncolytic herpes simplex virus.

Optionally, in some embodiments the herpes simplex virus does not express GMCSF, and/or the herpes simplex virus encodes a functional ICP47 and/or ICP6 gene, and/or the cancer is not a melanoma.

In some embodiments the subject has been treated with an oncolytic herpes simplex virus and is, or has been, selected for treatment with the immune checkpoint inhibitor as having a Th1 immune response.

In one aspect of the present invention a method of treating cancer is provided, the method comprising simultaneous or sequential of administration of an oncolytic herpes simplex virus and an immune checkpoint inhibitor.

An oncolytic herpes simplex virus for use in a method of treating cancer is provided, the method comprising simultaneous or sequential administration of an oncolytic herpes simplex virus and an immune checkpoint inhibitor.

An immune checkpoint inhibitor for use in a method of treating cancer is provided, the method comprising simultaneous or sequential administration of an immune checkpoint inhibitor and an oncolytic herpes simplex virus.

Use of an oncolytic herpes simplex virus in the manufacture of a medicament for use in a method of treatment of cancer is provided, the method comprising simultaneous or sequential administration of an immune checkpoint inhibitor to the subject in need of treatment.

Use of an immune checkpoint inhibitor in the manufacture of a medicament for use in a method of treatment of cancer is provided, the method comprising simultaneous or sequential administration of an oncolytic herpes simplex virus to the subject in need of treatment.

In some embodiments the method may comprise administering one or more doses of the oncolytic herpes simplex virus effective to induce a Th1 immune response.

Accordingly, in one aspect of the present invention a method of treating cancer in a subject in need of treatment is provided, the method comprising administering one or more doses of an oncolytic herpes simplex virus effective to induce a Th1 immune response in the subject, and administering a therapeutically effective amount of an immune checkpoint inhibitor.

An oncolytic herpes simplex virus for use in a method of treating cancer is provided, the method comprising administering one or more doses of an oncolytic herpes simplex virus effective to induce a Th1 immune response in the subject, and administering a therapeutically effective amount of an immune checkpoint inhibitor.

An immune checkpoint inhibitor for use in a method of treating cancer is provided, the method comprising administering one or more doses of an oncolytic herpes simplex virus effective to induce a Th1 immune response in the subject, and administering a therapeutically effective amount of an immune checkpoint inhibitor.

Use of an oncolytic herpes simplex virus in the manufacture of a medicament for use in a method of treatment of cancer is provided, wherein the method of treatment comprises administering one or more doses of an oncolytic herpes simplex virus effective to induce a Th1 immune response in the subject, and administering a therapeutically effective amount of an immune checkpoint inhibitor.

Use of an immune checkpoint inhibitor in the manufacture of a medicament for use in a method of treatment of cancer is provided, wherein the method of treatment comprises administering one or more doses of an oncolytic herpes simplex virus effective to induce a Th1 immune response in the subject, and administering a therapeutically effective amount of an immune checkpoint inhibitor.

In some embodiments the method may comprise administering one or more doses of the oncolytic herpes simplex virus effective to induce a Th1 immune response.

In one aspect of the present invention a method of treating cancer in a subject in need of treatment is provided, the method comprising administering one or more doses of an oncolytic herpes simplex virus to a subject, and administering to a subject in which a Th1 immune response is induced or elicited a therapeutically effective amount of an immune checkpoint inhibitor.

An oncolytic herpes simplex virus for use in a method of treating cancer is provided, the method comprising administering one or more doses of an oncolytic herpes simplex virus to a subject, and administering to a subject in which a Th1 immune response is induced or elicited a therapeutically effective amount of an immune checkpoint inhibitor.

An immune checkpoint inhibitor for use in a method of treating cancer is provided, the method comprising administering one or more doses of an oncolytic herpes simplex virus to a subject, and administering to a subject in which a Th1 immune response is induced or elicited a therapeutically effective amount of an immune checkpoint inhibitor.

Use of an oncolytic herpes simplex virus in the manufacture of a medicament for use in a method of treatment of cancer is provided, the method comprising administering one or more doses of an oncolytic herpes simplex virus to a subject, and administering to a subject in which a Th1 immune response is induced or elicited a therapeutically effective amount of an immune checkpoint inhibitor.

Use of an immune checkpoint inhibitor in the manufacture of a medicament for use in a method of treatment of cancer is provided, the method comprising administering one or more doses of an oncolytic herpes simplex virus to a subject, and administering to a subject in which a Th1 immune response is induced or elicited a therapeutically effective amount of an immune checkpoint inhibitor.

In some embodiments the method may comprise the step of determining the presence of a Th1 immune response in the subject, optionally prior to administration of the immune checkpoint inhibitor. Such determination may be conducted at desired intervals by analysing the level of cytokine expression in a sample taken from a subject. As such monitoring of the existence and/or status of a Th1 response may be conducted, daily, weekly, fortnightly, monthly or yearly as desired and/or consider appropriate by a medical practitioner.

Determining the presence of a Th1 response may comprise measuring the level of IFNγ, IL-2 and/or IL-12 in a sample obtained from a subject. In some preferred embodiments determining the presence of a Th1 response may comprise measuring the level of IL-2 and/or IL-12 in a sample obtained from a subject.

In some embodiments the method may comprise the step of selecting a subject in which a Th1 immune response is induced or elicited by the oncolytic herpes simplex virus for treatment with the immune checkpoint inhibitor, said selection preferably being made prior to administration of the immune checkpoint inhibitor.

Accordingly, in one aspect of the present invention a method of treating cancer in a subject in need of treatment is provided, the method comprising administering one or more doses of an oncolytic herpes simplex virus to the subject, determining the presence of a Th1 immune response in the subject, administering to a subject in which a Th1 immune response is induced or elicited a therapeutically effective amount of an immune checkpoint inhibitor.

An oncolytic herpes simplex virus for use in a method of treating cancer is provided, the method comprising administering one or more doses of an oncolytic herpes simplex virus to the subject, determining the presence of a Th1 immune response in the subject, administering to a subject in which a Th1 immune response is induced or elicited a therapeutically effective amount of an immune checkpoint inhibitor.

An immune checkpoint inhibitor for use in a method of treating cancer is provided, the method comprising administering one or more doses of an oncolytic herpes simplex virus to the subject, determining the presence of a Th1 immune response in the subject, administering to a subject in which a Th1 immune response is induced or elicited a therapeutically effective amount of an immune checkpoint inhibitor.

Use of an oncolytic herpes simplex virus in the manufacture of a medicament for use in a method of treatment of cancer is provided, the method comprising administering one or more doses of an oncolytic herpes simplex virus to the subject, determining the presence of a Th1 immune response in the subject, administering to a subject in which a Th1 immune response is induced or elicited a therapeutically effective amount of an immune checkpoint inhibitor.

Use of an immune checkpoint inhibitor in the manufacture of a medicament for use in a method of treatment of cancer is provided, the method comprising administering one or more doses of an oncolytic herpes simplex virus to the subject, determining the presence of a Th1 immune response in the subject, administering to a subject in which a Th1 immune response is induced or elicited a therapeutically effective amount of an immune checkpoint inhibitor.

In one aspect of the present invention a method of treating cancer in a subject in need of treatment is provided, the method comprising administering one or more doses of an oncolytic herpes simplex virus to the subject, selecting a subject in which a Th1 immune response is induced or elicited for treatment with an immune checkpoint inhibitor, and administering to a selected subject a therapeutically effective amount of an immune checkpoint inhibitor.

An oncolytic herpes simplex virus for use in a method of treating cancer is provided, the method comprising administering one or more doses of an oncolytic herpes simplex virus to the subject, selecting a subject in which a Th1 immune response is induced or elicited for treatment with an immune checkpoint inhibitor, and administering to a selected subject a therapeutically effective amount of an immune checkpoint inhibitor.

An immune checkpoint inhibitor for use in a method of treating cancer is provided, the method comprising administering one or more doses of an oncolytic herpes simplex virus to the subject, selecting a subject in which a Th1 immune response is induced or elicited for treatment with an immune checkpoint inhibitor, and administering to a selected subject a therapeutically effective amount of an immune checkpoint inhibitor.

Use of an oncolytic herpes simplex virus in the manufacture of a medicament for use in a method of treatment of cancer is provided, the method comprising administering one or more doses of an oncolytic herpes simplex virus to the subject, selecting a subject in which a Th1 immune response is induced or elicited for treatment with an immune checkpoint inhibitor, and administering to a selected subject a therapeutically effective amount of an immune checkpoint inhibitor.

Use of an immune checkpoint inhibitor in the manufacture of a medicament for use in a method of treatment of cancer is provided, the method comprising administering one or more doses of an oncolytic herpes simplex virus to the subject, selecting a subject in which a Th1 immune response is induced or elicited for treatment with an immune checkpoint inhibitor, and administering to a selected subject a therapeutically effective amount of an immune checkpoint inhibitor.

In some embodiments the method comprises selecting a subject in which a Th1 immune response is induced or elicited by the oncolytic herpes simplex virus for treatment with the immune checkpoint inhibitor. In some embodiments administration of the oncolytic herpes simplex virus is for a period of time sufficient to induce or elicit a Th1 response in the subject.

In some embodiments administration of the oncolytic herpes simplex virus is for a period of time prior to treatment with an immune checkpoint inhibitor in which period the subject is administered oncolytic herpes simplex virus but is not administered an immune checkpoint inhibitor.

In some embodiments all copies of the ICP34.5 gene in the genome of the oncolytic herpes simplex virus are modified such that the ICP34.5 gene is incapable of expressing a functional ICP34.5 gene product. As such the oncolytic herpes simplex virus may be an ICP34.5 null mutant.

In some embodiments one or both of the ICP34.5 genes in the genome of the oncolytic herpes simplex virus are modified such that the ICP34.5 gene is incapable of expressing a functional ICP34.5 gene product.

In some embodiments the oncolytic herpes simplex virus is a mutant of HSV-1 strain 17. In preferred embodiments the oncolytic herpes simplex virus is HSV1716 (ECACC Accession No. V92012803). HSV1716 is also called SEPREHVIR®. In some embodiments the herpes simplex virus is a mutant of HSV-1 strain 17 mutant 1716.

In some embodiments the immune checkpoint inhibitor is an inhibitor of at least one of CTLA4, PD-1, PD-L1, TIM-3 or LAG-3.

In one aspect of the present invention a pharmaceutical composition comprising an oncolytic herpes simplex virus and an immune checkpoint inhibitor is provided. The oncolytic herpes simplex virus may be a mutant of HSV-1 strain 17. In preferred embodiments the oncolytic herpes simplex virus is HSV1716.

In one aspect of the present invention a kit is provided, the kit comprising a predetermined amount of oncolytic herpes simplex virus and a predetermined amount of an immune checkpoint inhibitor. The oncolytic herpes simplex virus may be a mutant of HSV-1 strain 17. In preferred embodiments the oncolytic herpes simplex virus is HSV1716. The kit may be provided together with instructions for the administration of the oncolytic herpes simplex virus, and immune checkpoint inhibitor sequentially or simultaneously in order to provide a treatment for cancer.

In one aspect of the present invention products are provided containing therapeutically effective amounts of:
(i) HSV1716, and
(ii) an immune checkpoint inhibitor
for simultaneous or sequential use in a method of medical treatment, preferably treatment of cancer. The products may be pharmaceutically acceptable formulations and may optionally be formulated as a combined preparation for coadministration.

Optionally, in some embodiments the oncolytic herpes simplex virus does not express GMCSF. Optionally, in some embodiments the oncolytic herpes simplex virus encodes a functional ICP47 gene. Optionally, in some embodiments the oncolytic herpes simplex virus encodes a functional ICP6 gene. Optionally, in some embodiments the oncolytic herpes simplex virus is not a herpes simplex virus that lacks functional ICP34.5 genes and lacks a functional ICP47 gene and comprises a gene encoding human GM-CSF.

Optionally, in some embodiments the cancer is not a melanoma. Optionally, in some embodiments the cancer is not a primary melanoma. Optionally, in some embodiments the cancer is not a metastatic (secondary) melanoma. Optionally, in some embodiments the cancer is not stage IIIb to stage IV melanoma.

The dose of oncolytic herpes simplex virus administered may be at least $1\times10^6$ iu. In some embodiments, a dose of oncolytic herpes simplex virus is administered over a period of 3 hours or less. In some embodiments, the administered oncolytic herpes simplex virus is formulated as about 0.5 ml to about 5 ml of a suspension of virus in about 200 ml to about 300 ml of lactated Ringer's solution. In some embodiments the administered oncolytic herpes simplex virus is formulated as about 1.0 ml of a suspension of virus in about 250 ml of lactated Ringer's solution.

In another aspect of the present invention an oncolytic herpes simplex virus is provided for use in a method of treating cancer in a human subject is provided, the method comprising administering to the human subject an oncolytic herpes simplex virus and a therapeutically effective amount of an immune checkpoint inhibitor, wherein the method comprises at least one treatment cycle of oncolytic herpes simplex virus comprising, or consisting, of:
(i) four doses of oncolytic herpes simplex virus over a period of about four weeks, one dose administered per week by infusion to the blood, each dose of oncolytic herpes simplex virus being in the range about $1\times10^7$ iu to about $1\times10^8$ iu; or
(ii) four doses of oncolytic herpes simplex virus over a period of about two weeks, two doses administered per week by infusion to the blood, each dose of oncolytic herpes simplex virus being in the range about $1\times10^7$ iu to about $1\times10^8$ iu,
wherein administration of oncolytic herpes simplex virus according to the at least one treatment cycle is effective to induce a sustained Th1 immune response in the subject.

In another aspect of the present invention the use of an oncolytic herpes simplex virus is provided for use in the manufacture of a medicament for use in a method of treating cancer in a human subject, the method comprising administering to the human subject an oncolytic herpes simplex virus and a therapeutically effective amount of an immune checkpoint inhibitor, wherein the method comprises at least one treatment cycle of oncolytic herpes simplex virus comprising, or consisting, of:
(i) four doses of oncolytic herpes simplex virus over a period of about four weeks, one dose administered per week by infusion to the blood, each dose of oncolytic herpes simplex virus being in the range about $1\times10^7$ iu to about $1\times10^8$ iu; or
(ii) four doses of oncolytic herpes simplex virus over a period of about two weeks, two doses administered per week by infusion to the blood, each dose of oncolytic herpes simplex virus being in the range about $1\times10^7$ iu to about $1\times10^8$ iu,
wherein administration of oncolytic herpes simplex virus according to the at least one treatment cycle is effective to induce a sustained Th1 immune response in the subject.

In another aspect of the present invention a method of treating cancer in a human subject in need of treatment is provided, the method comprising administering to the human subject an oncolytic herpes simplex virus and a therapeutically effective amount of an immune checkpoint inhibitor, wherein the method comprises at least one treatment cycle of oncolytic herpes simplex virus comprising, or consisting, of:
(i) four doses of oncolytic herpes simplex virus over a period of about four weeks, one dose administered per week by infusion to the blood, each dose of oncolytic herpes simplex virus being in the range about $1\times10^7$ iu to about $1\times10^8$ iu; or (ii) four doses of oncolytic herpes simplex virus over a period of about two weeks, two doses administered per week by infusion to the blood, each dose of oncolytic herpes simplex virus being in the range about $1 \times 10^7$ iu to about $1 \times 10^8$ iu, wherein administration of oncolytic herpes simplex virus according to the at least one treatment cycle is effective to induce a sustained Th1 immune response in the subject.

In some embodiments, the method comprises administering an immune checkpoint inhibitor according to at least one treatment cycle of immune checkpoint inhibitor, wherein the periods of time of the oncolytic herpes simplex treatment cycle and immune checkpoint inhibitor treatment cycle overlap.

In some embodiments, the method comprises at least one treatment cycle of immune checkpoint inhibitor comprising, or consisting, of 1 or 2 doses of immune checkpoint inhibitor administered within a period of about 3 or 4 weeks.

In some embodiments, the method comprises at least one treatment cycle of immune checkpoint inhibitor comprising, or consisting, of a period of about 3 weeks in which 1 dose of immune checkpoint inhibitor is administered. The method may comprise at least one treatment cycle of immune checkpoint inhibitor comprising, or consisting, of 1 dose of immune checkpoint inhibitor administered about every 3 weeks. The method may comprise at least two treatment cycles of oncolytic herpes simplex virus according to (i) and at least two treatment cycles of immune checkpoint inhibitor each comprising, or consisting, of a period of about 3 weeks in which 1 dose of immune checkpoint inhibitor is administered, wherein the periods of time of the first treatment cycle of oncolytic herpes simplex virus and first treatment cycle of immune checkpoint inhibitor overlap. The method may comprise at least two treatment cycles of oncolytic herpes simplex virus according to (ii) and a treatment cycle of immune checkpoint inhibitor comprising, or consisting of, a period of about 3 weeks in which 1 dose of immune checkpoint inhibitor is administered, wherein the periods of time of the treatment cycles of oncolytic herpes simplex virus and treatment cycle of immune checkpoint inhibitor overlap.

In some embodiments, administration of each weekly dose of oncolytic herpes simplex virus in (i) is separated by 7±1 or 7±2 days.

In some embodiments, administration of each twice weekly dose of oncolytic herpes simplex virus in (ii) is separated by 4±1 or 4±2 days In some embodiments, the subject receives two or more treatment cycles of oncolytic herpes simplex virus and two or more treatment cycles of immune checkpoint inhibitor. In some embodiments, the subject receives two or more treatment cycles of oncolytic herpes simplex virus and two or more treatment cycles of immune checkpoint inhibitor, the treatment cycles being consecutive.

In some embodiments, the first 1, 2 or 3 treatment cycles of oncolytic herpes simplex virus comprises administration of a dosage of oncolytic herpes simplex virus that is lower than the dosage administered in later treatment cycles.

In some embodiments, the method comprises determining the presence of a Th1 response in the subject. The method may comprise measuring the level of IFNγ, IL-2 and/or IL-12 in a sample obtained from a subject. The level of IL-2 and/or IL-12 and/or IFN-γ in the subject's blood may be upregulated for more than 7 days after one or more treatment cycles of oncolytic herpes simplex virus.

The oncolytic herpes simplex virus may be a mutant of HSV-1 strain 17 or is HSV1716. In some embodiments, the oncolytic herpes simplex virus does not encode (or is not further modified to contain nucleic acid encoding) a cytokine or chemokine, an interleukin, an interferon, a tumor necrosis factor, a colony stimulating factor, an immune modulator, a member of the CC family, a member of the CXC family or a member of the CXC family. In some embodiments, oncolytic herpes simplex virus does not express GMCSF. In some embodiments, the oncolytic herpes simplex virus encodes a functional ICP47 and/or ICP6 gene.

The immune checkpoint inhibitor may be an inhibitor of at least one of CTLA4, PD-1, PD-L1, TIM-3 or LAG-3.

The cancer may be a solid tumor. The cancer may be a recurrent or metastatic solid tumor. The cancer may be in a child. In some embodiments, the cancer is not a melanoma.

The following numbered paragraphs contain statements of broad combinations of the inventive technical features herein disclosed:—

1. An oncolytic herpes simplex virus for use in a method of treating cancer, the method comprising administering one or more doses of an oncolytic herpes simplex virus effective to induce a Th1 immune response in the subject, and administering a therapeutically effective amount of an immune checkpoint inhibitor.

2. An immune checkpoint inhibitor for use in a method of treating cancer, the method comprising administering one or more doses of an oncolytic herpes simplex virus effective to induce a Th1 immune response in the subject, and administering a therapeutically effective amount of an immune checkpoint inhibitor.

3. The oncolytic herpes simplex virus or immune checkpoint inhibitor for use in a method of treating cancer according to paragraph 1 or 2 wherein the method comprises determining the presence of a Th1 immune response in the subject.

4. The oncolytic herpes simplex virus or immune checkpoint inhibitor for use in a method of treating cancer according to any one of paragraphs 1 to 3 wherein the method comprises selecting a subject in which a Th1 immune response is induced or elicited by the oncolytic herpes simplex virus for treatment with the immune checkpoint inhibitor.

5. The oncolytic herpes simplex virus or immune checkpoint inhibitor for use in a method of treating cancer according to any one of paragraphs 1 to 4 wherein administration of the oncolytic herpes simplex virus is for a period of time sufficient to induce or elicit a Th1 response in the subject.

6. The oncolytic herpes simplex virus or immune checkpoint inhibitor for use in a method of treating cancer according to any one of paragraphs 1 to 5 wherein administration of the oncolytic herpes simplex virus is for a period of time prior to treatment with an immune checkpoint inhibitor in which period the subject is administered oncolytic herpes simplex virus but is not administered an immune checkpoint inhibitor.

7. The oncolytic herpes simplex virus or immune checkpoint inhibitor for use in a method of treating cancer according to any one of paragraphs 1 to 6 wherein:
    (i) the oncolytic herpes simplex virus does not express GMCSF, and/or
    (ii) the oncolytic herpes simplex virus encodes a functional ICP47 gene, and/or
    (iii) the cancer is not a melanoma.

8. The oncolytic herpes simplex virus or immune checkpoint inhibitor for use in a method of treating cancer according to any one of paragraphs 1 to 7 wherein the oncolytic herpes simplex virus is a mutant of HSV-1 strain 17.

9. The oncolytic herpes simplex virus or immune checkpoint inhibitor for use in a method of treating cancer according to any one of paragraphs 1 to 6 wherein the oncolytic herpes simplex virus is HSV1716.

10. The oncolytic herpes simplex virus or immune checkpoint inhibitor for use in a method of treating cancer according to any one of paragraphs 1 to 9 wherein the immune checkpoint inhibitor is an inhibitor of at least one of CTLA4, PD-1, PD-L1, TIM-3 or LAG-3.

11. A pharmaceutical composition comprising an oncolytic herpes simplex virus and an immune checkpoint inhibitor, wherein the oncolytic herpes simplex virus encodes a functional ICP47 gene and/or does not express GMCSF.

12. A pharmaceutical composition comprising an oncolytic herpes simplex virus and an immune checkpoint inhibitor, wherein the oncolytic herpes simplex virus is a mutant of HSV-1 strain 17 or is HSV1716.

13. The pharmaceutical composition of paragraph 11 or 12 wherein the immune checkpoint inhibitor is an inhibitor of at least one of CTLA4, PD-1, PD-L1, TIM-3 or LAG-3.

14. A kit comprising a predetermined amount of oncolytic herpes simplex virus and a predetermined amount of an immune checkpoint inhibitor, wherein the oncolytic herpes simplex virus encodes a functional ICP47 gene and/or does not express GMCSF.

15. A kit comprising a predetermined amount of oncolytic herpes simplex virus and a predetermined amount of an immune checkpoint inhibitor, wherein the oncolytic herpes simplex virus is a mutant of HSV-1 strain 17 or is HSV1716.

16. The kit of paragraph 14 or 15 wherein the immune checkpoint inhibitor is an inhibitor of at least one of CTLA4, PD-1, PD-L1, TIM-3 or LAG-3.

17. Products containing therapeutically effective amounts of (i) HSV1716, and (ii) an immune checkpoint inhibitor, for simultaneous or sequential use in a method of medical treatment, preferably treatment of cancer.

18. Products according to paragraph 17 wherein the immune checkpoint inhibitor is an inhibitor of at least one of CTLA4, PD-1, PD-L1, TIM-3 or LAG-3.

DESCRIPTION

T helper (Th) cells play an important role in the adaptive immune system, regulating the activity of other immune cells by releasing certain cytokines. They are essential in the activation and proliferation of cytotoxic T cells and in optimising the activity of macrophages. Mature Th cells express CD4 (i.e. are $CD4^+$ T cells). Proliferating Th cells differentiate from a Th0 state into effector T cells of two main subtypes: Type 1 (Th1) and Type 2 (Th2) (Kidd P. Altern Med Rev. 2003; 8(3):223-46; Sallusto et al., Trends in Immunology. Volume 19, Issue 12, p 568-574, 1 Dec. 1998).

Differentiation towards Th1 is primarily triggered by IL-12 and IL-2. The primary effector cytokine of the Th1 response is IFN-γ, although cytokines secreted by Th1 cells include Tumor Necrosis Factor (TNF-α), IFN-γ and interleukins (IL) 2, 12, and 18. IFN-γ promotes production of IL-12 from dendritic cells and macrophages which further promotes IFN-γ production in Th cells by a positive feedback mechanism. IFN-γ production also inhibits production of IL-4, and thereby inhibits the Th2 response. Th1 immunity is mainly effected through macrophages, $CD8^+$ T cells, IgG B cells and IFN-γ $CD4^+$ T cells. Th1 cytokines tend to produce pro-inflammatory cytokines such as IL-6.

Differentiation towards Th2 is primarily triggered by IL-4 and the effector cytokines of the Th2 response include IL-4, IL-5, IL-9, IL-10 and IL-13. Th2 immunity is mainly effected through eosinophils, basophils and mast cells, as well as B cells and IL-4/IL-5 $CD4^+$ T cells. IL-10 acts to suppress Th1 cell differentiation by inhibiting IL-2 and IFN-γ in Th cells and IL-12 in dendritic cells and macrophages.

Data presented herein from a trial in human patients shows that single dose non-intratumoral administration of oncolytic herpes simplex virus can be sufficient to induce an IFNγ response (e.g. FIGS. 1 and 22) but the response is not robustly translated into upregulation of IL-2 and IL-12 (FIGS. 5, 9 and 23). IFNγ is pleiotropic (Trincheri and Perussia., Immune interferon: a pleiotropic lymphokine with multiple effects. Immunology Today, Volume 6, Issue 4, 131-136), and upregulation of IFNγ alone, without induction of threshold levels of IL-2 and/or IL-12, is not a reliable indicator of induction of a robust or sustained Th1 response.

Administration of multiple doses of oncolytic herpes simplex virus is shown to further upregulate IFNγ and lead to upregulation of IL-2 and IL-12 (FIG. 23) and expansion of T cells associated with a Th1 response (FIG. 49). IL-2 and IL-12 upregulation leads to expansion of a Th1 cell population by a positive feedback mechanism (Busse et al., Competing feedback loops shape IL-2 signaling between helper and regulatory T lymphocytes in cellular microenvironments. PNAS 2010 107 (7) 3058-3063; Vignali and Kuchroo, IL-12 family cytokines: immunological playmakers. Nature Immunology 13, 722-728 (2012)) which is modulated by upregulated IL-10 (Taga and Tosato, IL-10 inhibits human T cell proliferation and IL-2 production. J Immunol. 1992 feb 15; 148(4):1143-8).

The data obtained (FIGS. 23 and 49) show that multiple dose administration of oncolytic herpes simplex virus leads to upregulated IFNγ, IL-2, IL-12, IL-10 in human subjects, and an appropriate T cell population, clearly indicating establishment of a sustained Th1 response.

The inventors have identified that administration of oncolytic herpes simplex virus to human patients having cancer induces a strong Th1 immune response. The response appears to mature and become sustained with time and be stronger in patients receiving more than one dose of virus. Oncolytic herpes simplex virus transfected into tumor cells will replicate in and selectively lyse the tumor cells bringing about tumor cell necrosis and the liberation of tumor antigens, which trigger a Th1 immune response. Indeed, the inventors have noted that oncolytic herpes simplex virus remodels the tumor microenvironment away from immunosuppression by directly interacting with tumor infiltrating immune cells.

Accordingly, human patients may be treated with an oncolytic herpes simplex virus in order to stimulate and establish a Th1 immune response.

Human patients treated with oncolytic herpes simplex virus are therefore also well-suited to treatment with an immune checkpoint inhibitor so as to provide either an enhanced treatment effect and/or to convert patients having no or sub-optimal response to immune checkpoint inhibitor therapy to become responders to such therapy.

Accordingly, human patients may be treated with an oncolytic herpes simplex virus in order to stimulate and establish a Th1 immune response thereby priming the subject for treatment with an immune checkpoint inhibitor.

Without wishing to be bound by theory of the invention, treatment with an oncolytic herpes simplex virus may be used to establish a Th1 immune response in the subject. Establishing a Th1 response may help increase the magnitude of tumor specific T cell responses. Induction of a Th1 response in a subject who is a non-responder or poor responder may convert the subject to a responder.

Having established a Th1 response treatment with an immune checkpoint inhibitor may increase the magnitude of tumor specific T cell responses as compared to treatment with an immune checkpoint inhibitor alone. In particular, the response of a subject to treatment with an immune checkpoint inhibitor may be improved by use of an oncolytic herpes simplex virus to establish a Th1 response. Subjects who are non-responders or poor responders to immune checkpoint inhibitor treatment may be converted to responders.

In general, treatment with an oncolytic herpes simplex virus (with or without immune checkpoint inhibitor) may enhance the systemic T-cell activation and the anti-tumor response to tumor antigens following the lytic replication of oncolytic herpes simplex virus in the cells of the cancer. This may lead to enhanced destruction of tumors to which the virus has been administered, e.g. by direct injection, but may also enhance the destruction of tumors to which the virus has not been administered and/or are distant to the site of administration, e.g. secondary/metastatic tumors. This may improve the rate of overall tumor response and duration of response. Overall, these effects may provide an extension in overall survival, particularly when compared to treatment using an immune checkpoint inhibitor alone.

The inventors have noted that mice that receiving oncolytic herpes simplex virus showed more T cell recruitment to the tumor, and displayed higher immune inflammatory responses and a less immunosuppressive microenvironment, as measured by increased proportions of CD4+ and CD8+ T cells relative to CD4+/CD25+/Fox3P+ Treg cells and immunosuppressive cytokines.

The inventors have noted that mice that receive combination therapy with oncolytic herpes simplex virus and an immune checkpoint inhibitor showed more T cell recruitment to the tumor, and displayed higher immune inflammatory responses and a less immunosuppressive microenvironment, as measured by increased proportions of CD4+ and CD8+ T cells relative to CD4+/CD25+/Fox3P+ Treg cells and immunosuppressive cytokines. The combination therapy did not result in more NK, NKT or B cell recruitment or affect in vivo virus activity but induced more inflammatory responses with less immune regulatory/suppressive responses.

The inventors have identified that induction of a Th1 response through administration of an effective amount of oncolytic herpes simplex virus is effective to trigger an anti-tumor Th1 response in the subject. They have also identified that the anti-tumor Th1 response has a memory effect, and may be used to vaccinate the subject against relapse of the cancer at both primary and distal sites Administration of Oncolytic Herpes Simplex Virus Administration of oncolytic herpes simplex virus is preferably for a period of time sufficient to induce or elicit a durable Th1 response in the subject. The Th1 response is preferably an anti-tumor Th1 response.

This may involve administration at regular intervals, e.g. weekly or fortnightly, of doses of oncolytic herpes simplex virus sufficient to induce a sustained Th1 response over a period of time. For example, doses may be given at regular, defined, intervals over a period of one of at least 1, 2, 3, 4, 5, 6, 7, 8, weeks or 1, 2, 3, 4, 5 or 6 months.

As such, multiple doses of oncolytic herpes simplex virus may be administered. For example, 1, 2, 3, 4, 5, 6, 7, 8, 9, 10 or more doses of oncolytic herpes simplex virus may be administered to a subject as part of a course of treatment designed to induce or elicit a Th1 response. In some preferred embodiments one of at least 2, 3, or 4 doses of oncolytic herpes simplex virus are administered to the subject, preferably at regular intervals (e.g. weekly), in order to establish a Th1 response in the subject. Establishing the Th1 response may prime them for treatment with an immune checkpoint inhibitor.

Doses of oncolytic herpes simplex virus may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days). The dose of oncolytic herpes simplex virus given at each dosing point may be the same, but this is not essential. For example, it may be appropriate to give a higher priming dose at the first, second and/or third dosing points.

Administration of oncolytic herpes simplex virus may be of one or more treatment cycles, e.g. 1, 2, 3, 4, 5, 6, 7, 8, 9, 10 or more treatment cycles. A subject receiving multiple treatment cycles may be given subsequent treatment cycles consecutively, without a break from treatment, or may separate all or selected treatment cycles by a break from treatment, e.g. a break of 1, 2, 3, 4, 5, 6, 7, 8 or 9 days or about 1, 2, 3, or 4 weeks.

In some embodiments a treatment cycle may comprise, or consist of, 4 doses of oncolytic herpes simplex virus, one dose per week over a period of 4 weeks. In some embodiments a treatment cycle may comprise, or consist of, 8 doses of oncolytic herpes simplex virus, one dose per week over a period of 8 weeks. Weekly doses may be separated by 7±1 or 7±2 days. For example, weekly doses may be given on days 1, 8, 15 and 22.

In some embodiments a treatment cycle may comprise, or consist of, 4 doses of oncolytic herpes simplex virus, two doses per week over a period of 2 weeks. In some embodiments a treatment cycle may comprise, or consist of, 8 doses of oncolytic herpes simplex virus, two doses per week over a period of 4 weeks. Twice weekly doses may be separated by 4±1 or 4±2 days. For example, weekly doses may be given on days 1, 5, 8, 13 or 1, 5, 8, 12.

Subjects may receive the same dosage at each administration within a given treatment cycle, e.g. a dosage of $1\times10^7$ iu or $1\times10^8$ iu, or between $1\times10^7$ iu and $1\times10^8$ iu. In some embodiments the first 1, 2 or 3 treatment cycles may comprise administration of a lower dosage amount at each administration, e.g. $1\times10^7$ iu, and later treatment cycles may comprise administration of a higher dosage amount at each administration, e.g. $1\times10^8$ iu.

Administration of oncolytic herpes simplex virus may be by infusion to the blood (intravenous or intra-arterial) and subjects will preferably attend clinic on the scheduled administration days for administration of oncolytic herpes simplex virus. Administration of oncolytic herpes simplex virus may continue until development of severe toxicity or withdrawal of consent.

A tumour biopsy may be taken in the period commencing 14 days before the first dose of oncolytic herpes simplex virus (Day 1). A tumour biopsy or surgical resection sample may be taken after completion of a cycle of treatment, e.g. within 14 days of the last dose of oncolytic herpes simplex virus in a given treatment cycle. Samples obtained from tumour biopsy or surgical resection may be used to determine the presence and/or maintenance of a Th1 response.

Blood or serum samples may be taken at the stage of initial subject assessment (before treatment with oncolytic herpes simplex virus), and during a or each treatment cycle, e.g. on days 1, 8, 15, 22, for weekly administration, days 1, 5, 8, 13, or days 1, 5, 8, 12 for twice weekly administration. Blood or serum samples may be used to determine the presence and/or maintenance of a Th1 response.

Once a Th1 response, preferably a sustained Th1 response, has been induced the subject may continue with dosing of oncolytic herpes simplex virus on the same dosing schedule in order to maintain the response. Alternatively, dosing frequency may be reduced and the subject may receive either no further doses of oncolytic herpes simplex virus, e.g. in cases where the Th1 response is self-sustaining following induction, or the status of the Th1 response in the subject may be monitored and the subject may be given booster administrations as and when considered appropriate, e.g. by a medical practitioner, in order to maintain the sustained Th1 response.

Suitable dosage amounts of oncolytic herpes simplex virus may be in the range $10^6$ to $10^9$ iu or $2\times10^6$ to $10^9$ iu. Doses may be in a range selected from the group consisting of: $2\times10^6$ to $9\times10^6$ iu, $2\times10^6$ to $5\times10^6$ iu, $5\times10^6$ to $9\times10^6$ iu, $2\times10^6$ to $1\times10^7$ iu, $2\times10^6$ to $5\times10^7$ iu, $2\times10^6$ to $1\times10^8$ iu, $2\times10^6$ to $5\times10^8$ iu, $2\times10^6$ to $1\times10^9$ iu, $5\times10^6$ to $1\times10^7$ iu, $5\times10^6$ to $5\times10^7$ iu, $5\times10^6$ to $1\times10^8$ iu, $5\times10^6$ to $5\times10^8$ iu, $5\times10^6$ to $1\times10^9$ iu, $5\times10^6$ to $5\times10^9$ iu, $1\times10^7$ to $9\times10^7$ iu, $1\times10^7$ to $5\times10^7$ iu, $1\times10^8$ to $9\times10^8$ iu, $1\times10^8$ to $5\times10^8$ iu. In some embodiments suitable doses may be in the range $2\times10^6$ to $9\times10^6$ iu, $1\times10^7$ to $9\times10^7$ iu, or $1\times10^8$ to $9\times10^8$ iu. In some embodiments suitable doses may be about $1\times10^7$ iu or about $1\times10^8$ iu, or in the range about $1\times10^7$ iu to about $1\times10^8$ iu. Dosage figures may optionally be +/− half a log value.

The term 'infectious units' is used to refer to virus concentrations derived using the TCID50 method and 'plaque forming units (pfus)' to refer to plaque-based assay results. As 1 iu will form a single plaque in a titration assay, 1 iu is equivalent to 1 pfu.

In general, administration is preferably in a "effective amount", this being sufficient to induce a Th1 response in the individual and/or for the virus to have an independent treatment effect on the cancer. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Treatment with oncolytic herpes simplex virus is preferably for a period of time suitable, or sufficient, to induce or elicit a Th1 immune response in the subject.

Administration of oncolytic herpes simplex virus may preferably be carried out for a period of time, e.g. prior to treatment with an immune checkpoint inhibitor, in which period the subject receives oncolytic herpes simplex virus but does not receive an immune checkpoint inhibitor. Treatment is preferably for a period of time suitable, or sufficient, to induce or elicit a Th1 immune response in the subject. This may be referred to as "pre-treatment" with oncolytic herpes simplex virus.

In some preferred embodiments pre-treatment may involve a period of time in which the subject is administered oncolytic herpes simplex virus but is not administered an immune checkpoint inhibitor (called "oncolytic herpes simplex virus monotherapy" herein). The period of oncolytic herpes simplex virus monotherapy may be sufficient to induce or elicit a Th1 response in the subject. During a period of oncolytic herpes simplex virus monotherapy the subject may also receive treatment in the form of simultaneous, sequential or separate administration of other chemotherapy or radiation therapy, e.g. which may be part of the standard of care for the cancer being treated, but in that time period the patient will not receive a therapeutically effective dose of an immune checkpoint inhibitor.

As such, methods according to the present invention may comprise administration of an oncolytic herpes simplex virus for a period of time in which the subject receives oncolytic herpes simplex virus but does not receive an immune checkpoint inhibitor. The period of time is preferably suitable, or sufficient, to induce a Th1 response in the subject.

During or following the pre-treatment a determination may be made as to whether a Th1 response has been induced or elicited in the subject and/or a selection of subject(s) in which a Th1 response has been induced or elicited may be made. Selected subject(s) may be considered suitable for treatment with an immune checkpoint inhibitor.

A subject may then begin treatment with an immune checkpoint inhibitor. That is, the method may then further comprises the administration of an immune checkpoint inhibitor to the subject. Treatment with an immune checkpoint inhibitor is not mandatory and in some embodiments subjects will not receive such treatment.

Accordingly, at a selected time point the period of pre-treatment may end and the subject may then be administered an immune checkpoint inhibitor. Optionally the subject will continue to be administered oncolytic herpes simplex virus simultaneously, sequentially or separately such that the subject receives co-therapy with immune checkpoint inhibitor and oncolytic herpes simplex virus. The subject may also receive, or continue to receive, treatment in the form of simultaneous, sequential or separate administration of other chemotherapy or radiation therapy, e.g. which may be part of the standard of care for the cancer being treated.

For example, pre-treatment may occur for one of at least 1, 2, 3, 4, or 5 weeks in which the subject receives oncolytic herpes simplex virus but does not receive an immune checkpoint inhibitor. Preferably the period of time is sufficient to induce or elicit a Th1 response in the subject. By way of example, a subject may receive oncolytic herpes simplex virus monotherapy in the form of weekly doses of oncolytic herpes simplex virus for one of at least 1, 2, 3, 4, 5, 6, 7, 8, weeks or 1, 2, 3, 4, 5 or 6 months.

In other embodiments a subject may receive oncolytic herpes simplex virus monotherapy as described above and may discontinue treatment with oncolytic herpes simplex virus and begin receiving treatment with an immune checkpoint inhibitor. In such embodiments there may be no day on which a subject is receiving co-therapy, i.e. no day on which an ongoing scheduled programme of treatment with oncolytic herpes simplex virus and immune checkpoint inhibitor overlaps.

In other embodiments there may a substantial overlap of treatment with oncolytic herpes simplex virus. In one arrangement, co-therapy with oncolytic herpes simplex virus and immune checkpoint inhibitor may commence at the start of treatment, or during a period in which the subject is receiving an oncolytic herpes simplex virus in order to induce or elicit a Th1 response, preferably a sustained Th1 response. In other arrangements a short period of oncolytic herpes simplex virus monotherapy may be provided, not necessarily suitable or sufficient to induce or elicit a Th1 response, preferably a sustained Th1 response, after which the subject begins to also receive treatment with an immune checkpoint inhibitor, i.e. co-therapy. During co-therapy the oncolytic herpes simplex virus and immune checkpoint inhibitor may be administered on the same day or on different days.

Co-therapy may comprises simultaneously or sequential administration of oncolytic herpes simplex virus and immune checkpoint inhibitor.

Simultaneous administration refers to administration of the oncolytic herpes simplex virus and immune checkpoint inhibitor together, for example as a pharmaceutical composition containing both agents, or immediately after each other and optionally via the same route of administration, e.g. to the same artery, vein or other blood vessel.

Sequential administration refers to administration of one of the oncolytic herpes simplex virus or immune checkpoint inhibitor followed after a given time interval by separate administration of the other agent. It is not required that the two agents are administered by the same route, although this is the case in some embodiments. The time interval may be any time interval.

Whilst simultaneous or sequential administration may be intended such that both the oncolytic herpes simplex virus and immune checkpoint inhibitor are delivered to the same tumor tissue to effect treatment it is not essential for both agents to be present in the tumor tissue in active form at the same time.

However, in some embodiments of sequential administration the time interval is selected such that the oncolytic herpes simplex virus and immune checkpoint inhibitor are expected to be present in the tumor tissue in active form at the same time, thereby allowing for a combined, additive or synergistic effect of the two agents in treating the tumor. In such embodiments the time interval selected may be any one of 5 minutes or less, 10 minutes or less, 15 minutes or less, 20 minutes or less, 25 minutes or less, 30 minutes or less, 45 minutes or less, 60 minutes or less, 90 minutes or less, 120 minutes or less, 180 minutes or less, 240 minutes or less, 300 minutes or less, 360 minutes or less, or 720 minutes or less, or 1 day or less, or 2 days or less.

A subject may receive oncolytic herpes simplex virus before treatment with the immune checkpoint inhibitor that is intended to take advantage of the Th1 response which the oncolytic herpes simplex virus may induce or elicit when providing a treatment effect.

Where co-therapy with an oncolytic herpes virus occurs it may continue for as long as desired or prescribed. In some embodiments, treatment with oncolytic herpes simplex virus may be discontinued in favour of continued treatment with the immune checkpoint inhibitor.

Doses of immune checkpoint inhibitor may also be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

During co-therapy the subject may also receive, or continue to receive, treatment in the form of simultaneous, sequential or separate administration of other chemotherapy or radiation therapy, e.g. which may be part of the standard of care for the cancer being treated.

A Th1 response is preferably a sustained Th1 response. By "sustained Th1 response" we mean that the level of one or more relevant cytokines (e.g. IL-2 and/or IL-12 and/or IFN-γ) and/or relevant T cell population (e.g. Th1 cells) is upregulated for more than 7 days, and preferably for one of at least 2, 3, 4, 5, 6, 7, or 8 weeks, or for one of at least 1, 2, 3, 4, 5, or 6 months.

Detecting a Th1 Immune Response

A Th1 immune response may be characterised by upregulation of one or more relevant cytokines selected from the group consisting of IFN-γ, IL-2, IL-12, IP-10, MIG, TNF-α, IL-18, IL-27, TNF-β. In some embodiments a Th1 response may be characterised by upregulation of IFN-γ, IL-2, or IL-12.

Not all subjects respond to administration of oncolytic HSV by induction of a Th1 response and subjects may therefore be monitored to determine their response to treatment with the oncolytic HSV. Subjects who respond may continue treatment with oncolytic HSV at a dose and/or dosage regime designed to maintain the sustained Th1 response. Subjects who do not respond to treatment by generation of a Th1 response may discontinue treatment with oncolytic HSV, or may transition to combination treatment with oncolytic HSV and one or more additional chemotherapeutic agents.

Accordingly, the presence of a Th1 response may be determined by measuring the level of a Th1 cytokine in a sample obtained from a subject.

In addition to the cytokines secreted by Th1 cells, the expression of specific cell surface proteins or receptors, including IL-12 R beta 2, IL-27 R alpha/WSX-1, IFN-gamma R2, CCR5, and CXCR3, can be used to distinguish Th1 cells from other T cell subtypes. T cells associated with a Th1 response can also be partially characterised as $CD4^+$ or $CD8^+$. Accordingly, the presence of a Th1 response may also be determined or partially determined by measuring the expression of Th1 cell surface proteins or receptors by T cells in a sample obtained from a subject and/or by measuring the proportion of T cells that are $CD4^+$ or $CD8^+$ in a sample obtained from a subject.

In some preferred embodiments a Th1 response may be characterised by upregulation of IFN-γ. In some preferred embodiments a Th1 response may be characterised by upregulation of IL-2. In some preferred embodiments a Th1 response may be characterised by upregulation of IL-12. In some preferred embodiments a Th1 response may be characterised by upregulation of IFN-γ and determination of T cell $CD8^+$ status. In some preferred embodiments a Th1 response may be characterised by upregulation of IL-2 and determination of T cell $CD8^+$ status. In some preferred embodiments a Th1 response may be characterised by upregulation of IL-12 and determination of T cell $CD8^+$ status. In some preferred embodiments a Th1 response may be characterised by upregulation of IFN-γ and one or both of IL-2 and IL-12, and optionally determination of T cell CD8+ status. In some preferred embodiments a Th1 response may be characterised by upregulation of IL-2 and one or both of IFN-γ and IL-12, and optionally determination of T cell CD8+ status. In some preferred embodiments a Th1 response may be characterised by upregulation of IL-12 and one or both of IFN-γ and IL-2, and optionally determination of T cell CD8+ status. In some preferred embodiments a Th1 response may be characterised by upregulation of IL-2 and/or IL-12.

The detection and characterisation of a Th1 immune response is a routine procedure for one of ordinary skill in the art. Numerous cytokine and cell detection assays are available including single and multiplexed ELISAs, reverse-transcription-PCR, Taqman real-time PCR, immunohistochemistry and flow cytometry (e.g. see Whiteside T L. Cytokine assays. Biotechniques 2002; Suppl: 4-8, 10, 12-5; Pala P, Hussell T, Openshaw P J. Flow cytometric measurement of intracellular cytokines. J Immunol Methods 2000; 243:107-24; Jason J, Lamed J. Single-cell cytokine profiles in normal humans: comparison of flow cytometric reagents and stimulation protocols. J Immunol Methods 1997; 207: 13-22; Farrell A M et al. A rapid flow cytometric assay to detect CD4+ and CD8+T-helper (Th) 0, Th1 and Th2 cells in whole blood and its application to study cytokine levels in atopic dermatitis before and after cyclosporin therapy. Br J Dermatol. 2001 January; 144(1):24-33).

The induction of a Th1 response and maintenance of the response over time may therefore be monitored at desired intervals by analysing the level of cytokine expression in a sample taken from a subject. Such monitoring may be conducted, daily, weekly, fortnightly, monthly or yearly as desired and/or consider appropriate by a medical practitioner.

In some embodiments detection of a Th1 response involves detection of an upregulation of a Th1 cell population or of Th1 cytokines.

Upregulation may be determined by comparing the level of a cell population or cytokine before and after a treatment, e.g. before and then after a period of treatment (optionally pre-treatment) with an oncolytic herpes simplex virus. Levels of a cell population or of a cytokine may be quantitated for absolute comparison, or relative comparisons may be made.

In some embodiments upregulation may be considered to be present when the level of a cell population or cytokine in the test sample is at least 1.1 times that in the control sample (e.g. a sample obtained before treatment with oncolytic herpes simplex virus). More preferably, the level may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, at least 10.0, at least 11.0, at least 12.0, at least 13.0, at least 14.0, or at least 15.0 times that in the control sample.

Detection of a Th1 response may be further confirmed by detection of an anti-tumor IgG response. This may be determined, for example, by immunoassay to detect the presence of IgG in a sample from a subject having received treatment with oncolytic herpes simplex virus. Comparison may be made to the absence of such a response in a patient not having received treatment with oncolytic herpes simplex virus.

In addition to detection of a Th1 response, the presence of HSV DNA may be detected in a sample. HSV DNA may be detected by routine techniques such as qPCR or Real-Time PCR (e.g. see Kessler et al., J Clin Microbiol. 2000 July; 38(7):2638-2642; Pandori et al BMC Infectious Diseases 2006 6:104; Hong et al., BioMed Research International Vol 2014 (2014) Article ID 261947, 5 pages).

A sample may be obtained from a subject. Samples may be obtained before, during and/or after treatment with an oncolytic herpes simplex virus. A sample obtained before treatment has commenced may provide reference values for cytokine levels, cell surface proteins or receptors or proportion of CD4+ or CD8+ T cells which may allow for comparison with levels determined during or after treatment, the comparison enabling a determination of whether a Th1 response has been induced or elicited in the subject.

A sample may be taken derived from any tissue, e.g. tumor tissue, or bodily fluid, and may be processed to isolate a cell population of interest, e.g. white blood cells, lymphocytes or T cells.

A sample may comprise or may be derived from: a quantity of blood; a quantity of serum derived from the individual's blood which may comprise the fluid portion of the blood obtained after removal of the fibrin clot and blood cells; other bodily fluids, pleural fluid, effusion fluid, ascites, or a fluid produced by a cancer.

In preferred arrangements the sample is taken from a bodily fluid, more preferably one that circulates through the body. Accordingly, the sample may be a blood sample or lymph sample.

In some embodiments the sample is a blood sample or blood-derived sample. The blood derived sample may be a selected fraction of a patient's blood, e.g. a selected cell-containing fraction or a plasma or serum fraction. A selected cell-containing fraction may contain cell types of interest which may include white blood cells (WBC), lymphocytes, peripheral blood mononuclear cells (PBC) and/or granulocytes, and/or red blood cells (RBC).

In some embodiments the sample is a biopsy, or is derived from a biopsy. In some embodiments the sample may be obtained during surgical resection of a tumor. Solid tumors are particularly suitable for obtaining samples by biopsy or during surgical resection. Solid tumors are particularly suitable for obtaining samples by biopsy or during surgical resection.

Subjects selected for treatment with herpes simplex virus may be indicated for surgical removal of tumor tissue (referred to herein as 'tumor resection'). For example, they may have a cancer considered, by a medical practitioner, operable to remove some or all of the tumor tissue. Treatment with herpes simplex virus may commence prior to tumor resection.

Tumor tissue removed during tumor resection may be analysed to determine whether herpes simplex virus has reached the tumor, e.g. by detecting in vitro the presence of HSV DNA in excised tumor tissue and/or the expression of HSV antigens by immunohistochemistry and/or to determine whether a Th1 response is present in the cancer, e.g. by detecting in vitro the presence of a Th1 response in excised tumor tissue.

In some embodiments the sample is a sample of effusion fluid, e.g. pleural fluid or ascites. Effusion fluid refers to an excess of fluid produced by a subject in direct or indirect response to the presence of a cancer in the subject. Effusion fluid may collect in a body cavity such that accumulation of effusion fluid may occur where the rate of production of the effusion fluid exceeds the rate of reabsorption. Pleural effusions (sometimes called malignant pleural effusions) lead to accumulation of fluid in the pleural cavity and occur in some lung cancers, e.g. mesothelioma. Effusion fluid collecting in the peritoneal cavity is commonly referred to as ascites, and can be a symptom of a number of types of cancer including cancer of the breast, lung, colon, stomach, pancreas, ovary, endometrium as well as lymphoma. Pericardial effusion is the abnormal accumulation of fluid in the pericardial cavity. The effusion fluid is preferably exudative.

Effusion fluid can be drained from a respective body cavity by well-known aseptic procedures (e.g. see Warren et al. Ann Thorac Surg 2008; 85:1049-55; Warren et al. European Journal of Cardio-thoracic Surgery 33 (2008) 89-94). In some instances, a tube or catheter is inserted in the body cavity in order to drain effusion fluid. Drainage of effusion fluid is a common part of the diagnosis, treatment and management of many forms of cancer. Drainage of effusion fluid provides a means of obtaining a sample of a subject's effusion fluid for analysis.

Oncolytic Herpes Simplex Virus

An oncolytic virus is a virus that will lyse cancer cells (oncolysis), preferably in a preferential or selective manner. Viruses that selectively replicate in dividing cells over non-dividing cells are often oncolytic. Oncolytic viruses are well known in the art and are reviewed in Molecular Therapy Vol. 18 No. 2 Feb. 2010 pg 233-234.

The herpes simplex virus (HSV) genome comprises two covalently linked segments, designated long (L) and short (S). Each segment contains a unique sequence flanked by a pair of inverted terminal repeat sequences. The long repeat (RL or $R_L$) and the short repeat (RS or $R_S$) are distinct.

The HSV ICP34.5 (also called γ34.5) gene, which has been extensively studied, has been sequenced in HSV-1 strains F and syn17+ and in HSV-2 strain HG52. One copy of the ICP34.5 gene is located within each of the RL repeat regions. Mutants inactivating one or both copies of the ICP34.5 gene are known to lack neurovirulence, i.e. be avirulent/non-neurovirulent (non-neurovirulence is defined by the ability to introduce a high titre of virus (approx $10^6$ plaque forming units (pfu)) to an animal or patient without causing a lethal encephalitis such that the $LD_{50}$ in animals, e.g. mice, or human patients is in the approximate range of $\geq 10^6$ pfu), and be oncolytic.

Preferred oncolytic Herpes Simplex Virus (oHSV) are replication-competent virus, being replication-competent at least in the target tumor/cancer cells.

Oncolytic HSV that may be used in the present invention include HSV in which one or both of the γ34.5 (also called ICP34.5) genes are modified (e.g. by mutation which may be a deletion, insertion, addition or substitution) such that the respective gene is incapable of expressing, e.g. encoding, a functional ICP34.5 protein. Preferably, in HSV according to the invention both copies of the γ34.5 gene are modified such that the modified HSV is not capable of expressing, e.g. producing, a functional ICP34.5 protein.

In some embodiments the oncolytic herpes simplex virus may be an ICP34.5 null mutant where all copies of the ICP34.5 gene present in the herpes simplex virus genome (two copies are normally present) are disrupted such that the herpes simplex virus is incapable of producing a functional ICP34.5 gene product. In other embodiments the oncolytic herpes simplex virus may lack at least one expressible ICP34.5 gene. In some embodiments the herpes simplex virus may lack only one expressible ICP34.5 gene. In other embodiments the herpes simplex virus may lack both expressible ICP34.5 genes. In still other embodiments each ICP34.5 gene present in the herpes simplex virus may not be expressible. Lack of an expressible ICP34.5 gene means, for example, that expression of the ICP34.5 gene does not result in a functional ICP34.5 gene product.

Oncolytic herpes simplex virus may be derived from any HSV including any laboratory strain or clinical isolate (non-laboratory strain) of HSV. In some preferred embodiments the HSV is a mutant of HSV-1 or HSV-2. Alternatively the HSV may be an intertypic recombinant of HSV-1 and HSV-2. The mutant may be of one of laboratory strains HSV-1 strain 17, HSV-1 strain F or HSV-2 strain HG52. The mutant may be of the non-laboratory strain JS-1. Preferably the mutant is a mutant of HSV-1 strain 17. The herpes simplex virus may be one of HSV-1 strain 17 mutant 1716, HSV-1 strain F mutant R3616, HSV-1 strain F mutant G207, HSV-1 mutant NV1020, or a further mutant thereof in which the HSV genome contains additional mutations and/or one or more heterologous nucleotide sequences. Additional mutations may include disabling mutations, which may affect the virulence of the virus or its ability to replicate. For example, mutations may be made in any one or more of ICP6, ICP0, ICP4, ICP27. Preferably, a mutation in one of these genes (optionally in both copies of the gene where appropriate) leads to an inability (or reduction of the ability) of the HSV to express the corresponding functional polypeptide. By way of example, the additional mutation of the HSV genome may be accomplished by addition, deletion, insertion or substitution of nucleotides. In some embodiments the HSV genome does not have a mutation in ICP6, or in ICP0, ICP4, ICP27.

A number of oncolytic herpes simplex viruses are known in the art. Examples include HSV1716, R3616 (e.g. see Chou & Roizman, Proc. Natl. Acad. Sci. Vol. 89, pp. 3266-3270, April 1992), G207 (Toda et al, Human Gene Therapy 9:2177-2185, Oct. 10, 1995), NV1020 (Geevarghese et al, Human Gene Therapy 2010 September; 21(9): 1119-28), RE6 (Thompson et al, Virology 131, 171-179 (1983)), and Oncovex™ (Simpson et al, Cancer Res 2006; 66:(9) 4835-4842 May 1, 2006; Liu et al, Gene Therapy (2003): 10, 292-303), dlsptk, hrR3, R4009, MGH-1, MGH-2, G47Δ, Myb34.5, DF3γ34.5, HF10, NV1042, RAMBO, rQNestin34.5, R5111, R-LM113, CEAICP4, CEAγ34.5, DF3γ34.5, KeM34.5 (Manservigi et al, The Open Virology Journal 2010; 4:123-156), rRp450, M032 (Campadelli-Fiume et al, Rev Med. Virol 2011; 21:213-226), Bacol (Fu et al, Int. J. Cancer 2011; 129(6):1503-10) and M032 and C134 (Cassady et al, The Open Virology Journal 2010; 4:103-108).

In some preferred embodiments the herpes simplex virus is HSV-1 strain 17 mutant 1716 (HSV1716). HSV 1716 is an oncolytic, non-neurovirulent HSV and is described in EP 0571410, WO 92/13943, Brown et al (Journal of General Virology (1994), 75, 2367-2377) and MacLean et al (Journal of General Virology (1991), 72, 631-639). HSV 1716 has been deposited on 28 Jan. 1992 at the European Collection of Animal Cell Cultures, Vaccine Research and Production Laboratories, Public Health Laboratory Services, Porton Down, Salisbury, Wiltshire, SP4 0JG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

In some embodiments the herpes simplex virus is a mutant of HSV-1 strain 17 modified such that both ICP34.5 genes do not express a functional gene product, e.g. by mutation (e.g. insertion, deletion, addition, substitution) of the ICP34.5 gene, but otherwise resembling or substantially resembling the genome of the wild type parent virus HSV-1 strain 17+. That is, the virus may be a variant of HSV1716, having a genome mutated so as to inactivate both copies of the ICP34.5 gene of HSV-1 strain 17+ but not otherwise altered to insert or delete/modify other protein coding sequences.

In some embodiments the genome of an oncolytic Herpes Simplex Virus according to the present invention may be further modified to contain nucleic acid encoding at least one copy of a polypeptide that is heterologous to the virus (i.e. is not normally found in wild type virus) such that the polypeptide can be expressed from the nucleic acid. As such, the oncolytic virus may also be an expression vector from which the polypeptide may be expressed. Examples of such viruses are described in WO2005/049846 and WO2005/049845.

In order to effect expression of the polypeptide, nucleic acid encoding the polypeptide is preferably operably linked to a regulatory sequence, e.g. a promoter, capable of effecting transcription of the nucleic acid encoding the polypeptide. A regulatory sequence (e.g. promoter) that is operably linked to a nucleotide sequence may be located adjacent to that sequence or in close proximity such that the regulatory sequence can effect and/or control expression of a product of the nucleotide sequence. The encoded product of the nucleotide sequence may therefore be expressible from that regulatory sequence.

In some preferred embodiments, the oncolytic Herpes Simplex Virus is not modified to contain nucleic acid encoding at least one copy of a polypeptide (or other nucleic acid encoded product) that is heterologous to the virus. That is the virus is not an expression vector from which a heterologous polypeptide or other nucleic acid encoded product may be expressed. Such oHSV are not suitable for, or useful in, gene therapy methods and the method of medical treatment for which they are employed may optionally be one that does not involve gene therapy.

In some embodiments the genome of an oncolytic Herpes Simplex Virus according to the present invention does not encode (or is not further modified to contain nucleic acid encoding) a cytokine or chemokine, e.g. a mammalian or human cytokine or chemokine. For example, the genome of an oncolytic Herpes Simplex Virus according to the present invention does not encode an interleukin, e.g. IL-2 and/or IL-12, an interferon, e.g. IFN-γ, a tumor necrosis factor, a colony stimulating factor (e.g. GM-CSF, G-CSF), an immune modulator, a member of the CC family, e.g. CCL5, a member of the CXC family or a member of the CXC family.

In some embodiments the oncolytic herpes simplex virus has an intact ICP0 gene, capable of expressing functional ICP0. In some embodiments the oncolytic herpes simplex virus has an intact ICP27 gene, capable of expressing functional ICP27. In some embodiments the oncolytic herpes simplex virus has an intact vhs gene, capable of expressing functional vhs.

In some embodiments the oncolytic herpes simplex virus has an intact ICP47 gene, capable of expressing functional ICP47. In some embodiments the oncolytic herpes simplex virus has an intact ICP6 gene, capable of expressing functional ICP6.

Optionally, in some embodiments the oncolytic herpes simplex virus does not encode or express (granulocyte macrophage colony stimulating factor) GMCSF.

Optionally, in some embodiments the oncolytic herpes simplex virus is not a herpes simplex virus that lacks functional ICP34.5 genes and lacks a functional ICP47 gene and comprises a gene encoding human GM-CSF.

In some optional embodiments the oncolytic herpes simplex virus is not Talimogene laherparepvec, HSV-1 [strain JS1] ICP34.5-/ICP47-/hGM-CSF also known as OncoVEX GM-CSF (Lui et al., Gene Therapy, 10:292-303, 2003; U.S. Pat. Nos. 7,223,593 and 7,537,924)]. In talimogene laherparepvec, the HSV-1 viral genes encoding ICP34.5 are functionally deleted, the ICP47 is functionally deleted, the coding sequence for human GM-CSF is inserted into the viral genome such that it replaces nearly all of the ICP34.5 gene and the HSV thymidine kinase (TK) gene remains intact.

In some optional embodiments the herpes simplex virus is not a herpes simplex virus that lacks only one of the two functional copies of the $\gamma_1 34.5$ gene. For example, in some optional embodiments the herpes simplex virus is not NV1020.

Oncolytic herpes simplex viruses may be formulated as medicaments and pharmaceutical compositions for clinical use and in such formulations may be combined with a pharmaceutically acceptable carrier, diluent or adjuvant. The composition may be formulated for topical, parenteral, systemic, intracavitary, intravenous, intra-arterial, intramuscular, intrathecal, intraocular, intratumoral, subcutaneous, oral or transdermal routes of administration which may include injection. Suitable formulations may comprise the virus in a sterile or isotonic medium. Medicaments and pharmaceutical compositions may be formulated in fluid (including gel) or solid (e.g. tablet) form. Fluid formulations may be formulated for administration by injection or via catheter to a selected region of the human or animal body.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Targeting therapies may be used to deliver the oncolytic virus to certain types of cell, e.g. by the use of targeting systems such as antibody or cell specific ligands. Targeting may be desirable for a variety of reasons; for example if the virus is unacceptably toxic in high dose, or if it would otherwise require too high a dosage, or if it would not otherwise be able to enter the target cells.

HSV capable of targeting cells and tissues are described in (PCT/GB2003/000603; WO 03/068809), hereby incorporated in its entirety by reference.

An oncolytic virus may be administered alone or in combination with other treatments, either simultaneously or sequentially dependent upon the condition to be treated. Such other treatments may include chemotherapy (including either systemic treatment with a chemotherapeutic agent or targeted therapy using small molecule or biological molecule (e.g. antibody) based agents that target key pathways in tumor development, maintenance or progression) or radiotherapy provided to the subject as a standard of care for treatment of the cancer.

In addition to direct action of oncolytic herpes simplex virus (oHSV) on tumors, there is growing evidence that the host immune response plays an important role in establishing the efficacy of the anti-tumor response through innate immune effectors, adaptive antiviral immune responses and adaptive antitumor immune responses (e.g. see Prestwich et al., Oncolytic viruses: a novel form of immunotherapy. Expert Rev Anticancer Ther. October 2008; 8(10): 1581-1588).

Several studies have shown that oHSV is capable of inducing an anti-tumor immune response. This can manifest as tumor growth reduction in lesions treated with oHSV and in untreated lesions in the same animal, efficacy of oHSV requiring an intact immune response, induction of anti-tumor cytokine response, reversal of tumor immune dysfunction and facilitation of tumor antigen presentation. Induction of an anti-tumor immune response can reduce establishment of metastases, or contribute to their elimination, and protect from re-occurrence of tumor.

For example, in Benencia et al., ((2008) Herpes virus oncolytic therapy reverses tumor immune dysfunction and facilitates tumor antigen presentation. Cancer Biol. Ther. 7, 1194-1205) growth reduction in treated and untreated lesions was reported. In Miller and Fraser ((2003) Requirement of an integrated immune response for successful neuroattenuated HSV-1 therapy in an intracranial metastatic melanoma model. Mol. Ther. 7(6):741-747) efficacy of HSV176 required an intact immune response which was mediated by a tumor-specific proliferative T cell response.

Immune Checkpoint Proteins and Inhibitors

The term "immune checkpoint inhibitor" refers to molecules that totally or partially reduce, inhibit, interfere with or modulate one or more immune checkpoint proteins. An inhibitor may inhibit or block the interaction of an immune checkpoint protein with one of its ligands or receptors.

Immune checkpoint proteins negatively regulate T-cell activation or function. Numerous immune checkpoint proteins are known, such as CTLA-4 (Cytotoxic T-Lymphocyte-Associated protein 4) and its ligands CD80 and CD86; and PD-1 (Programmed Death 1) with its ligands PD-L1 and PD-L2 (Pardoll, Nature Reviews Cancer 12: 252-264, 2012), TIM-3 (T-cell Immunoglobulin domain and Mucin domain 3), LAG-3 (Lymphocyte Activation Gene-3), BTLA (CD272 or B and T Lymphocyte Attenuator), KIR (Killer-cell Immunoglobulin-like Receptor), VISTA (V-domain immunoglobulin suppressor of T-cell activation), and A2aR (Adenosine A2A receptor). These proteins are responsible for down-regulating T-cell responses. Immune checkpoint proteins regulate and maintain self-tolerance and the duration and amplitude of physiological immune responses. Immune checkpoint inhibitors include antibodies and small molecule inhibitors.

Cytotoxic T-lymphocyte associated antigen 4 (CTLA-4) is an immune checkpoint protein that down-regulates pathways of T-cell activation (Fong et al., Cancer Res. 69(2): 609-5 615, 2009; Weber Cancer Immunol. Immunother, 58:823-830, 2009). CTLA-4 is a negative regulator of T-cell activation. Blockade of CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80/CD86 expressed on antigen presenting cells and thereby blocking the negative down regulation of the immune responses elicited by the interaction of these molecules. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238.

Anti-CDLA-4 antibodies include tremelimumab, (ticilimumab, CP-675,206), ipilimumab (also known as lODl, MDX-DOlO; marketed under the name Yervoy™ and) a fully human monoclonal IgG antibody that binds to CTLA-4 approved for the treatment of unresectable or metastatic melanoma.

Another immune checkpoint protein is programmed cell death 1 (PD-1). PD-1, also called CD279, is a type I membrane protein encoded in humans by the PDCD1 gene. It has two ligands, PD-L1 and PD-L2. The PD-1 pathway is a key immune-inhibitory mediator of T-cell exhaustion. Blockade of this pathway can lead to T-cell activation, expansion, and enhanced effector functions. As such, PD-1 negatively regulates T cell responses. PD-1 has been identified as a marker of exhausted T cells in chronic disease states, and blockade of PD-1:PD-1L interactions has been shown to partially restore T cell function. (Sakuishi et al., JEM Vol. 207, Sep. 27, 2010, pp 2187-2194). PD-1 limits the activity of T cells in peripheral tissues at the time of an inflammatory response to infection and to limit autoimmunity. PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardoll, Nature Reviews Cancer, 12: 252-264, 2012). PD-1 blockade can be accomplished by a variety of mechanisms including antibodies that bind PD-1 or its ligand, PD-L1, or soluble PD-1 decoy receptors (e.g. sPD-1, see Pan et al., Oncology Letters 5: 90-96, 2013). Examples of PD-1 and PD-L1 blockers are described in U.S. Pat. Nos. 7,488,802; 7,943,743; 8,008,449; 8,168,757; 8,217,149, and PCT Published Patent Application Nos.: W003042402, W02008156712, W02010089411, W02010036959, W02011066342, W02011159877, W02011082400, and W02011161699.

PD-1 blockers include anti-PD-L1 antibodies and proteinaceous binding agents. Nivolumab (BMS-936558) is an anti-PD-1 antibody that was approved for the treatment of melanoma in Japan in July 2014. It is a fully human IgG4 antibody that binds to and blocks the activation of PD-1 by its ligands PD-L1 and PD-L2. Other anti-PD-L1 antibodies include lambrolizumab (pembrolizumab; MK-3475 or SCH 900475), a humanized monoclonal IgG4 antibody against PD-1; CT-011 a humanized antibody that binds PD-1. AMP-224 is a fusion protein of B7-DC; an antibody Fc portion; BMS-936559 (MDX-1105-01) for PD-L1 (B7-Hl) blockade. Other anti-PD-1 antibodies are described in WO 2010/077634, WO 2006/121168, WO2008/156712 and WO2012/135408. AUNP-12 (Aurigene) is a branched 29 amino acid peptide antagonist of the interaction of PD-1 with PD-L1 or PD-L2 and has been shown to inhibit tumor growth and metastasis in preclinical models of cancer.

T cell immunoglobulin mucin 3 (TIM-3) is an immune regulator identified as being upregulated on exhausted $CD8^+$ T cells (Sakuishi et al., JEM Vol. 207, Sep. 27, 2010, pp 2187-2194 and Fourcade et al., 2010, J. Exp. Med. 207: 2175-86). TIM-3 was originally identified as being selectively expressed on IFN-γ-secreting Th1 and Tc1 cells. Interaction of TIM-3 with its ligand, galectin-9, triggers cell death in $TIM-3^+$ T cells. Anti-TIM-3 antibodies are described in Ngiow et al (Cancer Res. 2011 May 15; 71(10):3540-51), and in U.S. Pat. No. 8,552,156

Other immune-checkpoint inhibitors include lymphocyte activation gene-3 (LAG-3) inhibitors, such as IMP321, a soluble 1 g fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, 5 Clin. Cancer Res. July 15 (18) 3834).

Reference to an "antibody" includes a fragment or derivative thereof, or a synthetic antibody or synthetic antibody fragment. Antibodies may be provided in isolated form or may be formulated as a medicament or pharmaceutical composition, e.g. combined with a pharmaceutically acceptable adjuvant, carrier, diluent or excipient.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies may also be useful in the methods of the invention. Monospecific polyclonal antibodies are preferred. Suitable polyclonal antibodies can be prepared using methods well known in the art.

Fragments of antibodies, such as Fab and $Fab_2$ fragments may also be provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and $F(ab')_2$ fragments are "bivalent". By "bivalent" we mean that the said antibodies and $F(ab')_2$ fragments have two antigen combining sites. In contrast, Fab, Fv, ScFv and dAb fragments are monovalent, having only one antigen combining site. Synthetic antibodies which bind to an immune checkpoint protein may also be made using phage display technology as is well known in the art.

Administration of Immune Checkpoint Inhibitor

Administration of immune checkpoint inhibitor may involve administration at regular intervals, e.g. weekly, fortnightly, or once every three or four weeks. For example, doses may be given at regular, defined, intervals over a period of one of at least 1, 2, 3, 4, 5, 6, 7, 8, weeks or 1, 2, 3, 4, 5 or 6 months.

As such, multiple doses of immune checkpoint inhibitor may be administered. For example, 1, 2, 3, 4, 5, 6, 7, 8, 9, 10 or more doses of immune checkpoint inhibitor may be administered to a subject as part of a course of treatment. In some preferred embodiments 1 or 2 doses, optionally 3 or more doses, of immune checkpoint inhibitor are administered to the subject, preferably at regular intervals (e.g. weekly, fortnightly, or once every three or four weeks). Each dose is preferably administered within a single day, e.g. over a period of 1, 2, 3, 4, 5, or 6 hours, and optionally at the same time as a dose of oncolytic herpes simplex virus.

Doses of immune checkpoint inhibitor may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days). The dose of immune checkpoint inhibitor given at each dosing point may be the same, but this is not essential. For example, it may be appropriate to give a higher priming dose at the first, second and/or third dosing points.

Administration of immune checkpoint inhibitor may be of one or more treatment cycles, e.g. 1, 2, 3, 4, 5, 6, 7, 8, 9, 10 or more treatment cycles. A subject receiving multiple treatment cycles may be given subsequent treatment cycles consecutively, without a break from treatment, or may separate all or selected treatment cycles by a break from treatment, e.g. a break of 1, 2, 3, 4, 5, 6, 7, 8 or 9 days or about 1, 2, 3, or 4 weeks.

In some embodiments a treatment cycle may comprise, or consist of, 1 or 2 doses of immune checkpoint inhibitor administered per period of about 3 or about 4 weeks. In some embodiments a treatment cycle may comprise, or consist of, one dose of immune checkpoint inhibitor administered per three week period. Doses may be separated by 21±3, 21±2 or 21±1 days. For example, doses may be given on days 1, 22, 43 etc.

A treatment cycle of immune checkpoint inhibitor may be given in conjunction with a treatment cycle of oncolytic herpes simplex virus to provide a combined treatment. The treatment cycles are not required to commence on the same day, although they may. For example, a treatment cycle of oncolytic herpes simplex virus may commence on day 1 and a treatment cycle of immune checkpoint inhibitor may commence on day 8, or on any of days 1, 2, 3, 4, 5, 6, 7, 8, 9, 10, 11, 12, 13, or 14. As such a treatment cycle of immune checkpoint inhibitor may commence after a treatment cycle of oncolytic herpes simplex virus (e.g. about a week after) or before a treatment cycle of oncolytic herpes simplex virus (e.g. about a week before). Preferably both treatment cycles will have a duration that causes them to overlap, e.g. by at least one day or more preferably by about one or about two weeks.

Subjects may receive the same dosage of immune checkpoint inhibitor at each administration within a given treatment cycle, e.g. a dosage of 50 mg, 100 mg, 150 mg, 200 mg, 250 mg, 300 mg, 350 mg or 400 mg. In some embodiments the first 1, 2 or 3 treatment cycles may comprise administration of a lower dosage amount at each administration, e.g. 150 mg, and later treatment cycles may comprise administration of a higher dosage amount at each administration, e.g. 200 mg.

Administration of immune checkpoint inhibitor may be by infusion to the blood (intravenous or intra-arterial) and subjects will preferably attend clinic on the scheduled administration days for administration of immune checkpoint inhibitor. Administration of immune checkpoint inhibitor may continue until development of severe toxicity or withdrawal of consent.

In general, administration is preferably in a "effective amount", this being sufficient to induce a treatment effect in the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentume, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In the context of treatment of a metastatic cancer, treatment may be of cancers or tumors of a given cell type. The treatment may involve eliciting a systemic anti-tumor Th1 immune response in the subject, who may be at risk of developing single or multiple metastatic cancers or tumors of the given cell type. Administration of oncolytic herpes simplex virus may therefore induce a Th1 immune response that is specific for the tumor cell type and that kills cells of inoculated tumor and non-inoculated tumors.

In some embodiments the cancer may be a solid tumor. Solid tumors may, for example, be in bladder, bone, breast, eye, stomach, head and neck, germ cell, kidney, liver, lung, nervous tissue, ovary, pancreas, prostate skin, soft-tissues, adrenal gland, nasopharynx, thyroid, retina, and uterus. Solid tumors may include melanoma, rhabdomyosarcoma, Ewing sarcoma, and neuroblastoma.

The cancer may be a pediatric solid tumor, i.e. solid tumor in a child, for example osteosarcoma, chondroblastoma, chondrosarcoma, Ewing sarcoma, malignant germ cell tumor, Wilms tumor, malignant rhabdoid tumor, hepatoblastoma, hepatocellular carcinoma, neuroblastoma, melanoma, adrenocorticoid carcinoma, nasopharyngeal carcinoma, thyroid carcinoma, retinoblastoma, soft-tissue sarcoma, rhabdomyosarcoma, desmoid tumor, fibrosarcoma, liposarcoma, malignant fibrous histiocytoma, neurofibrosarcoma.

In some preferred embodiments the cancer may be a mesothelioma, e.g. a malignant pleural mesothelioma.

The cancer may be one that is associated with effusion fluid. Such association may involve production of effusion fluid by the cancerous tissue, e.g. by cancer cells, or by normal cells near to or contained in the cancerous tissue, or it may involve overproduction of effusion fluid by other tissues (e.g. the lymphatic system) as a direct or indirect response to the presence of the cancer in the subject.

The cancer may be characterised by the collection of effusion fluid in one or more locations in the subject's body. Such locations may include one or more body cavities or tissue spaces. Body cavities (or serous cavities) may be formed by a serous membrane surrounding an organ or tissue and forming a sac in which fluid may collect.

For example, effusion fluid may collect in one or each (right or left) pleural cavity (the space between the visceral and parietal pleura). In another example, effusion fluid may accumulate in the peritoneal cavity (the space between the parietal peritoneum and visceral peritoneum). In another example, fluid may accumulate in the pericardial cavity surrounding the heart (formed by the parietal and visceral pericardium). In another example, fluid may accumulate in the perimetrium surrounding the uterus.

Thus, in some embodiments the cancer is one in which pleural effusion, peritoneal effusion (ascites), pericardial effusion or perimetrial effusion occurs.

All types of cancer may be associated with production of effusion fluid, partly because all types of cancer can metastasize to any of the body's serous cavities and result in malignant effusion (Olopade CA-A Cancer Journal For Clinicians Vol. 41, No. 3 May/June 1991). Cancers in which production of effusion fluid is known to occur include cancers of the following type or tissues: lung cancers, pleural cancers, mesothelioma, malignant pleural mesothelioma, non-small cell lung cancer (NSCLC), small cell lung cancer (SCLC), ovarian cancers, ovarian carcinoma, uterine cancer, endometrial cancer, heart cancer, breast cancer, colon cancer, stomach cancer, gastric cancer, pancreatic cancer, kidney cancer, liver cancer, lymphatic cancer (e.g. lymphoma, non-Hodgkin lymphoma), soft tissue sarcoma, osteosarcoma, adenocarcinoma, parotid cancer (e.g. parotid adenocarcinoma), thymic carcinoma, cancers of the reproductive tract (including cervical, fallopian tube, endometrium), gastrointestinal tract, or genitourinary tract, leukemia, larynx, prostate, bile duct, hypernephroma, sinus *piriformis* carcinoma, thyroid cancer, melanoma and cancers of unknown primary (CUP) origin.

The development of a malignant pleural effusion is a common complication of advanced malignancies of many types of cancer, especially breast, lung (including NSCLC and SCLC) and ovarian carcinoma (Warren et al. European Journal of Cardio-thoracic Surgery 33 (2008) 89-94). Pleural effusions are at least known to be associated with cancers of the following type or tissue: lung, breast, lymphoma, uterus, ovarian, female reproductive tract (e.g. cervical, fallopian tube, endometrium), leukemia, pancreas, kidney, colon, stomach (gastric), mesothelioma, sarcoma, larynx, prostate, bile duct, hypernephroma, sinus *piriformis* carcinoma, thyroid cancer, non-Hodgkin lymphoma, malignant melanoma, reproductive tract, gastrointestinal tract, genitourinary tract, (Warren et al. Ann Thorac Surg 2008; 85:1049-55; Warren et al. European Journal of Cardio-thoracic Surgery 33 (2008) 89-94; Schulze et al. Ann Thorac Surg 2001; 71:1809-12; Olopade CA-A Cancer Journal For Clinicians Vol. 41, No. 3 May/June 1991).

Peritoneal effusions (ascites) are at least known to be associated with cancers of the following type or tissue: ovarian, epithelial related ovarian, uterus, breast, colon, gastric, pancreatic, hepatic, colon, lymphoma, mesothelioma, and cancers of unknown primary (CUP) origin (Olopade CA-A Cancer Journal For Clinicians Vol. 41, No. 3 May/June 1991)

Pericardial effusions are at least known to be associated with cancers of the following type or tissue: lung, breast, leukemia, lymphoma, sarcoma, melanoma (Olopade CA-A Cancer Journal For Clinicians Vol. 41, No. 3 May/June 1991).

Optionally, in some preferred embodiments the cancer is not a melanoma. Optionally, in some preferred embodiments the cancer is not a cancer occurring in the skin. Optionally, in some preferred embodiments the cancer is not a primary melanoma. Optionally, in some preferred embodiments the cancer is not metastatic (secondary melanoma). Optionally, in some embodiments the cancer is not stage IIIb to stage IV melanoma.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a cancer, be suspected of having a cancer, be considered at risk of developing a cancer, or have been cured of cancer and considered at risk of relapse. Such diagnosis or assessment is preferably by a suitably qualified medical practitioner. A subject who has been cured of cancer may be a subject in remission, or a subject who is free of cancer following treatment.

The subject may be a child, i.e. a human subject of age less than 18 years, or of age less than 16 years, or of age less than 14 years, or of age less than 12 years. The age may be determined at the point of first dose with oncolytic herpes simplex virus.

Subjects may be selected for treatment as being subjects who have not mounted a clinical response to previous treatment with an immune checkpoint inhibitor as monotherapy.

A subject may be immunocompetent or immunocompromised.

Other Chemotherapeutic Agents

In addition to treating a cancer by using an oncolytic herpes simplex virus with or without an immune checkpoint inhibitor, subjects being treated may also receive treatment with other chemotherapeutic agents. For example, other chemotherapeutic agents may be selected from:

(i) alkylating agents such as cisplatin, carboplatin, mechlorethamine, cyclophosphamide, chlorambucil, ifosfamide;

(ii) purine or pyrimidine anti-metabolites such as azathiopurine or mercaptopurine;

(iii) alkaloids and terpenoids, such as *vinca* alkaloids (e.g. vincristine, vinblastine, vinorelbine, vindesine), podophyllotoxin, etoposide, teniposide, taxanes such as paclitaxel (Taxol™), docetaxel;

(iv) topoisomerase inhibitors such as the type I topoisomerase inhibitors camptothecins irinotecan and topotecan, or the type II topoisomerase inhibitors amsacrine, etoposide, etoposide phosphate, teniposide;

(v) antitumor antibiotics (e.g. anthracyline antibiotics) such as dactinomycin, doxorubicin (Adriamycin™), epirubicin, bleomycin, rapamycin;

(vi) antibody based agents, such as anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab, (vii) EGFR inhibitors such as erlotinib, cetuximab and gefitinib (viii) anti-angiogenic agents such as bevacizumab (Avastin®).

Routes of Administration

Viruses, immune checkpoint inhibitors, chemotherapeutic agents, medicaments and pharmaceutical compositions according to aspects of the present invention may be formulated for administration by a number of routes, including but not limited to, parenteral, intravenous, intra-arterial, intramuscular, intratumoral and oral. Viruses, immune checkpoint inhibitors, chemotherapeutic agents, medicaments and pharmaceutical compositions may be formulated in fluid or solid form. Fluid formulations may be formulated for administration by injection to a selected region of the human or animal body.

In some embodiments treatment with oncolytic herpes simplex virus may involve administration of the virus to a body cavity in which effusion fluid is accumulating in the subject (intracavitary administration, e.g. intrapleural or intraperitoneal); for example, as described in (Kelly et al. Novel Oncolytic Agent GLV-1 h68 Is Effective Against Malignant Pleural Mesothelioma. Human Gene Therapy 19:744-782 (August 2008)). Such administration may involve administration via an existing drain or catheter inserted in the patient for the purpose of draining effusion fluid. The virus may be administered as a fluid formulation. Administration of virus may follow complete or partial drainage of effusion fluid from the body cavity. Administration to the body cavity permits the oncolytic virus to be dispersed throughout the body cavity.

In some embodiments administration of oncolytic herpes simplex virus is not intra-tumoral.

Administration of oncolytic herpes simplex virus may be by infusion to the blood, e.g. intravenous or intra-arterial infusion, and the virus may be formulated for such administration.

In preferred embodiments the immune checkpoint inhibitor is administered to the blood, e.g. by intravenous administration (intravenous infusion), and is formulated for such administration.

Herpes simplex virus may be formulated as a suspension of virus in lactated Ringer's or in Hartmann's solution. One litre of lactated Ringer's solution typically contains about 130 mEq of sodium ion (130 mmol/L), 109 mEq of chloride ion (109 mmol/L), 28 mEq of lactate (28 mmol/L), 4 mEq of potassium ion (4 mmol/L), and 3 mEq of calcium ion (1.5 mmol/L). One litre of Hartmann's solution typically contains about 131 mEq of sodium ion (131 mmol/L), 111 mEq of chloride ion (111 mmol/L), 29 mEq of lactate (29 mmol/L), 5 mEq of potassium ion (5 mmol/L), and 4 mEq of calcium ion (2 mmol/L).

Virus may be formulated for delivery in the clinic by mixing a small aliquot of virus with a specified volume of the chosen fluid carrier, e.g. lactated Ringer's or Hartmann's solution. Virus is supplied in fluid suspension at the specified dosage concentration, e.g. $1 \times 10^7$ iu/ml and a small aliquot in the range 0.5 to 5 ml, e.g. one of about 0.5 ml, about 1 ml, about 2 ml, about 3 ml, about 4 ml or about ml, preferably about 1 ml of virus, is mixed with the fluid carrier. The volume of fluid carrier to which the aliquot of virus is added may be one of about 100 ml, about 150 ml, about 200 ml, about 250 ml, about 300 ml, about 350 ml, about 400 ml, about 450 ml, about 500 ml. In some preferred embodiments the volume of fluid carrier is about 250 ml. The fluid carrier may be provided in a bag suitable for use in intravenous or intra-arterial infusion. The viral suspension, fluid carrier and bag are all preferably sterile and the virus formulation is prepared in sterile conditions.

Infusion of the formulated viral composition to the blood may take between about 30 minutes and about 3 hours, for example about 1 hour, about 2 hours or about 3 hours.

Intravenous administration may comprise infusion into the venous system in close proximity to the location or locations of the cancer, e.g. head and neck cancer.

Infusion to the blood is preferably at a peripheral site, e.g. to a vein or artery near the surface of the skin and not within deep tissue. Examples of suitable peripheral locations are veins in the arm or leg. In some related embodiments, administration may be via a central venous line. Administration is preferably non-invasive, e.g. does not require a surgical, invasive or interventional radiological procedure in order to locate a specific vein or artery within deep tissue or proximal to internal organs. For example, administration is optionally not to the hepatic artery. The subject may have a peripheral venous device, catheter or cannula fitted in order to facilitate the administration. As such, administration can be performed in an out-patient setting in which the patient is connected to a drip.

Administration of oncolytic herpes simplex virus may be locoregional administration, e.g. to a localised region of the body in which the tumor is present. Locoregional administration may be achieved by use of chemoembolization in which administration of an oncolytic herpes simplex virus may be combined with other embolization (e.g. chemical embolization) of the tumor.

For example, one technique developed for intra-arterial infusion suitable in the context of treatment of primary liver cancer is trans-arterial chemoembolization (TACE).

TACE is normally performed by an interventional radiologist and involves accessing the hepatic artery with a catheter, which is possible by puncturing the common femoral artery in the right groin and passing a catheter through the abdominal aorta, through the celiac trunk and common hepatic artery, into the proper hepatic artery.

An arteriogram is performed to identify the branches of the hepatic artery supplying the tumor(s). Smaller catheters may then be threaded into these branches (so-called superselective positioning). This allows precision delivery of the active agents to the tumor tissue.

Once the catheter is in position, doses of the active agent (e.g. oncolytic herpes simplex virus, and/or chemotherapeutic agent and/or embolisation agent and/or contrast agent) are injected through the catheter. The total dose may be given to a single vessel, or if there are several tumor foci may be divided among several vessels supplying the tumors.

Because most liver tumors are supplied by the hepatic artery, arterial embolization interrupts the blood supply to the tumor and delays tumor growth. The focused nature of the administration of active agents enables delivery of a high therapeutic dose to the tissue requiring treatment whilst reducing systemic exposure and therefore toxicity. Embolization of the vessel assists this process in that the active agent(s) is not washed out from the tumor bed and the supply of nutrients to the tumor is decreased thereby promoting tumor necrosis.

TACE is widely used as a palliative treatment for surgically unresectable primary or metastatic HCC tumors.

Kits

In some aspects of the present invention a kit of parts is provided. In some embodiments the kit may have at least one container having a predetermined quantity of oncolytic herpes simplex virus, e.g. predetermined viral dose or number/quantity/concentration of viral particles. The oncolytic herpes simplex virus may be formulated so as to be suitable for injection or infusion to a tumor or to the blood. In some embodiments the kit may further comprise at least one container having a predetermined quantity of immune checkpoint inhibitor. The immune checkpoint inhibitor may also be formulated so as to be suitable for injection or infusion to the tumor or to the blood, or alternatively may be formulated for oral administration. In some embodiments a container having a mixture of a predetermined quantity of oncolytic herpes simplex virus and predetermined quantity of immune checkpoint inhibitor is provided, which may optionally be formulated so as to be suitable for injection or infusion to the tumor or to the blood.

In some embodiments the kit may also contain apparatus suitable to administer one or more doses of the oncolytic herpes simplex virus and/or immune checkpoint inhibitor.

Such apparatus may include one or more of a catheter and/or needle and/or syringe, such apparatus preferably being provided in sterile form.

The kit may further comprise instructions for the administration of a therapeutically effective dose of the oncolytic herpes simplex virus and/or immune checkpoint inhibitor.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIG. 1. Table showing changes in cytokine production in pleural fluid samples in human patients having malignant pleural mesothelioma in response to treatment with 1, 2 or 4 doses (each of $1\times10^7$ iu) of SEPREHVIR® given at weekly intervals. Changes are relative to patient levels of cytokine production prior to treatment with SEPREHVIR®. *No samples were available for testing from patient 06. +→+++++=small to large increase over baseline level; −=no change; ↓=decrease; tba=sample yet to be analysed.

FIG. 2. Table showing changes in IFN-α production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 3. Table showing changes in IFN-α production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 4. Table showing changes in IL-1α production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 5. Table showing changes in IL-2 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 6. Table showing changes in IL-4 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 7. Table showing changes in IL-6 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 8. Table showing changes in IL-10 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 9. Table showing changes in IL-12 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 10. Table showing changes in IL-21 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 11. Table showing changes in TNF-α production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 12. Table showing changes in IP-10 production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 13. Table showing changes in MIG production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 14. Table showing changes in VEGF production in pleural fluid samples in human patients having malignant pleural mesothelioma in response to treatment with 1, 2 or 4 doses (each of $1\times10^7$ iu) of SEPREHVIR® given at weekly intervals. No samples were available for testing from patient 06. +→+++++=small to large increase over baseline level; −=no change; ↓=decrease; tba=sample yet to be analysed.

FIG. 19. Table showing Th1 response and patient survival for one year or less or for greater than one year. Median survival is 12 months from diagnosis. *Only 7/9 patients were evaluated. No samples available from patient 06 and patient 09 is yet to reach 12 months from treatment. #10 patients, patients 08 and 09 still alive, *oldest treated patient was 84 yrs. Historical median survival for all malignant pleural mesothelioma patients is 9.5 mths from diagnosis (Beckett et al (2015) Lung Cancer 88, 344).

FIG. 20. Table showing cytokines and chemokines detected in pleural fluid samples at high levels (ng/ml) and low levels (pg/ml) and cytokines and chemokines not detected.

FIG. 23. Table showing expression of pleural fluid cytokines and chemokines in nine human patients in response to treatment with Seprehvir. –=unchanged, +=weak to +++++= strong response, ↓=decrease, nd=not done.

FIG. 24. Table showing cytokines and chemokines showing low or no response to treatment with Seprehvir in pleural fluid samples from nine human patients. nd=not done, –= unchanged, +=increase, ↓=decrease.

FIG. 25. Table showing summary of patient Th1 cytokine and chemokine responses in nine human patients. –=unchanged, +=weak to +++++=strong response.

FIG. 32. Female and male M3-9-M tumor-bearing mice received three doses of intra-tumoral (i.tu.) Seprehvir injection followed by intra-peritoneal (i.p.) injection of anti-PD-1 or control antibody. Immune cell infiltrates in tumors were evaluated by flow cytometry analyses 72 hours post intra-peritoneal antibody injection. In each chart, columns from left to right are PBS/Control antibody, PBS/Anti-PD-1 antibody, Seprehvir/Control antibody and Seprehvir/Anti-PD-1 antibody.

FIG. 39. Charts showing expression of cytokines in PBMC after treatment. PBMC were isolated from leukapheresis cones, seeded at $2\times10^6$ cells/ml and treated±reovirus or HSV1716 (MOI 1); dexamethasone (0.2 mM); PLX4720 (2 µM); 2 Gy XRT; 8 Gy XRT. After 24 or 48 h culture the cells were harvested, stained for the markers indicated and analyzed by FACS.

FIG. 56. Table showing summary of patient Th1, immune cell and cytokine responses (Example 1).

FIG. 57. Table showing summary of patient anti-tumor IgG responses.

FIG. 58. Table showing detection of HSV-1 DNA in patient blood samples. "Pos"=positive for HSV-1 DNA, "Neg"=negative for HSV-1 DNA.

FIG. 59. Table showing detection of HSV-1 DNA in patient blood samples for 8 patients enrolled on NCT00931931. IV=intravenous administration of Seprehvir, ITu=intratumoral administration of Seprehvir, "Pos"=positive for HSV-1 DNA, "Neg"=negative for HSV-1 DNA, nd=not done.

FIG. 60. Digital PET/CT images for patient HSV13 enrolled on NCT00931931 at day 14 and day 28 post intravenous administration of Seprehvir. Lesion is circled and SUV indicated.

Figure 15:
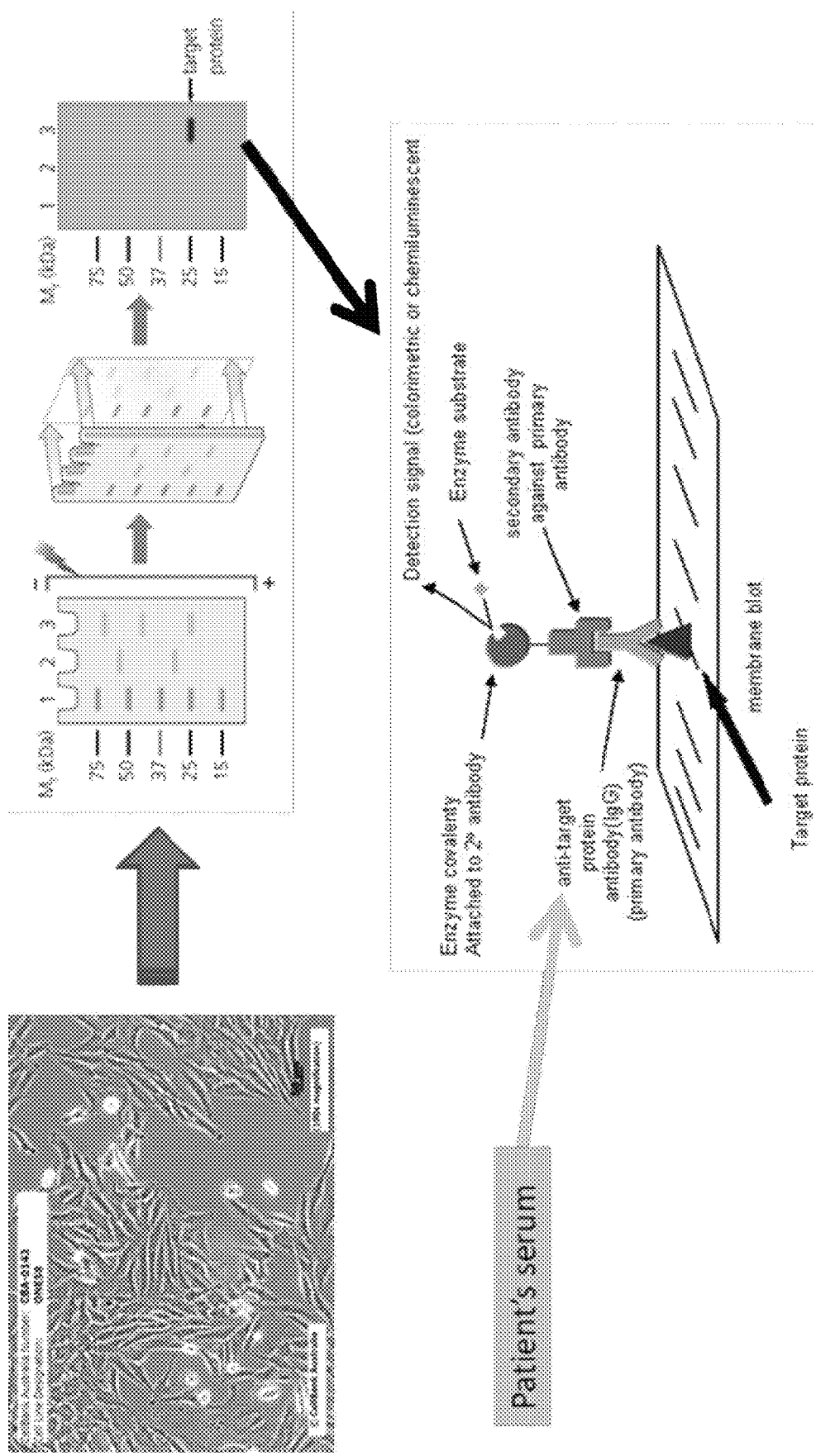
FIG. 15. Diagram illustrating Western Blotting procedure used to probe cell extracts for anti-tumor IgG response induced by intrapleural administration of SEPREHVIR®.

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

Malignant pleural mesothelioma (MPM) remains a major challenge, with limited therapeutic options. Multifocal intrapleural disease can cause disabling symptoms of pain and breathlessness, in the absence of distant metastases, so an intrapleural treatment approach is attractive.

SEPREHVIR® (HSV1716) is a mutant oncolytic herpes simplex virus type 1 deleted in the RL1 gene which encodes the protein ICP34.5, a specific determinant of virulence. Mutants lacking the RL1 gene are capable of specific replication in cancer cells and inducing anti-tumor immune responses. Clinical studies with SEPREHVIR have been completed in adult glioma, melanoma, squamous cell head and neck cancer, and studies are ongoing in non-CNS solid tumors and MPM. In total, 98 patients have received SEPREHVIR and the virus is well-tolerated with no spread to surrounding normal tissue or no shedding in patients. SEPREHVIR selectivity for replication only in tumor cells and intimations of efficacy and immuno-stimulatory potential have been demonstrated.

Cytokines are secreted intercellular signalling molecules that regulate many different processes including inflammation, host defence and cell differentiation. Cytokine profiles may help understand changes in the pleural fluid samples in patients following SEPREHVIR® administration.

Upon activation, naive CD4+ helper T cells differentiate into distinct subsets. The development of the subsets is driven in part by the cytokine milleu. Type 1 (Th1) cells help drive cellular immunity against intracellular pathogens. IL-12 and IFNγ induce Th1 cell development. Th1 cells produce IFN-γ and IL-2, which provided a positive feedback loop to enhance Th1 cell differentiation and NK cell and CD8+ T cell cytolytic activity.

Th2 cells play a crucial role in the humoral response against extracellular pathogens. IL-4 drives development of Th2 cells, which subsequently produce IL-4, IL-5 and IL-13. These cytokines induce B cell proliferation, antibody production, IgE class switching and activate eosinophils respectively.

Another distinct helper T cell lineage, Th17 is important for mucosal immunity. De-regulation of Th17 may significantly contribute to the development of autoimmunity. IL-17 produced by Th17 cells induces secretion of proinflammatory cytokines IL-6, IL-8, GM-CSF and TNFα. Many of these molecules link innate and adaptive immunity through the recruitment and activation of innate immune cells.

Effective immune responses require finely tuned coordination between pro- and anti-inflammatory signals. Proinflammatory molecules play important roles in activating key immune players to fight infection. IL-8 induces granulocyte migration and activates neutrophil phagocytic activity. GM-CSF mobilizes monocytes into infected tissue and activates macrophage and neutrophils. TNFα is a multifunctional proinflammatory cytokine involved with a number of processes including cell proliferation, differentiation and apoptosis.

Uncontrolled inflammation may damage surrounding host tissue. IL-10 is a prototypical anti-inflammatory cytokine that serves to terminate the acute inflammatory response by inhibiting Th1 cells function and pro-inflammatory cytokine production.

Example 1—Cytokine Responses Following Intrapleural Administration of Oncolytic HSV SEPREHVIR® in Patients with Malignant Pleural Mesothelioma We are currently conducting a phase I/IIa trial at Cancer Clinical Trials Centre, Weston Park Hospital, Sheffield and Queen Elizabeth University Hospital, Glasgow, United Kingdom to determine the safety and potential for efficacy of SEPREHVIR® given intrapleurally to patients with malignant pleural mesothelioma (MPM). Patients receive $1 \times 10^7$ iu SEPREHVIR® through their pleural catheter on one, two or four occasions each dose given one week apart, in three separate patient cohorts. To date 11 patients have been treated, 3 in each 1 and 2 dose cohorts and 5 in the 4 dose cohort and SEPREHVIR® has been well-tolerated with few adverse events in any patients. An exploratory objective, to assess tumor responses by CT using modified RECIST criteria, has demonstrated disease stabilisation in 6/10 evaluable patients.

Pleural fluid and plasma samples have been collected pre- and post-treatment and analysed to assess patient responses to SEPREHVIR® administration.

1.1 HSV DNA

Figure 55:
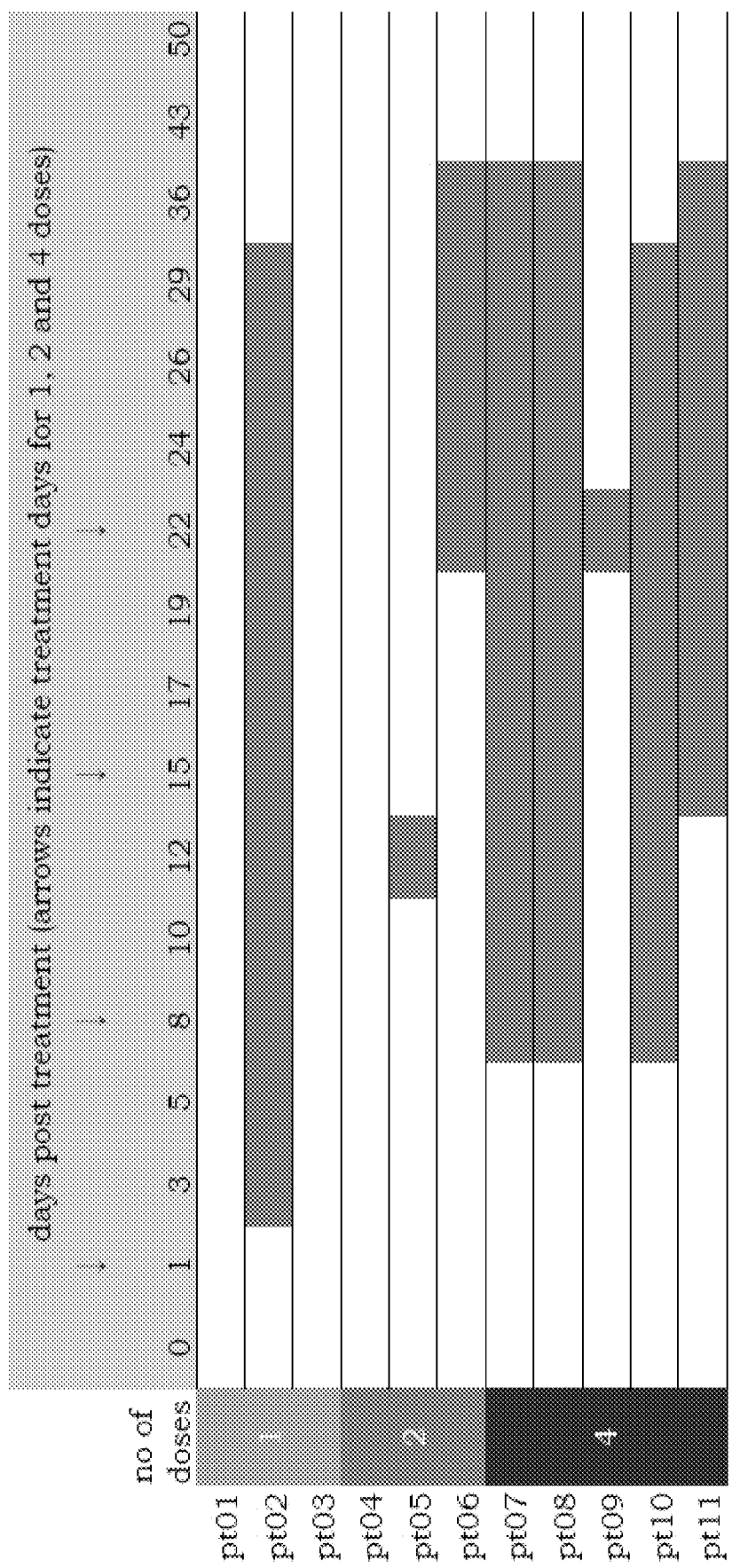
FIG. 55. Chart showing Seprehvir persistence in pleural fluids (Example 1).

HSV DNA was detected in the pleural fluids of most patients and in some persisted for at least two or four weeks post-administration (FIG. 55).

1.2 Cytokine Analysis

Pleural fluid samples were collected from patients following intrapleural administration of SEPREHVIR® and were analysed for changes in the levels of the following cytokines, or potential biomarkers: IFN-γ (Interferon-gamma), IFN-α (Interferon-alpha), the following Interleukins (IL): IL-1α, IL-2, IL-4, IL-6, IL-10, IL-12, IL-21, IP-10 (IFN-γ inducible protein 10), MIG (monokine induced by IFN-γ), TNF-α (Tumor necrosis factor alpha), and VEGF (Vascular Endothelial Growth Factor).

Changes in cytokine and chemokine levels may be indicative of a developing immune response in the pleural space and changes in potential biomarker levels may be indicative of patient responses to treatment.

1.2.1 Materials and Methods

Commercially available ELISA kits were used to measure the concentrations of these cytokines and potential biomarkers in biological fluids. ELISA kits for quantifying cytokines, chemokines and potential biomarkers in biological fluids were used exactly as specified in the manufacturer's instructions. For example, Novex® (Thermo Fisher) ELISA kits allow specific, quantitative measurements of cytokines, chemokines and disease-related proteins in various biological fluids. ELISA kits were selected on the basis that they are compatible with biological fluids such as serum or plasma.

For detection of human interferon-γ ELISA Kit Cat # KHC4021, 4022, 4021C (Invitrogen, Camarillo, Calif., USA) was used. For detection of human VEGF ELISA Kit Cat # KHG0112, 0111 (Invitrogen, Camarillo, Calif., USA) was used.

Pleural fluid samples from patients were delivered on dry ice, thawed and processed for subsequent analysis. 5-10 ml of each pleural fluid were stored at −70° C. in 15 ml centrifuge tubes for analysis of cytokines and potential biomarkers.

Prior to using an ELISA kit, its compatibility with pleural fluids and useful dilution range was tested. Two pleural fluids are used for this test, one sample prior and one post administration of SEPREHVIR® were diluted 1:10, 1:100 and 1:1000 using the dilution buffer provided with the kit. One strip of eight wells was removed from the kit and the undiluted, 1:10, 1:100 and 1:1000 dilutions for each samples were added to individual wells. The ELISA protocol was then followed exactly as specified by the manufacturer and the resultant OD450 nm readings identify the most appropriate sample dilutions for use in the ELISA. The most appropriate dilutions should generate an OD450 nm of between 0.5-1.5 within 15-30 mins. Pleural fluid samples were then analysed at this appropriate dilution.

1.2.2 Results

Detection of changes in levels of cytokines and biomarkers (see FIGS. 1 to 14).

Th1 Associated Cytokines

IL-2:

Patients receiving 4 doses of SEPREHVIR® showed an increase in IL-2 production (FIG. 5).

IL-12:

Patients receiving 4 doses of SEPREHVIR® showed an increase in IL-12 production (FIG. 9).

IL-12, produced by dendritic cells, macrophages and human B-lymphoblastoid cells, is known as a T cell stimulating factor and involved in the differentiation of naive T cells into Th1 cells. IL-12 is important within the immune response with various activities including mediating the enhancement of the cytotoxic activity of NK cells and CD8+ cytotoxic lymphocytes, stimulating production of IFN-γ, TNF-α from T-cells and reduces IL-4 mediated suppression of IFN-γ.

IL-12 has been shown to have anti-angiogenic abilities by increasing production of IFN-γ which causes the increased production of IP-10, which mediates an anti-angiogenic effect.

IFN-γ:

IFN-γ levels were notably increased from low initial levels in patients receiving single and multiple doses of SEPREHVIR® (FIG. 2).

IFN-γ functions include enhancing the cytotoxic activity, activation, growth and differentiation of T-cells, macrophages and NK cells. As well as the activation of other cells types such as B-cells and fibroblasts. IFN-γ production is a characteristic of Th1 differentiation and promotes a Th1 immune phenotype by causing naive CD4+ cells (Th0) to differentiate into Th1 cells while suppressing Th2 cell differentiation. IFN-γ further enhances the immune response by stimulating macrophages which upregulates antigen processing and presentation pathways, promoting CD4+ T cell activation and cell-mediated immunity. Through upregulation of various cells, IFN-γ directs the flow of specific immune cells to the site of inflammation or infection (Boehm, U., Klamp, T., Groot, M., Howard, J. C. (1997) Cellular responses to interferon-gamma. Annu. Rev. Immunol. 15, 749-795).

IFN-γ produced by APC (antigen presenting cells) that secrete IFN-γ may stimulate the self-activation and activation of nearby cells. The production of IFN-γ is controlled by various cytokines, importantly IL-12 and IL-18 (Frucht, D. M., Fukao, T., Bogdan, C., Schindler, H., O'shea, J., Koyasu, S. (2001) IFN-gamma production by antigen-presenting cells: mechanisms emerge. Trends Immunol. 22, 556-560). These cytokines serve roles within the innate immune response, IL-12 is secreted by macrophages which then attract NK cells to the site, while IL-12 continues to promote IFN-γ synthesis. IFN-γ is negatively regulated by IL-4 and IL-10.

IP-10:

Patients receiving single and multiple doses showed a strong upregulation of IP-10 (FIG. 12).

Interferon gamma-induced protein 10 (IP-10) is a chemokine secreted by various cell types including monocytes, endothelial cells and fibroblasts in response to IFN-γ. IP-10 has various roles within the immune system, arguably the most important of role is being a potent chemoattractant for monocytes/macrophages, T cells, NK cells and dendritic cells, IP-10 promotes anti-tumor activity and inhibition of angiogenesis (Dufour. J. H., Dziejman. M., Liu. M. T., Leung. J. H., Lane. T. E., Luster. A. D. (2002) IFN-γ-Inducible protein 10(IP-10) deficient mice reveal a role for IP-10 in effector T cell generation and trafficking. Jour Immunology. 168. 7. 3195-3204). IP-10 and other members of the chemokine family including MIG, CXCL9, CXCL11 and CXCL4 have been proposed as a therapeutic agent in the fight against cancer as they induce injury to established tumor associated vasculature and promote tumor necrosis (Homey, B., A. Müller, and A. Zlotnik. 2002. Chemokines: agents for the immunotherapy of cancer? Nat. Rev. Immunol. 2:175-184).

MIG:

Analysis of pleural fluid cytokines by AbCam ELISA indicated that baseline levels of MIG (before treatment with SEPREHVIR®) were high. Samples were diluted 1:100 before assay. Patients receiving single and multiple doses showed a strong upregulation of MIG (FIG. 13).

Monokine induced by gamma interferon (MIG), closely related to the chemokine CXCL10, is a T cell and NK cell bearing the chemokine receptor CXCR3 chemoattractant (Walser. C. T., Xinrong. M., Kundu. N., Dorsey. R., Goloubeva. W. O., Fulton. M. A. (2007) Immune-mediated Modulation of Breast Cancer Growth and Metastasis by the Chemokine Mig (CXCL9) in a Murine Model. J Immunother 2007; 30:490-498). CXCR3 can regulate leukocyte trafficking, attracts Th1 cells and promotes Th1 cell maturation. MIG has been shown to have anti-tumor activity in a number of tumor models as well as stimulating T cells to the site of injury and having anti angiogenic properties (Saudemont A, Jouy N, Hotuin D, et al. NK cells that are activated by CXCL10 can kill dormant tumor cells that resist CTL-mediated lysis and can express B7-H1 that stimulates T cells. Blood. 2005; 105:2428-2435). Furthermore, there is evidence to suggest NK cells that have been stimulated by MIG have the potential to kill dormant tumor cells that have previously been resistant to cell death (Saudemont. A., Jouy. N., Hetuin. D., Quesnel. B. (2005) NK cells that are activated by CXCL10 can kill dormant tumor cells that resist CTL-mediated lysis and can express B7-H1 that stimulates T cells. Blood. Vol 15. 6. 2428-2435).

TNF-α:

Patients showed a small increase in TNF-α production (FIG. 11).

Tumor necrosis factor alpha is a multifunctional inflammatory cytokine produced by macrophages/monocytes during inflammation and implicated in signalling events that lead to cell necrosis and apoptosis (Idriss. H. T and Naismith. H. J. (2000) TNFα and the TNF receptor subfamily: Structure-function relationship(s). Microscopy research and technique. 50. 184-195). Although the exact mechanism is unknown, TNFα is critical in efficient T cell immune responses, affecting T cell priming, proliferation, recruitment and function. The link between anti-TNFα therapies and increased incidence of malignancies in Rheumatoid Arthritis patients has suggested a link between TNFα in the development, progression and immune surveillance of tumors as well as potentially possessing anti-tumor properties (Calzascia T, Pellegrini M, Hall H, et al. TNF-α is critical for antitumor but not antiviral T cell immunity in mice. *The Journal of Clinical Investigation* 2007; 117(12): 3833-3845. doi:10.1172/JCI32567).

Proinflammatory Cytokines

IL-6:

Analysis of pleural fluid cytokines by ELISA indicated that baseline levels of IL-6 (before treatment with SEPREHVIR®) were high. Samples were diluted 1:1000 before assay. In most patients, even at multiple doses IL-6 levels did not rise notably compared to baseline levels (FIG. 7).

Detection of high levels of IL-6 is consistent with previous reports of detection of IL-6 in patients having malignant pleural mesothelioma (T Nakano et al., Interleukin 6 and its relationship to clinical parameters in patients with malignant pleural mesothelioma. British Journal of Cancer (1998) 77(6), 907-912; Siti N. Abdul Rahim et al., The role of interleukin-6 in malignant mesothelioma *Transl Lung Cancer Res* 2015; 4(1):55-66).

IL-6 is a pro and anti-inflammatory cytokine which is produced by a variety of cells such as T cells, B cells monocytes, fibroblasts and keratinocytes and macrophages. IL-6 stimulates a broad range of cellular and physical responses in the event of infection or trauma. Recent research suggests IL-6 along with TNFα and IL-1, are major proinflammatory cytokines, IL-6 is an important modulator of CD4 T cell effector functions therefore impacting the immune response and contributing to inflammation (Dienz. O., Rincon. M. (2009). The effect of IL-6 on CD4 T cell responses. Clin Immunol. 130(1): 27-33). In response to PAMPS (pathogen-associated molecular patterns), which are located on the cell surface and intracellular compartments, IL-6 is produced by macrophages, causing a signalling cascade that produces an inflammatory cytokine production. IL-6 may protect CD4 T cells from undergoing apoptosis and stimulates T cell activation as well as T cell migration. A major function of IL-6 is antibody induction (Akira. S., Hirano. T., Taga. T., Kishimoto. T. (1990) Biology of multifunctional cytokines: IL6 and related molecules (IL1 and TNF). The FASEB Journal. 4. 11. 2860-2867).

IL-1α:

IL-1α levels were essentially unchanged in patients receiving single or multiple doses of SEPREHVIR® compared to baseline levels (FIG. 4).

IL-1α possesses a strong proinflammatory effect. IL-1α is multifunctional and produced by tissue macrophages, monocytes, fibroblasts and dendritic cells. IL-1α enables transmigration of immunocompetent cells to sites of infection and considered a central cytokine in the regulation of immune responses. The release of IL-1α can induce activation of NFkB which will promote cell survival, proliferation and angiogenesis (Wolf. J. S., Chen. Z., Dong. G., Sunwoo. J. B., Bancroft. C. C., Capo. D. E., Yeh. N. T., Mukaida., Waes. C. V. (2001) IL (Interleukin)-1a Promotes Nuclear Factor-kB and AP-1-induced IL-8 Expression, Cell Survival, and Proliferation in Head and Neck Squamous Cell Carcinomas. Clin Cancer Res. 7. 1812-1820).

Th2 Associated Cytokines:

IL-4:

IL-4 levels were essentially unchanged in patients receiving single of multiple doses of SEPREHVIR® compared to baseline levels (FIG. 6).

IL-4 stimulates the differentiation of naive T cells (Th0 cells) to effector T cells (Th2 cells), subsequently Th2 cells produce additional IL-4 and have a role in a class switch response to IgG1 and IgE isotypes of B-cells (Kabsech. M., Schedel. M., Carr. D., Woitsch. B., Fritzsch. C., Weiland. S. K., Mutius. E. (2006) IL-4/IL-13 pathway genetics strongly influence serum IgE levels and childhood asthma. Journal of Allergy and Clinical Immuno. Vol 117. 2. 269-274). One of the biological activities of IL-4 is the stimulation of activated B-cell and T-cell proliferation. IL-4 is considered a key regulator in humoral and adaptive immunity. IL-4 is known to decrease the production of Th1 cells, IFN gamma, macrophages and dendritic cell IL-12.

IL-10:

Patients receiving 4 doses of SEPREHVIR® showed an increase in IL-10 production (FIG. 8). Although IL-10 is associated with Th2 cells it acts to regulate the Th1 response, preventing an excessive Th1 response. Its upregulation in patients exhibiting a more pronounced Th1 response is consistent with this regulatory function and confirms the authenticity of the Th1 response.

IL-10 is an anti-inflammatory cytokine primarily produced by monocytes and to a lesser extent by Th2 lymphocytes, mastocytes and in certain activated T and B cells. IL-10 limits the production of proinflammatory cytokines (including IL-12, IL-6, IL-1α, TNFα, IL-8 and IP-10), resulting in the indirect inhibition of Th1 cells (Couper. K. N., Blount. D. G., Riley. E. M. (2008) IL-10: The master regulator of immunity to infection. Jour Immunol. 180. 5771-5777). However IL-10 can directly act on CD4+ T cells causing an inhibition of proliferation and production of IL-2, IFN-γ, IL-4, IL-5 and TNF α, allowing IL-10 to directly regulate the innate and adaptive Th1 and Th2 responses by limiting T cell activation while inhibiting pro inflammatory responses (Moore, K. W., R. de Waal Malefyt, R. L. Coffman, A. O'Garra. 2001. Interleukin-10 and the interleukin-10 receptor. Annu. Rev. Immunol. 19: 683-765).

During infection IL-10 both regulates and inhibits pro inflammatory cytokines to help prevent tissue damage which would result in the over production of pro inflammatory cytokines.

Other Cytokines and Biomarkers:

IFN-α:

IFN-α levels were essentially unchanged in patients receiving single of multiple doses of SEPREHVIR® compared to baseline levels (FIG. 3).

Classed within the type I IFN family of interferons, IFN-α are produced by dendritic cells in response to viral infection and have immunomodulatory functions which causes immune cell differentiation, activation and survival (Padovan, E., Spagnoli. G., Ferrantini. M., Heberer. M. (2002) IFN-α2a induces IP-10/CXCL10 and MIG/CXCL9 production in monocyte-derived dendritic cells and enhances their capacity to attract and stimulate CD8+ effector T cells. Journal of Leukocyte Biologyvol. 71 no. 4 669-676).

VEGF:

VEGF levels increased in some patients but it was notable that baseline levels of VEGF in these patients (before treatment with SEPREHVIR®) were high (FIG. 14).

Vascular endothelial growth factor is a signal protein that stimulates angiogenesis and vasculogenesis, VEGF is considered to be an important factor in tumor growth (Carmeliet. P. (2005) VEGF as a key mediator of angiogenesis in cancer. Oncology. 69. 3. 4-10). VEGF production can be induced in cells that are lacking oxygen, released VEGF triggers a tyrosine kinase pathway leading to angiogenesis, leading VEGF to be a potential target in the treatment of cancer (Ohm, J., Gabrilovich. D., Sempowski. G., Kisseleva. E., Parman. K., Nadaf. S., Carbone. D. (2003) VEGF inhibits T-cell development and may contribute to tumor-induced immune suppression. Blood. 101. 12). VEGF has been shown to promote monocytes/macrophage migration and increase the production of B cells, however VEGF has also been shown to inhibit T cell production and over all reducing immune cell function (Ferrara. N., Gerber H., LeCouter. J. (2003) The biology of VEGF and its receptors. Nature Medicine 9, 669-676).

IL-21:

Some patients exhibited a small increase in IL-21 levels (FIG. 10).

Induction of a Th1 Response Varies Between Patients

Figure 21:
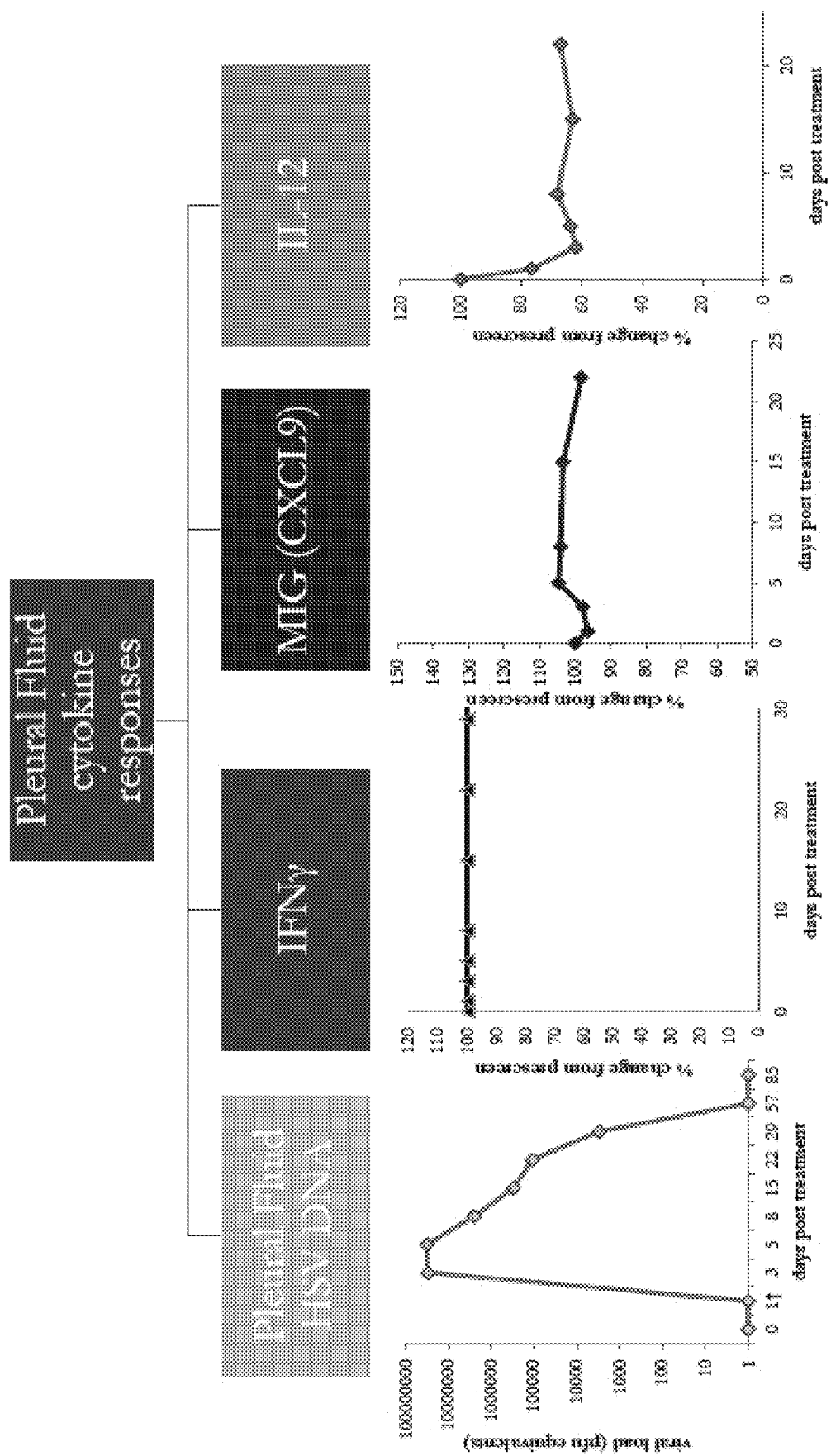
FIG. 21. Seprehvir replicates and persists but patient 02 fails to mount a Th1 response. Charts show: HSV DNA detectable in pleural fluid samples taken from patient 02 at intervals post administration of Seprehvir; IFNγ response, MIG (CXCL9) response and IL-12 response.
Figure 26:
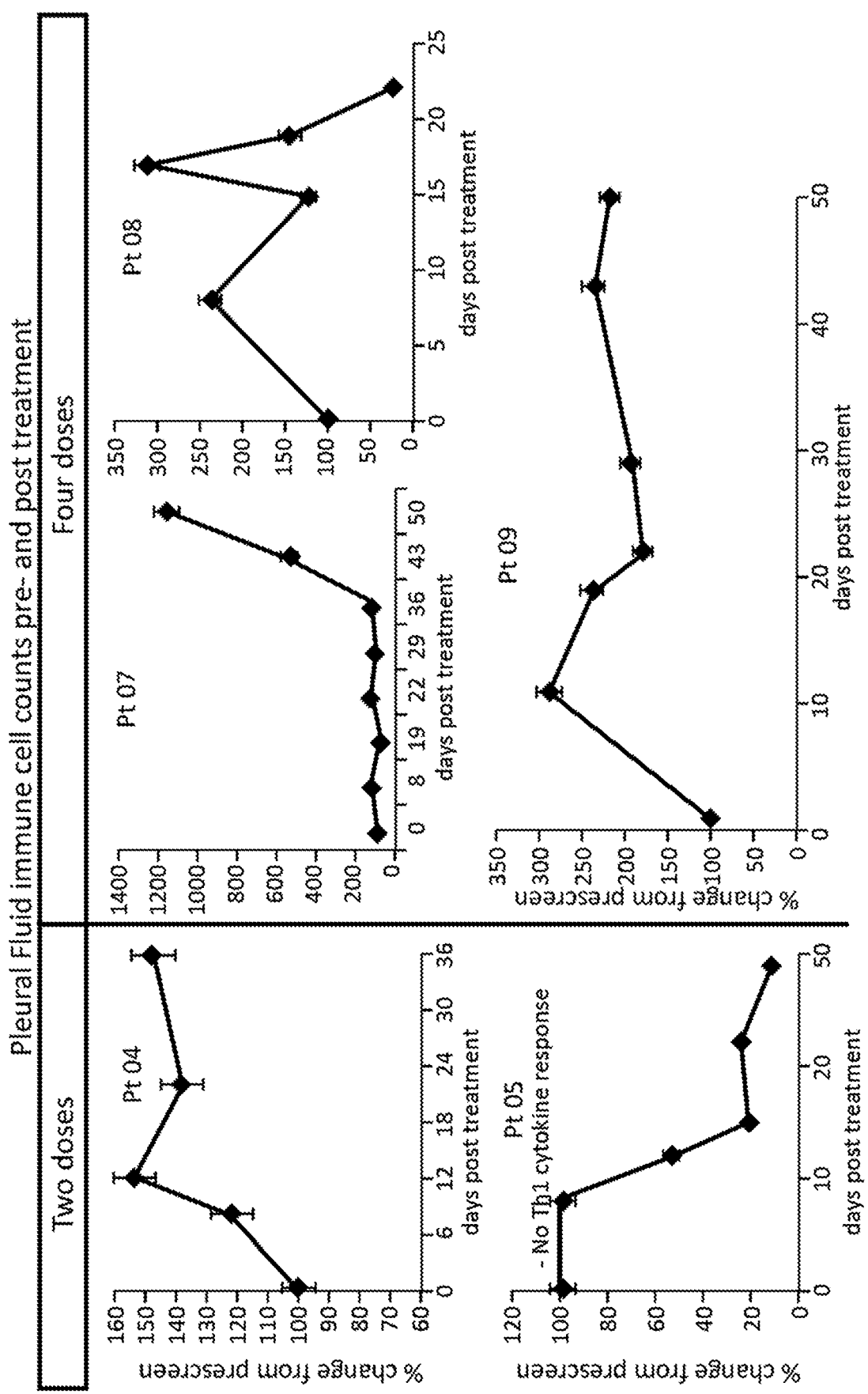
FIG. 26. Charts showing immune cell recruitment post-Seprehvir is associated with Th1 cytokine response in two patients receiving two doses of Seprehvir (on days 1 and 8) and three patients receiving four doses of Seprehvir (on days 1, 8, 15 and 22). Day 0 data point represents cell count prior to treatment with Seprehvir. Th1 responses were observed in patients 04, 07, 08 and 09. Pt=patient.
Figure 27:
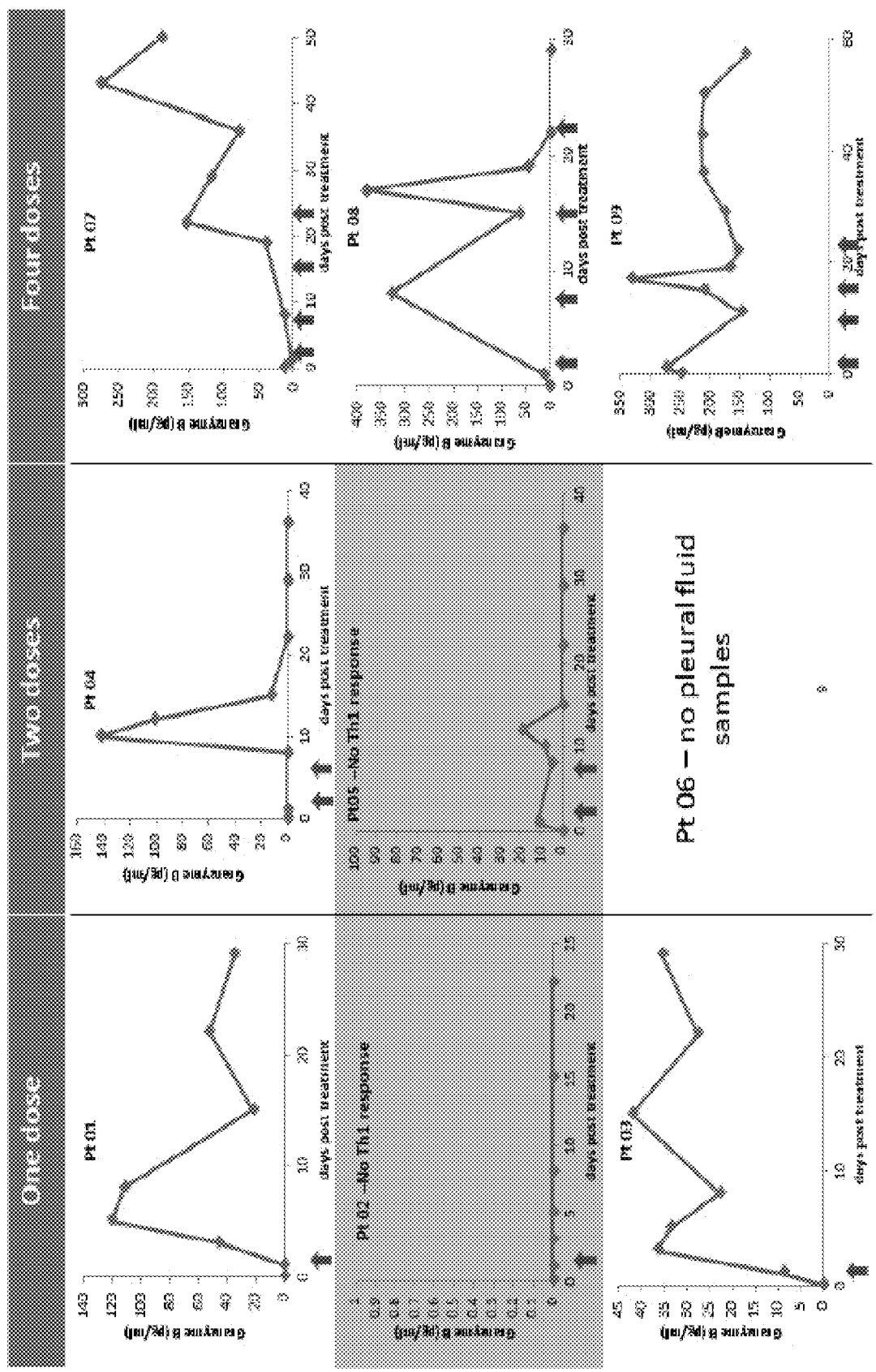
FIG. 27. Charts showing Granzyme B is associated with Th1 cytokine response post Seprehvir treatment in three patients receiving one dose of Seprehvir, two patients receiving two doses of Seprehvir and three patients receiving four doses of Seprehvir. Th1 responses were observed in patients 01, 03, 04, 07, 08 and 09. Pt=patient. Granzyme B and perforin have been shown to induce CTL-mediated target cell DNA fragmentation and apoptosis. (Lord et al., Granzyme B: a natural born killer. Immun Rev. 2003 June 193:31-8).
Figure 28:
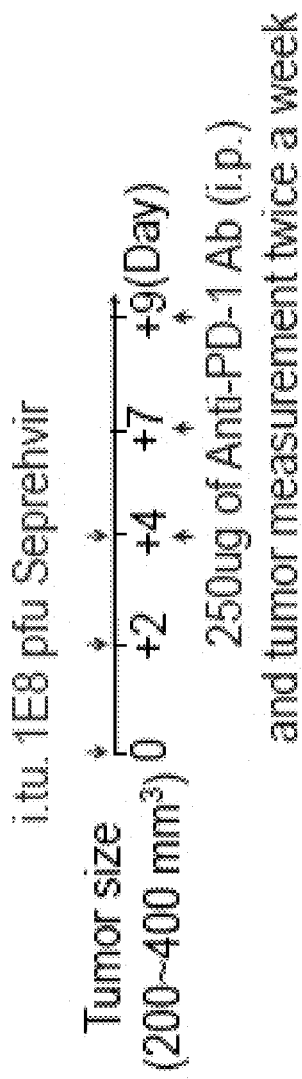
FIG. 28. C57BL/6 mice were injected with $5\times10^6$ M3-9-M cells subcutaneously. Tumors were treated intra-tumorally (i.tu.) with Seprehvir when sizes reached 200–400 mm$^3$. Intra-peritoneal (i.p.) injection of anti-PD-1 antibody were given twice a week after last dose of virus treatment. Tumor growth was monitored twice a week. Mice were sacrificed when tumors reached 2,500 mm$^3$ in volume or grew over 2 cm in length. pfu=Plaque Forming Unit.

In some patients Seprehvir replicated and persisted in the pleural fluid but did not induce a Th1 response, e.g. patient 02 (FIGS. 21 and 27), patient 05 (FIGS. 26 and 27).

Figure 22:
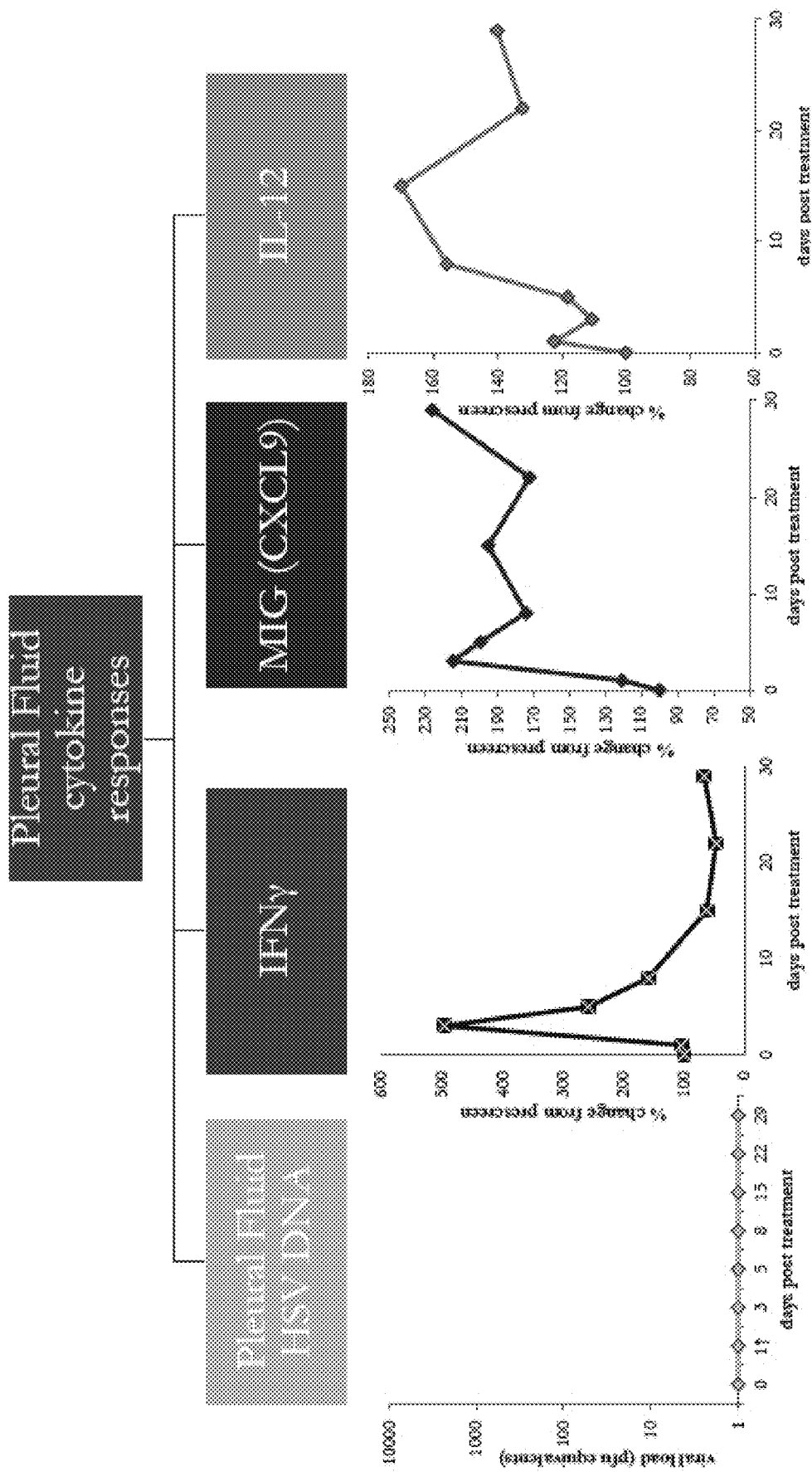
FIG. 22. Seprehvir is undetectable but patient 03 mounts a robust IFNγ response. Charts show: HSV DNA detectable in pleural fluid samples taken from patient 03 at intervals post administration of Seprehvir; IFNγ response, MIG (CXCL9) response and IL-12 response.

In other patients Seprehvir was undetectable in the pleural fluid but induced a robust Th1 response, e.g. patient 03 (FIGS. 22 and 27). The absence of detectable HSV DNA in the pleural fluid is not inconsistent with an HSV mediated treatment effect. The levels of the virus in the pleural fluids could be below the detection limit of 100 pfu equivalents/ml or it could be persisting and spreading intracellularly. In other studies we have noted viral adsorption by cells and tissue within 1 hour of administration to patients such that virus was not detectable in blood for a period of time after which HSV DNA was detectable. This is consistent with adsorption of virus following administration and re-emergence later in fluid samples after build up of productive infection within the tumor tissue.

Figure 54:
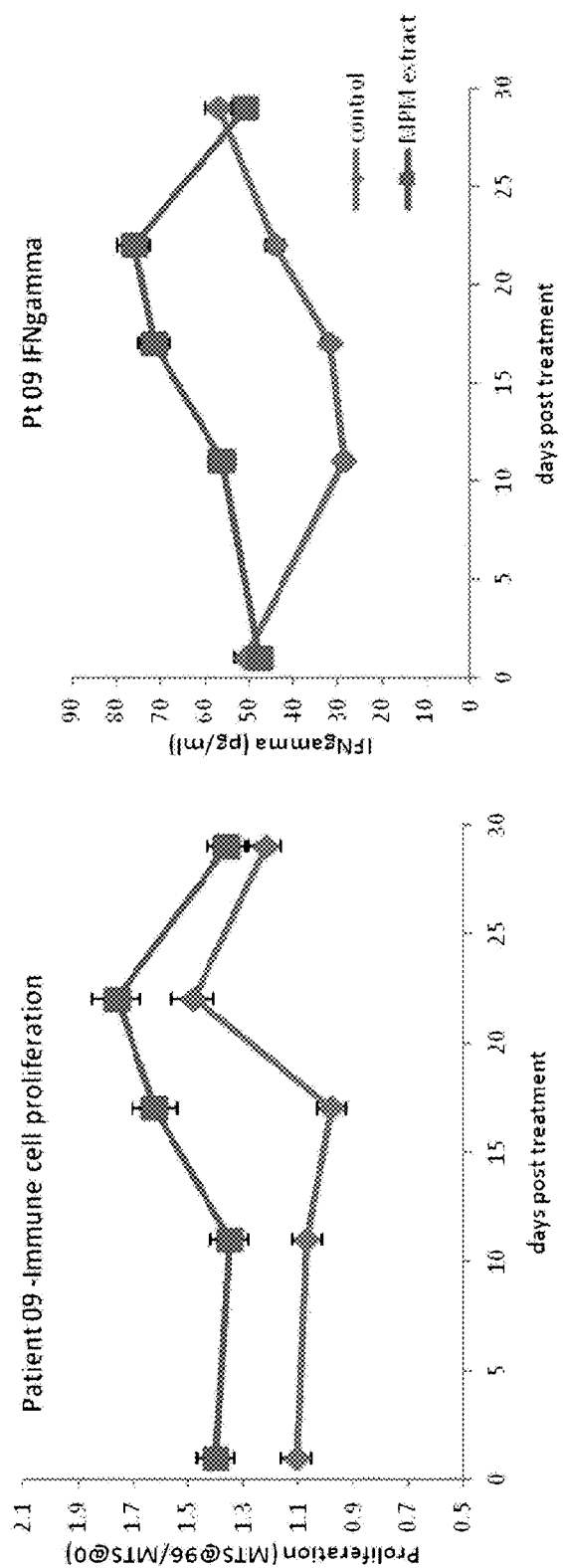
FIG. 54. Charts showing immune cell proliferation and IFNγ levels in patient 09 (Example 1).

Proliferation of immune cells and IFNγ production was measured in pleural fluid samples from patient 09 on day 1 (pre-treatment) and at days 11, 17, 22 and 29 post-administration of Seprehvir (patient 09 received four doses of Seprehvir on days 1, 11, 15 and 22). Cells were stimulated in the presence of anti-CD3 antibody and the whole cell extract from an MPM cell line (MSTO211H). Control cells were incubated with the anti-CD3 antibody+PBS. Proliferation was measured by MTS assay and proliferation was calculated as MTS at 96 hrs/MTS at 0 Hrs. IFNγ was measured in culture supernatants by ELISA at 96 hrs. Results are shown in FIG. 54.

Comments

Analysis of pleural fluid cytokines by ELISA indicated that SEPREHVIR® administration was associated with Th1-type responses with increased levels of IFNγ, IP-10 and TNFα and accompanied by increased levels of IL-10 in most patients.

Analysis of pleural fluid cytokines by ELISA indicated that they were generally rich in IL-6, MIG and VEGF. Pleural fluids had high levels of IL-6 and IL-12 and, in most patients, there were moderate increases of both post SEPREHVIR® administration. Pleural fluids were also rich in VEGF and levels increased in 4/9 patients post SEPREHVIR® administration.

IL-1α, IL-4 and IFNα were not detected pre-treatment and showed no response to SEPREHVIR® administration.

Post SEPREHVIR administration there were increased levels of IFN-γ, IP-10, MIG, TNFα and IL-6 in most patients, including patients receiving only one dose of SEPREHVIR®. IL-2, and IL-12 increases were most notable in patients receiving 4 doses of SEPREHVIR®.

Overall, these responses are consistent with development of a Th1 response.

IL-1α, IL-4, IL-21, and IFNα were not detected pre-treatment and showed little or no response to SEPREHVIR® administration, consistent with lack of development of a Th2 response.

Example 2—Novel Anti-Tumor Serum IgG Response

Patient serum samples were used to probe cell extracts in order to investigate the possibility of an anti-tumor antibody response to treatment with SEPREHVIR®. Cell extracts were prepared from cell lines: MSTO-211H (mesothelioma; ATCC CRL-2081), SPC111 (mesothelioma), and HuH7 (hepatic carcinoma), and contacted with patient sera. IgG: target complexes were detected using an anti-human IgG antibody by standard Western Blotting procedures (FIG. 15).

Figure 16:
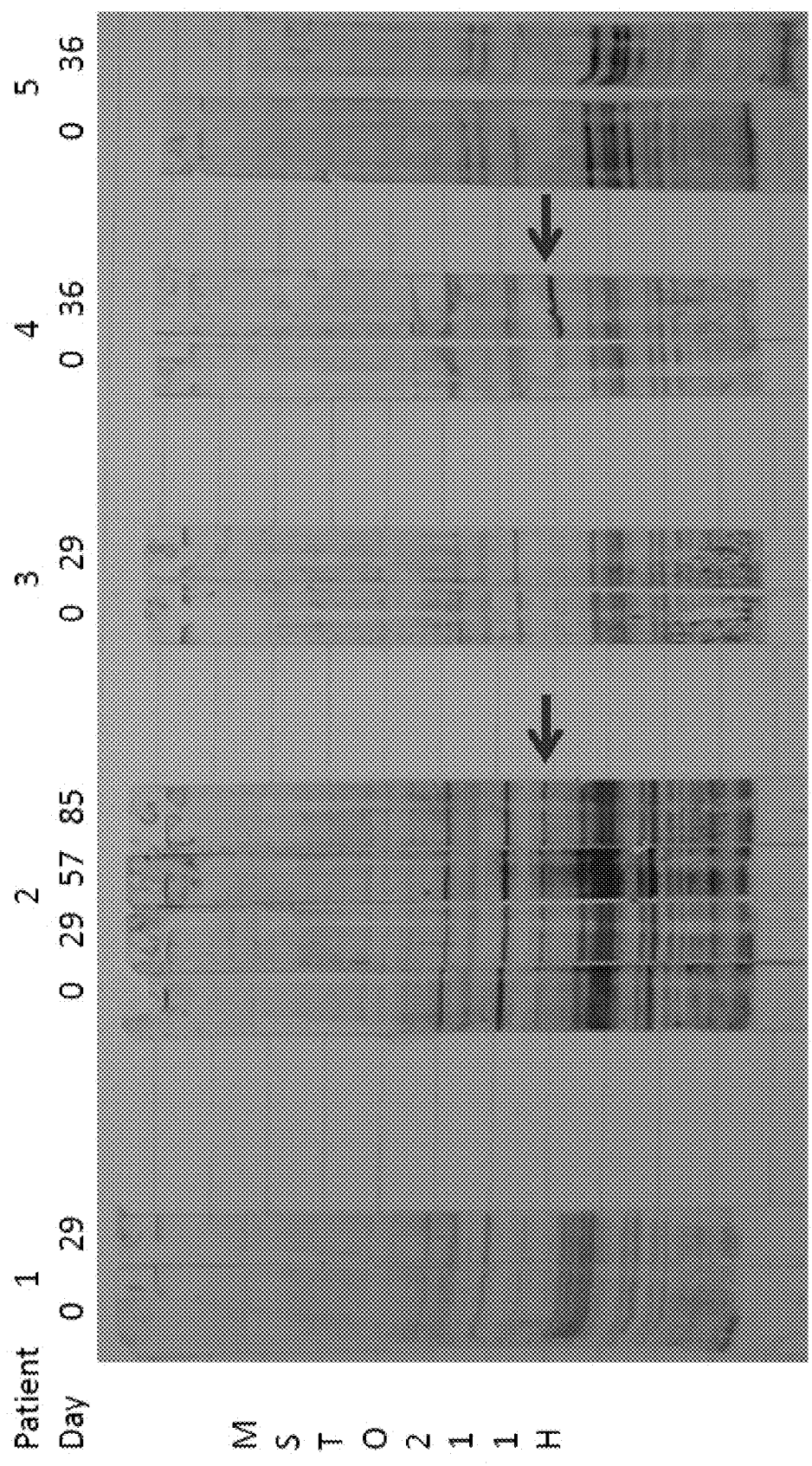
FIG. 16. Western Blot showing results for sera taken from patients 01, 02, 03, 04 and 05 against MSTO-211H cells. Arrows indicates novel IgG anti-tumor response.
Figure 17:
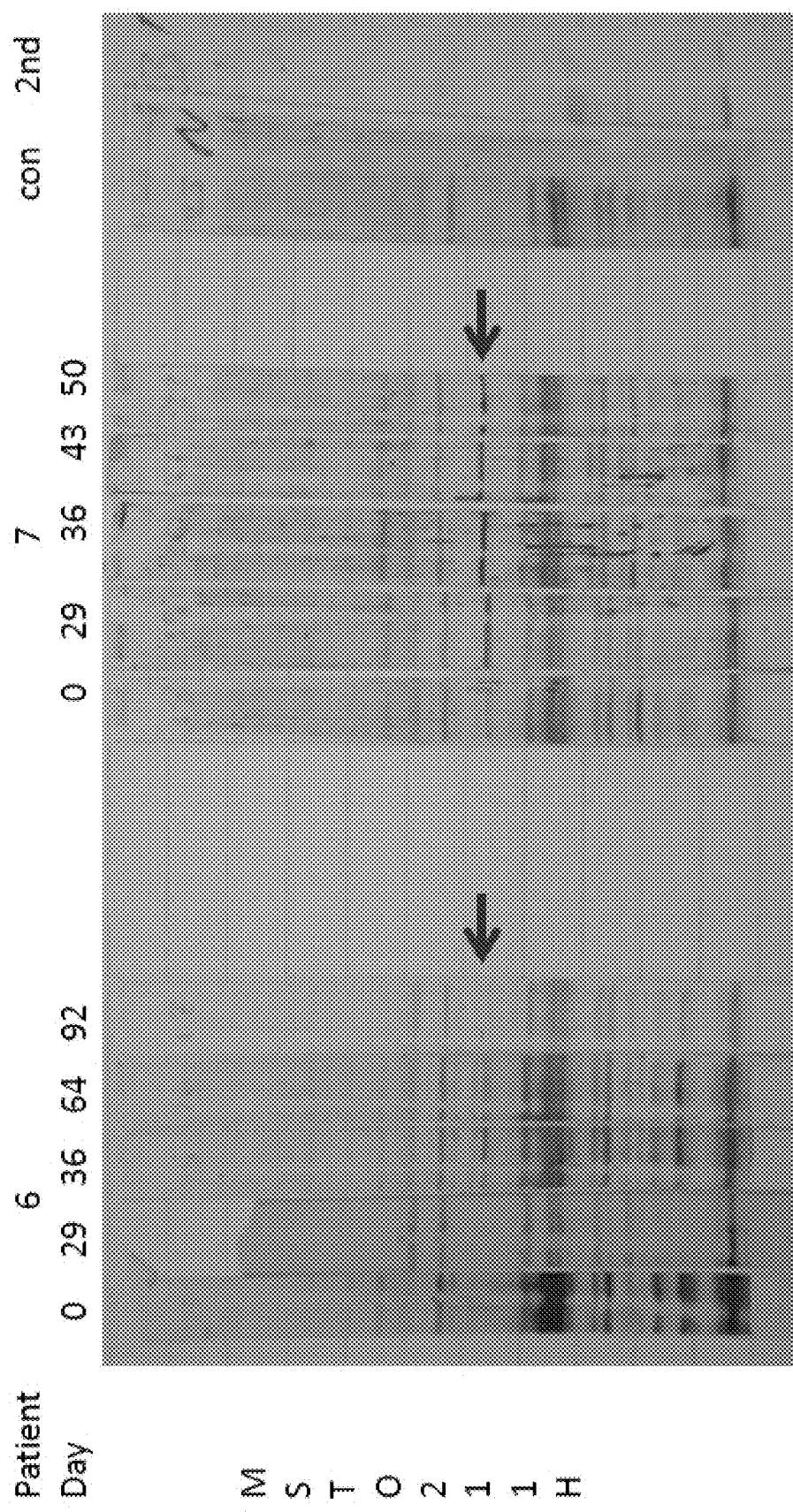
FIG. 17. Western Blot showing results for sera taken from patients 06 and 07 against MSTO-211H cells. Arrows indicates novel IgG anti-tumor response.
Figure 18:
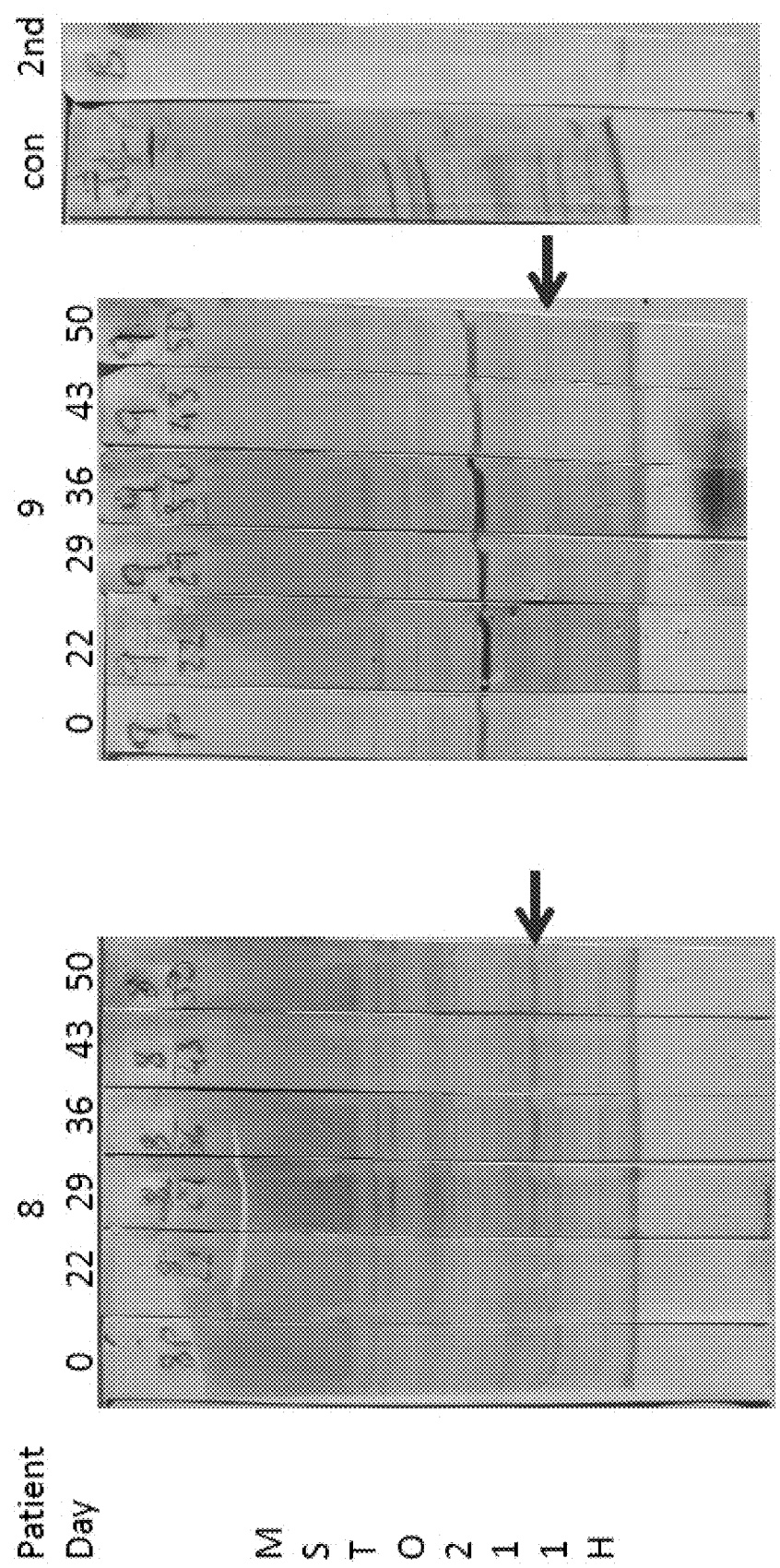
FIG. 18. Western Blot showing results for sera taken from patients 08 and 09 against MSTO-211H cells. Arrows indicates novel IgG anti-tumor response.

Analysis of plasma samples indicated a strong anti-HSV IgG responses post SEPREHVIR® administration, particularly after 2 and 4 doses. Intrapleural administration of SEPREHVIR® was found to induce a novel anti-tumor IgG response against an antigen present on MSTO-211H cells but not on SPC111 or HuH7 cells (FIG. 16-18) more so in patients receiving 4 doses of Seprehvir.

Thus, SEPREHVIR® has immunotherapeutic potential capable of inducing novel anti-tumor immune responses in patients. This result is consistent with induction of IgG B cells directed to tumour antigens released during Seprehvir oncolysis and stimulated through a Th1 response.

Example 3—Checkpoint Blockade Enhances Oncolytic Herpes Virotherapy in Immunosuppressive Sarcoma Models Most solid tumors are characterized by an immunosuppressive microenvironment, limiting the effectiveness of antitumor immunotherapeutics. Programmed cell death protein (PD)-1-mediated T cell suppression via engagement of its ligand, PD-L1, is of particular interest due to recent successes in selected adult cancers. The utility of PD1-directed therapy for pediatric cancers is unknown, especially given the paucity of mutations and thus infrequent neoantigens in many types of childhood tumors. Oncolytic virotherapy induces tumor shrinkage via a multistep process including direct tumor cell lysis, induction of cytotoxic or apoptosis-sensitizing cytokines, and induction of antitumor T cell responses. We have demonstrated that intratumoral injection of an oncolytic herpes virus induced growth delays and in some cases durable remissions in several mouse models of rhabdomyosarcoma. The effects were T cell-mediated, as surviving mice were resistant to tumor rechallenge and efficacy was lost in athymic nude hosts. We found these tumor models express PD-L1, suggesting that T cell checkpoints may in part limit virus-induced antitumor immunity. Here we show the implantable C57BL/6 rhabdomyosarcoma model, M3-9-M, showed a moderate response to single-agent Seprehvir (HSV1716), a virus currently in pediatric clinical trials (NCT00931931). Single-agent PD-1 blockade also showed moderate but significant tumor growth delay with no complete responses. Combining these two therapies together substantially prolonged overall survival with several complete responses post 60 days treatment. Interestingly, mice that received combination therapy showed more CD4+/CD8+ T cell recruitment to the tumor and displayed higher immune inflammatory responses and a less immunosuppressive microenvironment, as measured by the decreased proportion of CD4+/CD25+/Fox3P+ Tregs and suppressive cytokines. Overall, our data suggest the combination of PD-1 and oncolytic herpes virotherapy may be an effective treatment strategy for some cancers. Results are shown in FIG. 28-33.

We observed that: combination of oHSV treatment with immune checkpoint inhibitor anti-PD-1 significantly prolongs survival in both male to male and male to female rhabdomyosarcoma models; greater antitumor efficacy was observed in male to female murine rhabdomyosarcoma, suggesting that combination therapy favors more immunogenic microenvironments; combination therapy resulted in more CD4+/CD8+ T cell recruitment but did not affect in vivo virus activity; combination therapy induces more inflammatory responses and, although CD4+ T cell numbers increased, CD25+/CD4+Treg numbers were unchanged thus lowering the regulatory/suppressive tumor microenvironment.

Experimental Methods and Results

C57BL/6 mice were injected with 5×10$^6$ M3-9-M cells subcutaneously. Tumors were treated intra-tumorally (i.tu.) with Seprehvir when sizes reached 200~400 mm$^3$. Intraperitoneal (i.p.) injection of anti-PD-1 antibody [anti-PD1 antibody rat monoclonal RMP1-14 (AbCam plc)] were given twice a week after last dose of virus treatment. Tumor growth was monitored twice a week. Mice were sacrificed when tumors reached 2,500 mm$^3$ in volume or grew over 2 cm in length.

Figure 29:
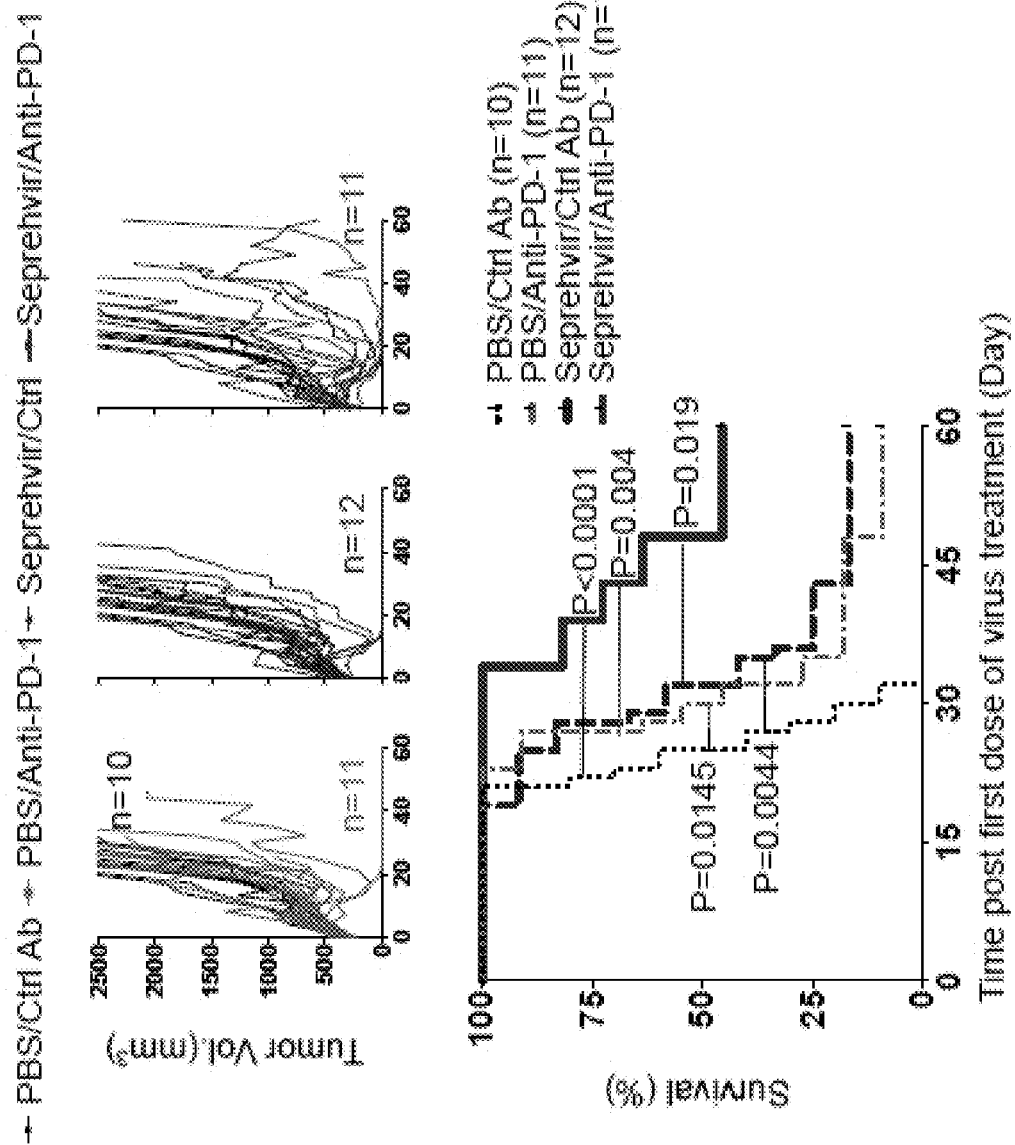
FIG. 29. Combination of Seprehvir with anti-PD-1 antibody significantly prolongs survival with several complete responses in male to female M3-9-M rhabdomyosarcoma tumor model. Female C57BL/6 mice were injected with $5\times10^6$ M3-9-M cells subcutaneously. The effects of Seprehvir plus anti-PD-1 blockade on antitumor efficacy were evaluated by measuring tumor volumes over time. Survival data were evaluated for statistical significance with Log-rank (Mantel-Cox) test.

Female C57BL/6 mice were injected with 5×10$^6$ M3-9-M cells subcutaneously. The effects of Seprehvir plus anti-PD-1 blockade on antitumor efficacy were evaluated by measuring tumor volumes over time. Survival data were evaluated for statistical significance with Log-rank (Mantel-Cox) test. FIG. 29 shows the combination of Seprehvir and anti-PD-1 antibody to significantly prolong survival with several complete responses in the male to female M3-9-M tumor model.

Figure 30:
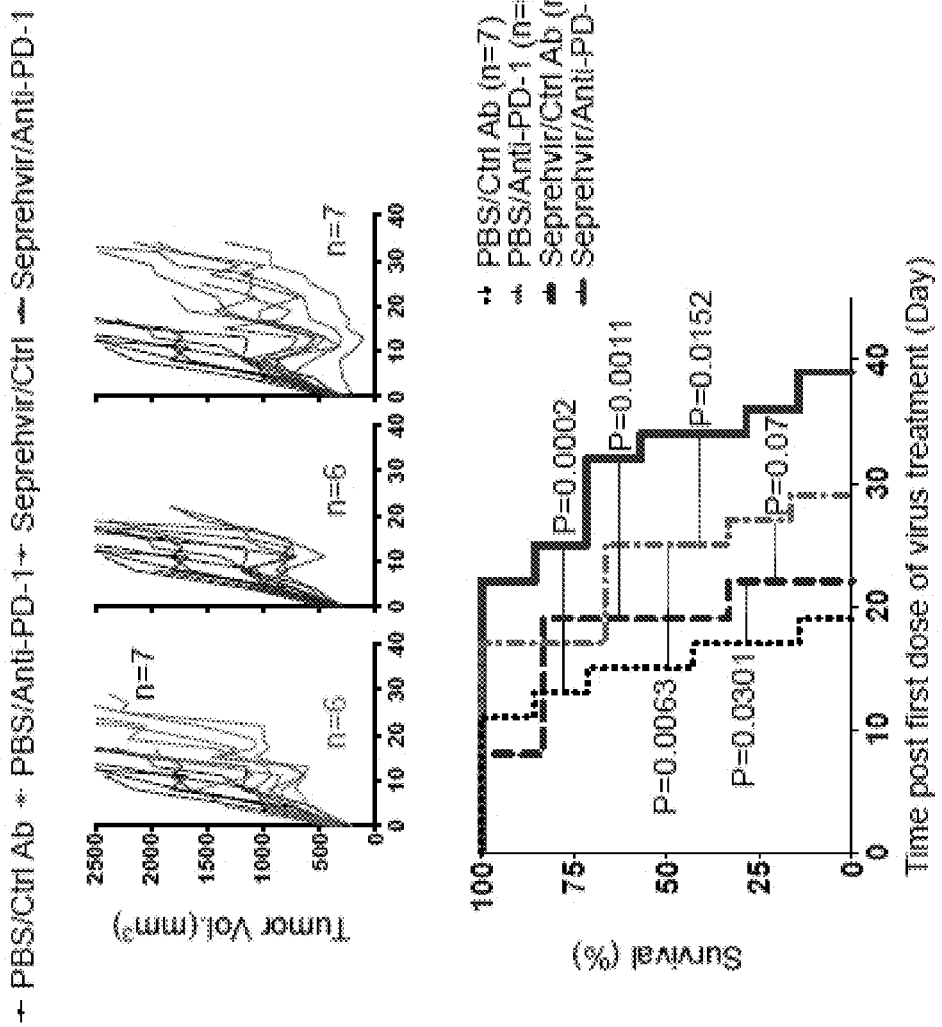
FIG. 30. Combination of Seprehvir with anti-PD-1 antibody significantly prolongs survival in less immunogenic male to male M3-9-M tumor model. Male C57BL/6 mice were injected with $5\times10^6$ M3-9-M cells subcutaneously. The effects of Seprehvir plus anti-PD-1 blockade on antitumor efficacy were evaluated by measuring tumor volumes over time. Survival data were evaluated for statistical significance with Log-rank (Mantel-Cox) test. Upper left chart: PBS/Ctrl Ab (n=7) and PBS/Anti-PD-1 antibody (n=6); Upper middle chart: PBS/Ctrl Ab (n=7) and Seprehvir/Ctrl (n=6); Upper right chart: PBS/Ctrl Ab (n=7) and Seprehvir/Anti-PD-1 antibody (n=7). Lower chart: PBS/Ctrl Ab (n=7)—dotted line, left-hand side; PBS/Anti-PD-1 antibody (n=6)—dashed and dotted line; Seprehvir/Ctrl (n=6)—dashed line; Seprehvir/Anti-PD-1 antibody (n=7)—solid line, right-hand side.

Male C57BL/6 mice were injected with 5×10$^6$ M3-9-M cells subcutaneously. The effects of Seprehvir plus anti-PD-1 blockade on antitumor efficacy were evaluated by measuring tumor volumes over time. Survival data were evaluated for statistical significance with Log-rank (Mantel-Cox) test. FIG. 30 shows the combination of Seprehvir and anti-PD-1 antibody to significantly prolong survival in the less immunogenic male to male M3-9-M tumor model.

Figure 31:
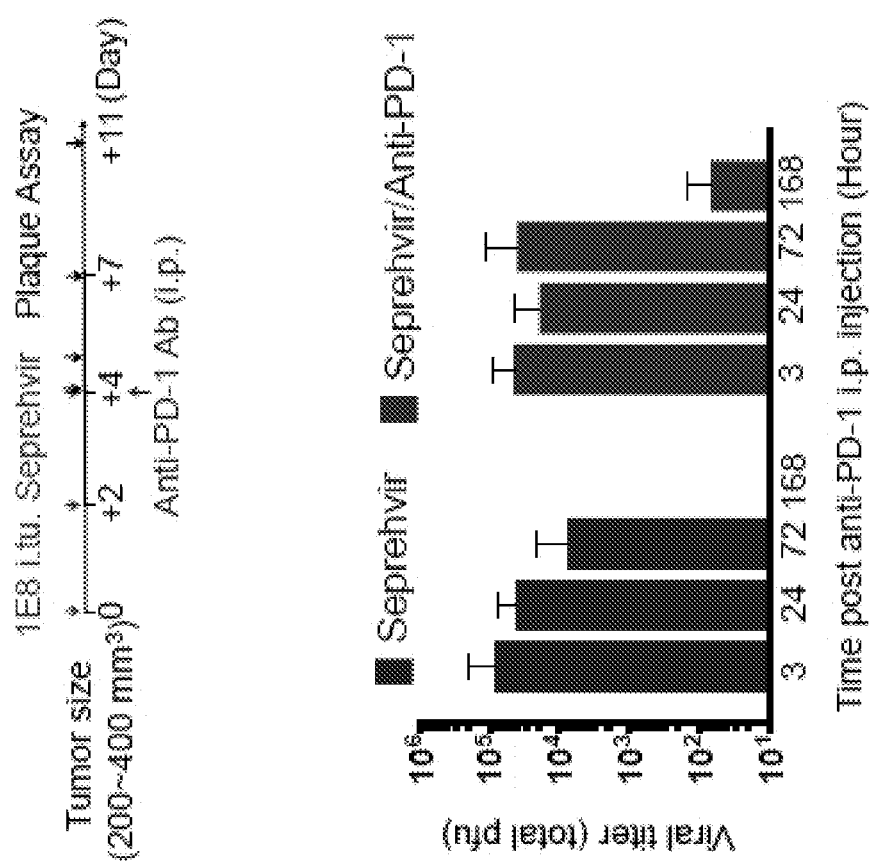
FIG. 31. Checkpoint inhibition does not significantly alter intra-tumoral viral kinetics. Female M3-9-M tumor-bearing mice were treated with three doses of $10^8$ pfu of Seprehvir intra-tumorally (i.tu.) followed by intra-peritoneal (i.p.) injection of anti-PD-1 or control antibody. Tumors were harvested 3, 24, 72 and 168 hours after intra-peritoneal antibody injection for plaque assay. Data are expressed as total plaque-forming units (pfu) per tumor.

Female M3-9-M tumor-bearing mice were treated with three doses of 10$^8$ pfu of Seprehvir intra-tumorally (i.tu.) followed by intra-peritoneal (i.p.) injection of anti-PD-1 or control antibody. Tumors were harvested 3, 24, 72 and 168 hours after intra-peritoneal antibody injection for plaque assay. Data are expressed as total plaque-forming units (pfu) per tumor. FIG. 31 shows checkpoint inhibition does not significantly alter intra-tumoral viral kinetics.

Figure 32A:
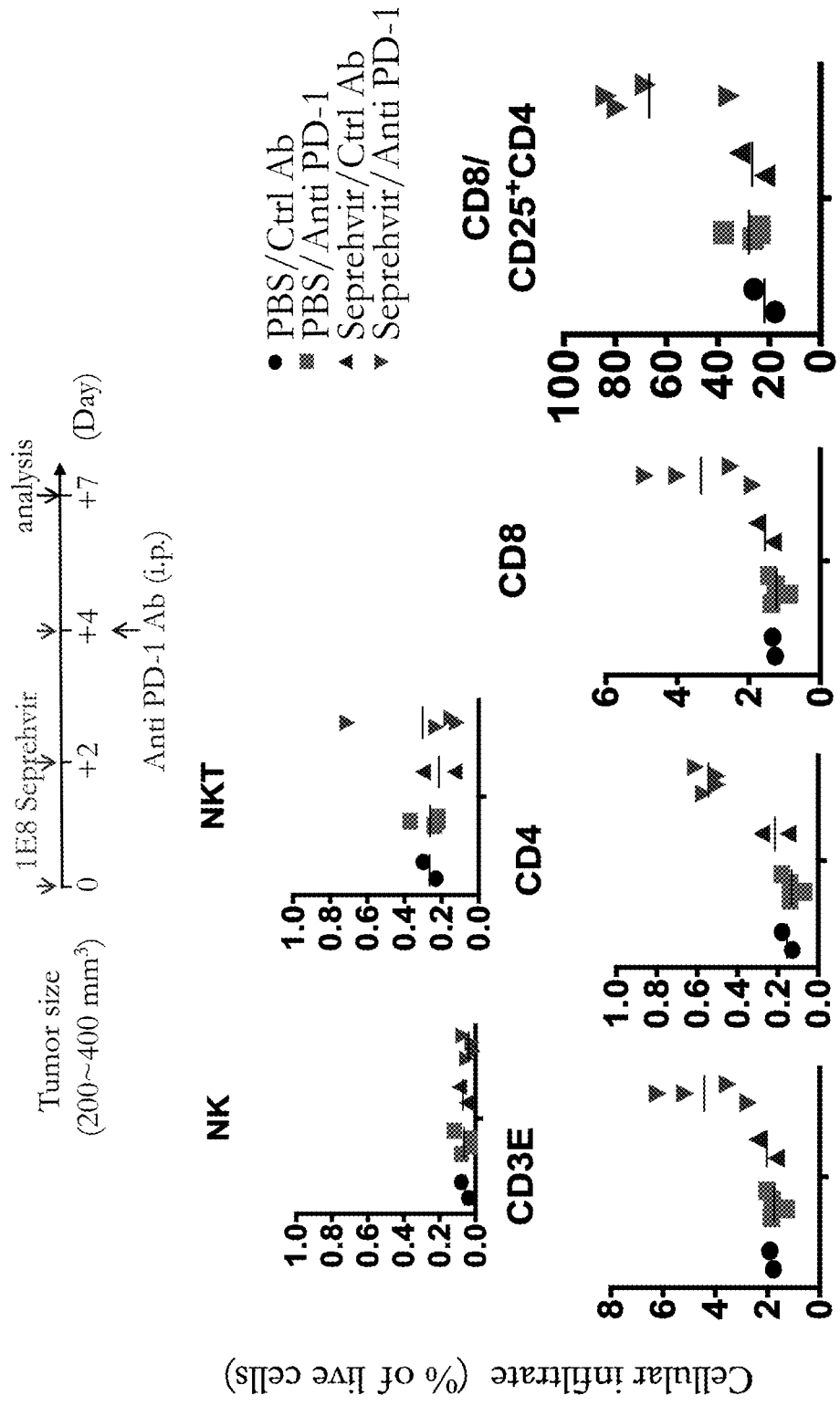
FIG. 32A shows that combination therapy induces more CD4+ and CD8+ T cells.
Figure 32B:
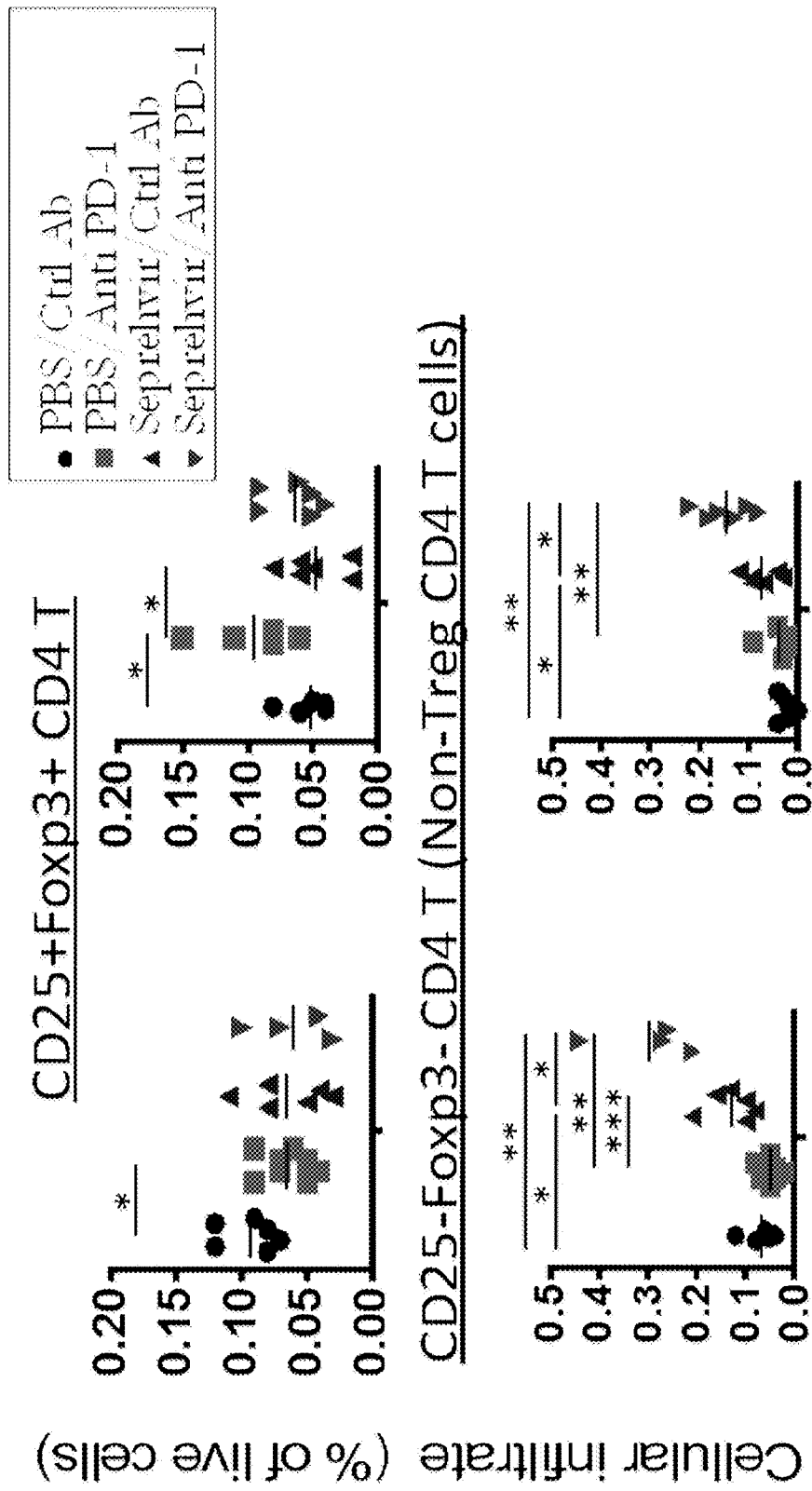
FIG. 32B shows that the increase in CD4+ T cells in both female (left) and male (right) is not due to higher numbers of CD25+CD4+ Treg cells.

Female M3-9-M tumor-bearing mice received three doses of intra-tumoral (i.tu.) Seprehvir injection followed by intra-peritoneal (i.p.) injection of anti-PD-1 or control antibody. Immune cell infiltrates in tumors were evaluated by flow cytometry analyses 72 hours post intra-peritoneal antibody injection. FIGS. 32A and 32B shows combination therapy induces more CD25+CD8+ memory T cells but less CD25+ CD4+ Treg cells.

Figure 33:
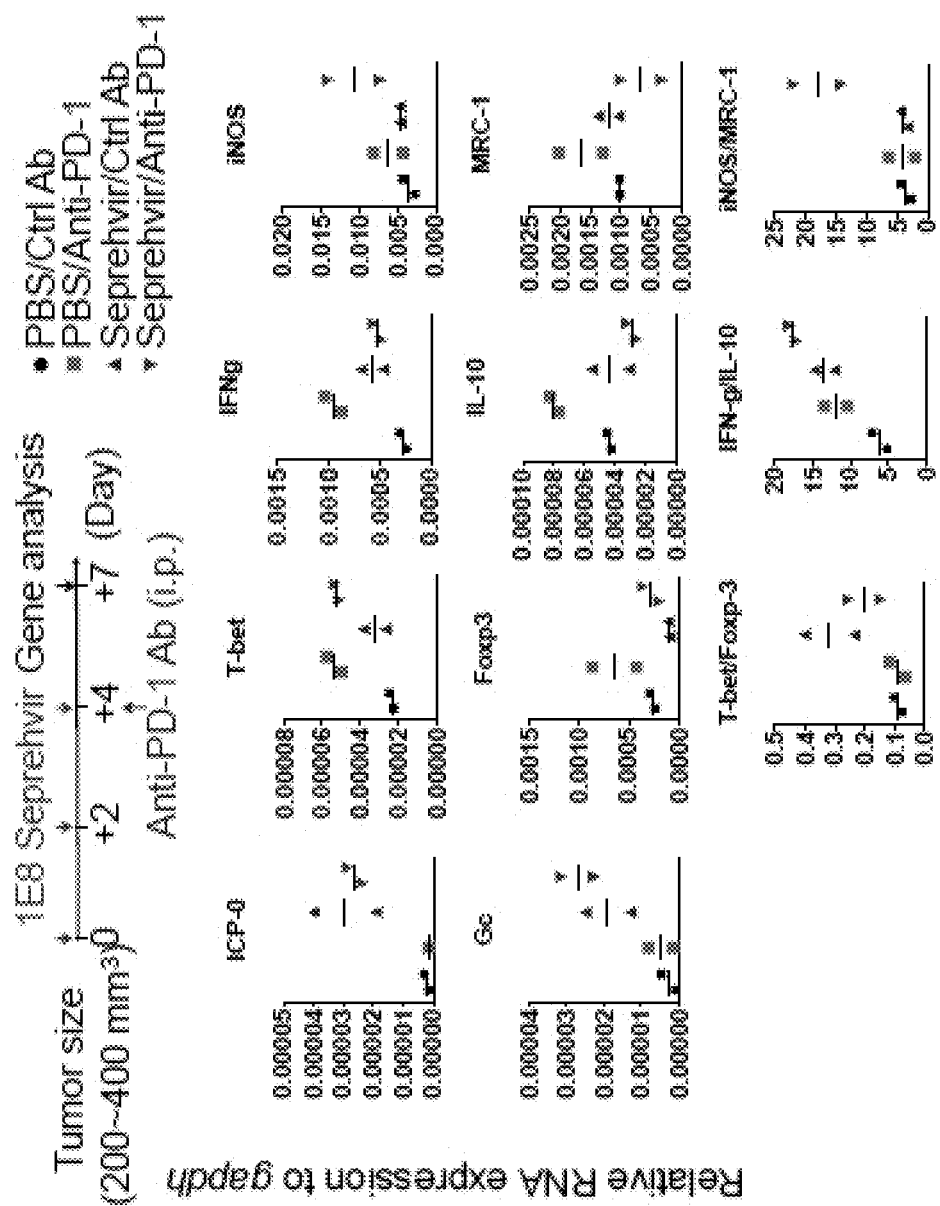
FIG. 33. Combination therapy induces higher inflammatory gene expression and lower immune suppressive gene expression. Female M3-9-M tumor-bearing mice received three doses of intra-tumoral (i.tu.) Seprehvir injection followed by intra-peritoneal (i.p.) injection of anti-PD-1 or control antibody. Tumors were harvested 72 hours post intra-peritoneal antibody injection. T-bet (Th-1-related gene), Foxp3 (Treg-related gene), IFNγ, IL-10, iNOS (M1 macrophage-related gene) and MRC-1 (M2 macrophage-related gene) were quantified by real-time. Date are represented as relative RNA expression to gapdh. In each chart, columns from left to right are PBS/Control antibody, PBS/Anti-PD-1 antibody, Seprehvir/Control antibody and Seprehvir/Anti-PD-1 antibody.
Figure 34:
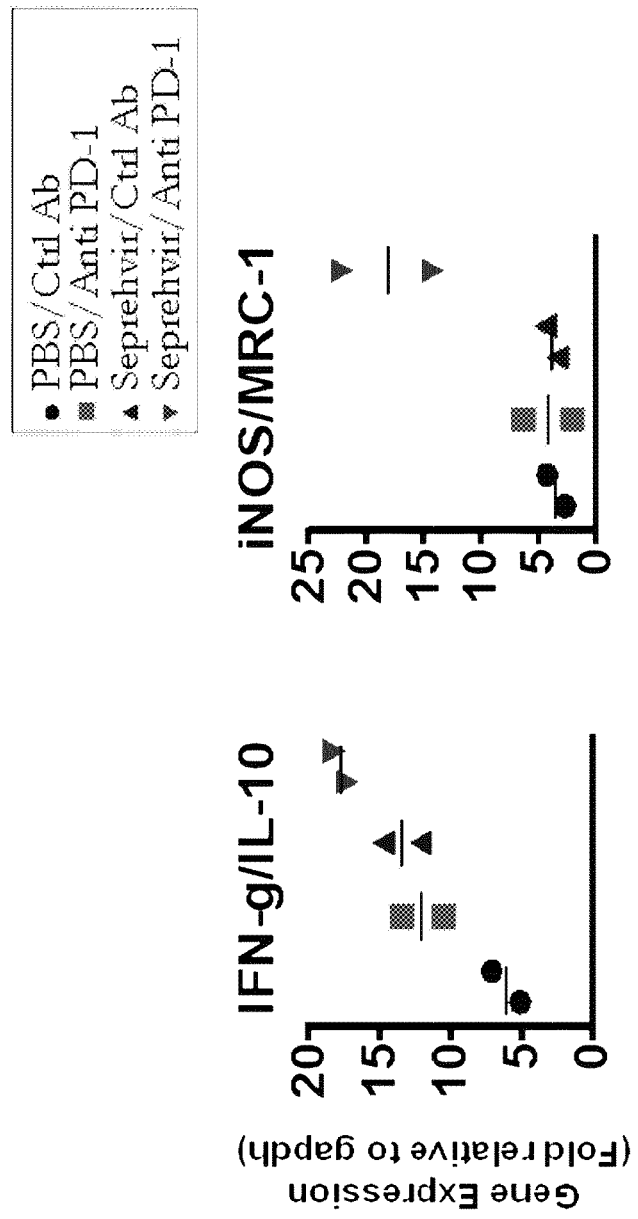
FIG. 34. Tumour microenvironment is remodeled to Th1 away from Th2 by Seprehvir and combination with anti-PD-1. IFNγ and iNOS are used as Th1 markers and their proportion, relative to the Th2 markers IL-10 and MRC-1 are significantly increased by Seprehvir+anti-PD-1.
Figure 35:
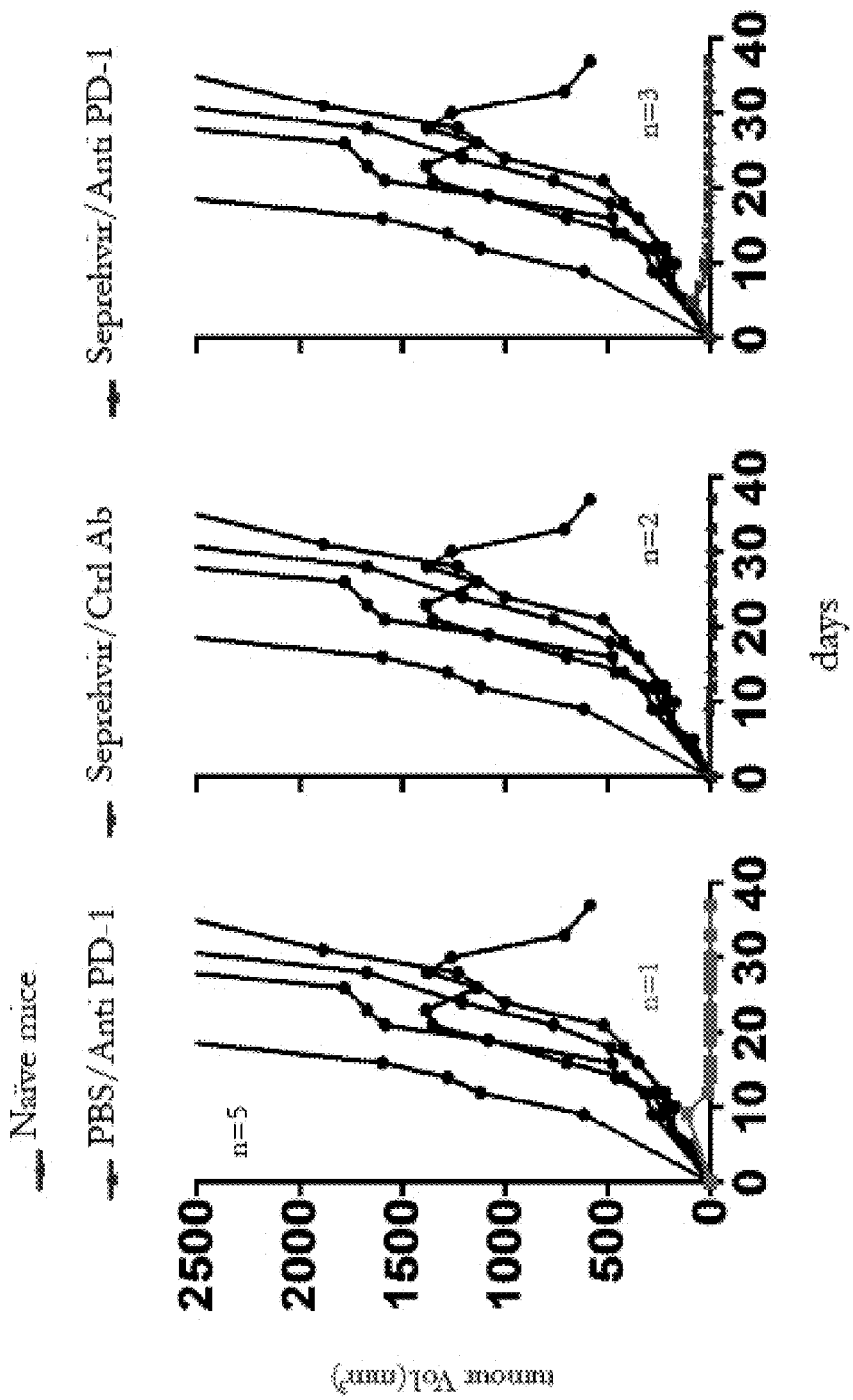
FIG. 35. Charts showing results of re-challenge experiment in which mice cured of xenograft tumor are vaccinated against tumor re-challenge via development of memory anti-tumor immunity. Cured mice from FIG. 30 (n=1 for anti-PD-1 alone, n=2 for Seprehvir alone and n=3 for the combination) were rechallenged by subcutaneous implantation of M3-9-M cells. Tumors failed to form in any animal but developed in 5/5 age-matched naive mice.
Figure 36:
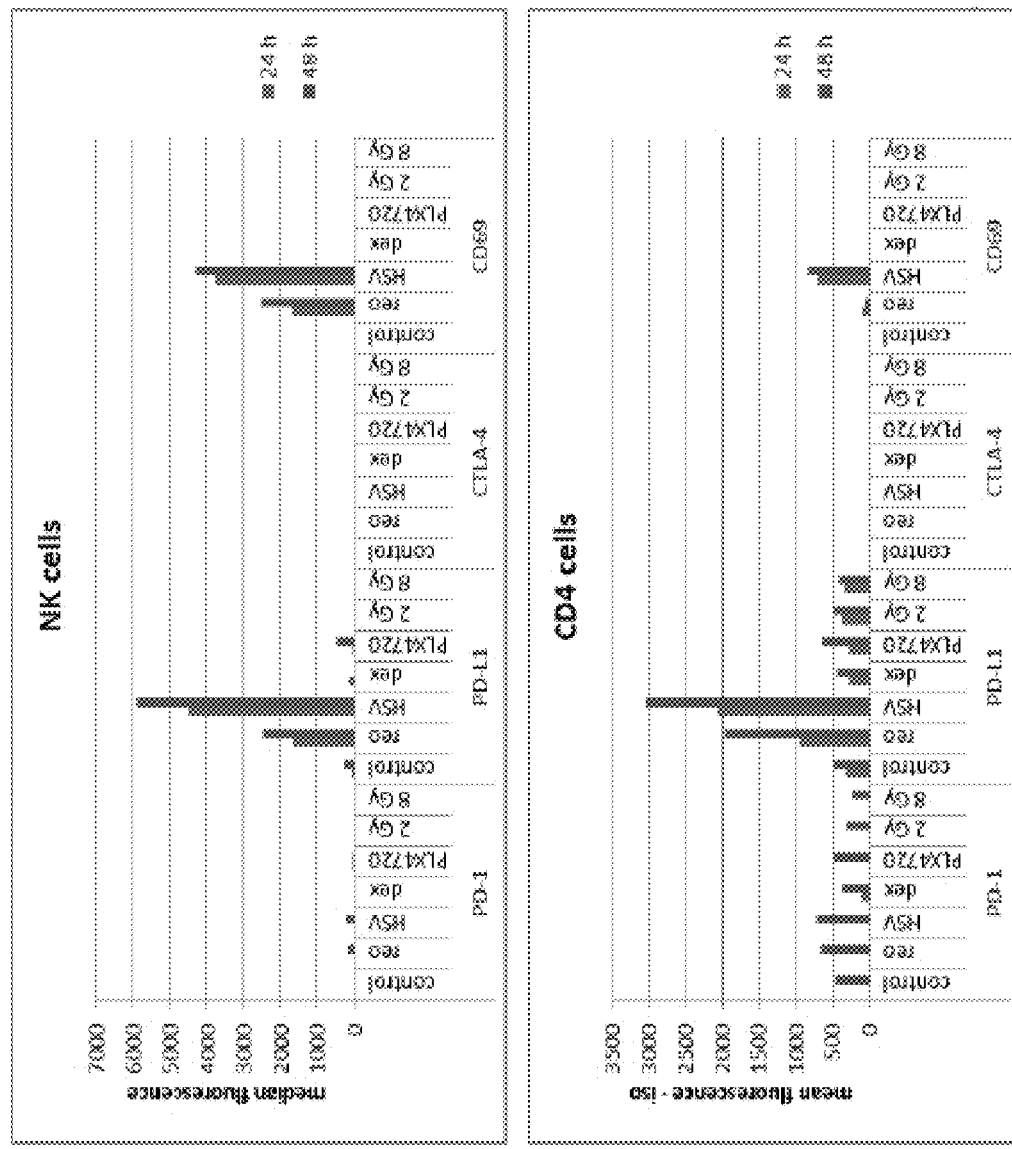
FIG. 36. Seprehvir directly interacts and activates human PBMCs. Charts showing phenotypes of NK and CD4+ cells after treatment with reovirus (reo), HSV1716, steroid or Braf inhibitor or X-ray radiation treatment. PBMC were isolated from leukapheresis cones, seeded at $2\times10^6$ cells/ml and treated±reovirus or HSV1716 (MOI 1); dexamethasone (0.2 mM); PLX4720 (2 µM); 2 Gy XRT; 8 Gy XRT. After 24 or 48 h culture the cells were harvested, stained for the markers indicated and analyzed by FACS. For each entry 24 h data left bar shows 24 h data and right bar shows 48 h data.
Figure 37:
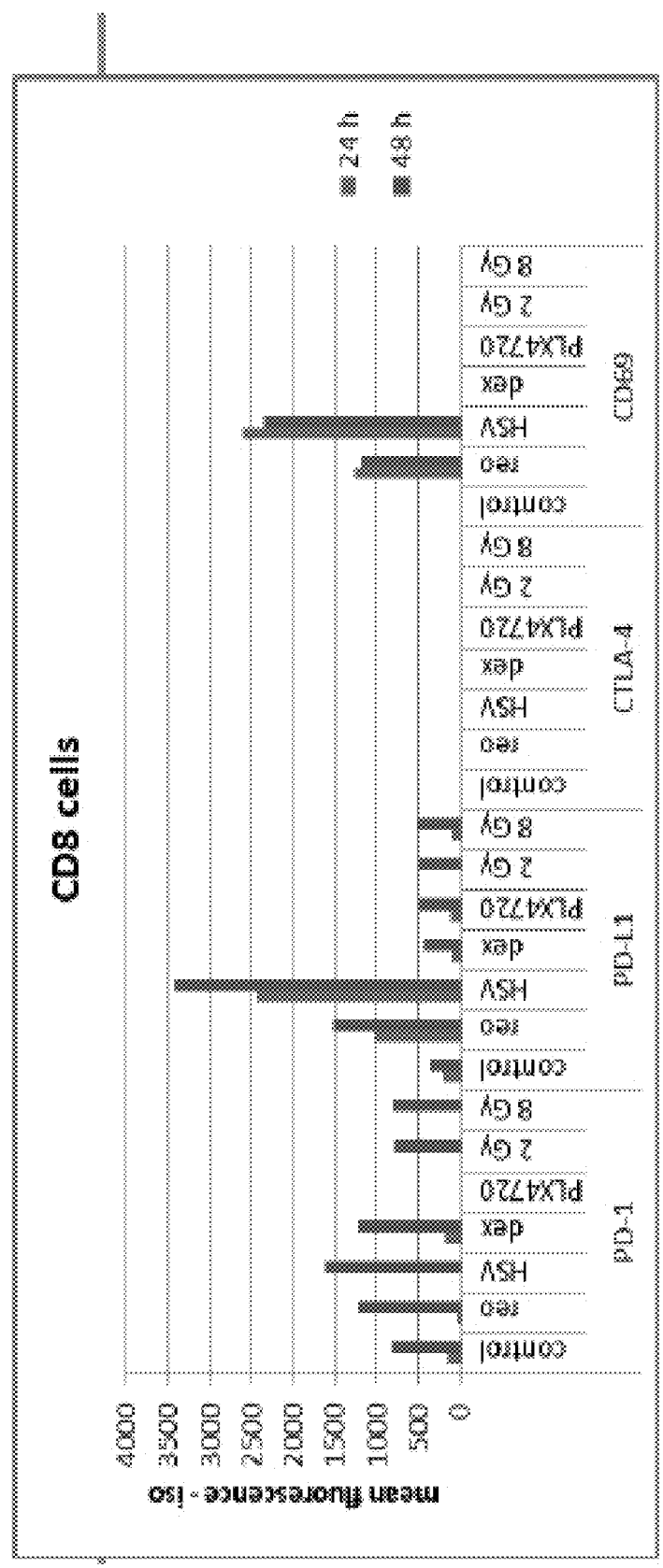
FIG. 37. Seprehvir directly interacts and activates human PBMCs. Charts showing phenotypes of CD8+ cells after treatment with reovirus (reo), HSV1716, steroid or Braf inhibitor or X-ray radiation treatment. PBMC were isolated from leukapheresis cones, seeded at $2\times10^6$ cells/ml and treated±reovirus or HSV1716 (MOI 1); dexamethasone (0.2 mM); PLX4720 (2 µM); 2 Gy XRT; 8 Gy XRT. After 24 or 48 h culture the cells were harvested, stained for the markers indicated and analyzed by FACS. For each entry 24 h data left bar shows 24 h data and right bar shows 48 h data.
Figure 38:
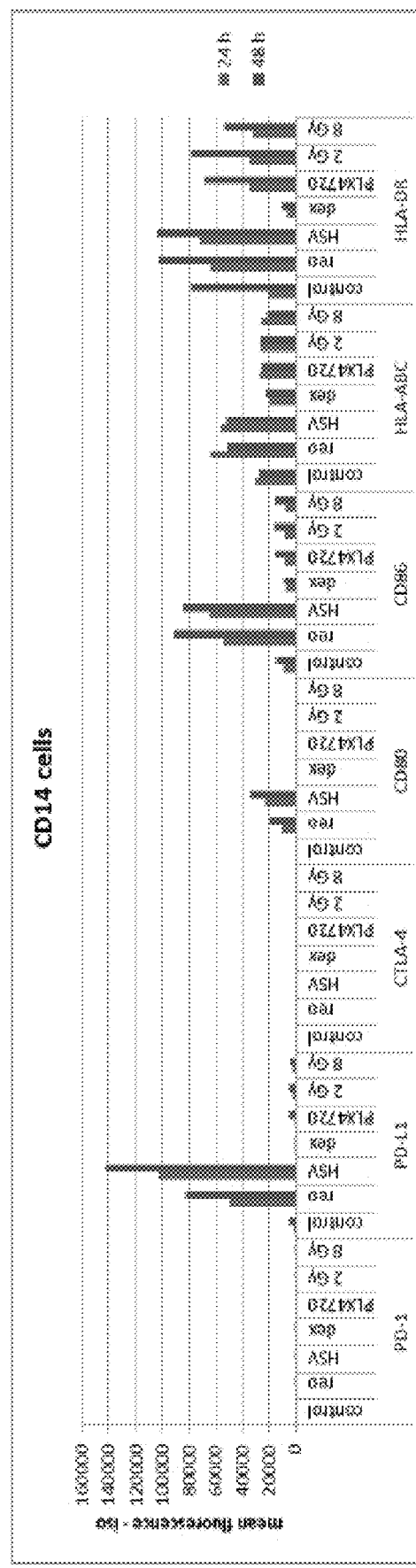
FIG. 38. Seprehvir directly interacts and activates human PBMCs. Charts showing phenotypes of CD14+ cells after treatment with reovirus (reo), HSV1716, steroid or Braf inhibitor or X-ray radiation treatment. PBMC were isolated from leukapheresis cones, seeded at $2\times10^6$ cells/ml and treated±reovirus or HSV1716 (MOI 1); dexamethasone (0.2 mM); PLX4720 (2 µM); 2 Gy XRT; 8 Gy XRT. After 24 or 48 h culture the cells were harvested, stained for the markers indicated and analyzed by FACS. For each entry 24 h data left bar shows 24 h data and right bar shows 48 h data.
Figure 39A:
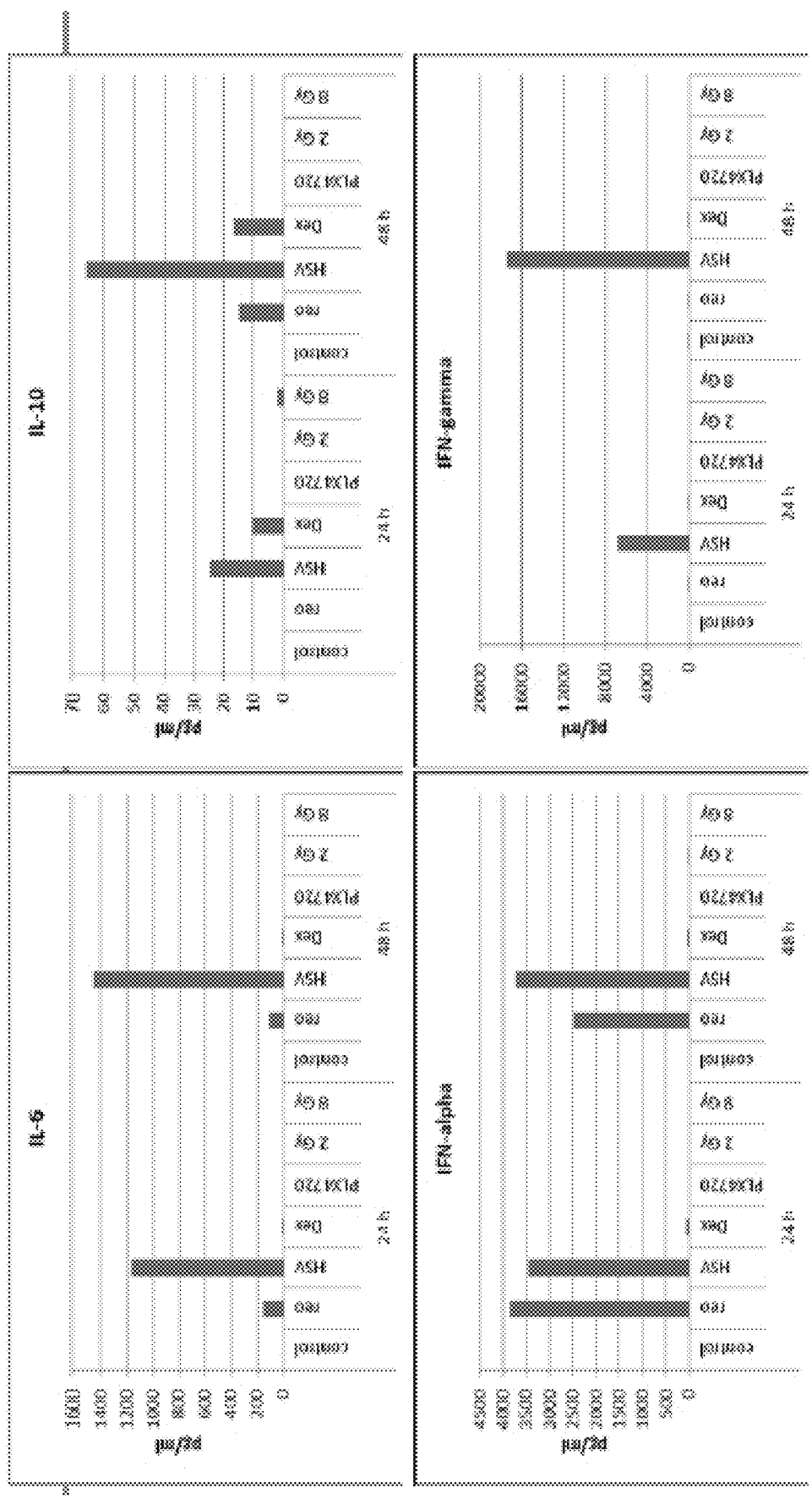
FIG. 39A shows expression of IL-6, IL-10, IFNα, and IFNγ in PBMC after treatment with reovirus (reo), HSV1716, steroid or Braf inhibitor or X-ray radiation treatment.
Figure 39B:
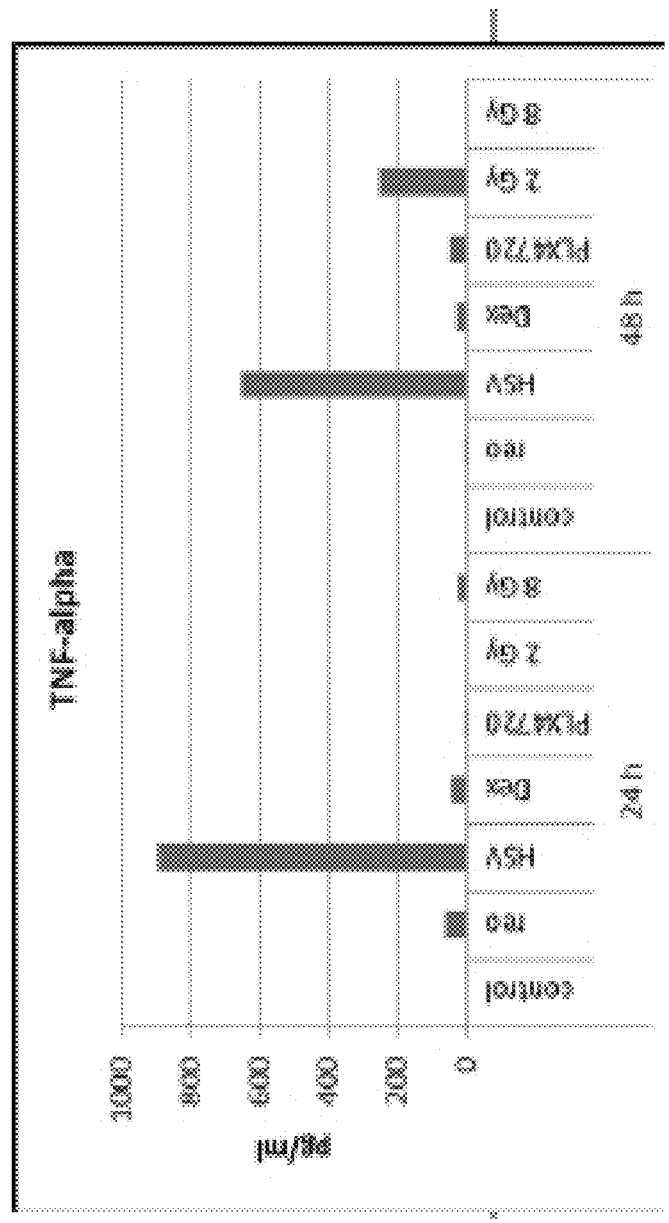
FIG. 39B shows expression of TNFα in PBMC after treatment with reovirus (reo), HSV1716, steroid or Braf inhibitor or X-ray radiation treatment.
Figure 40:
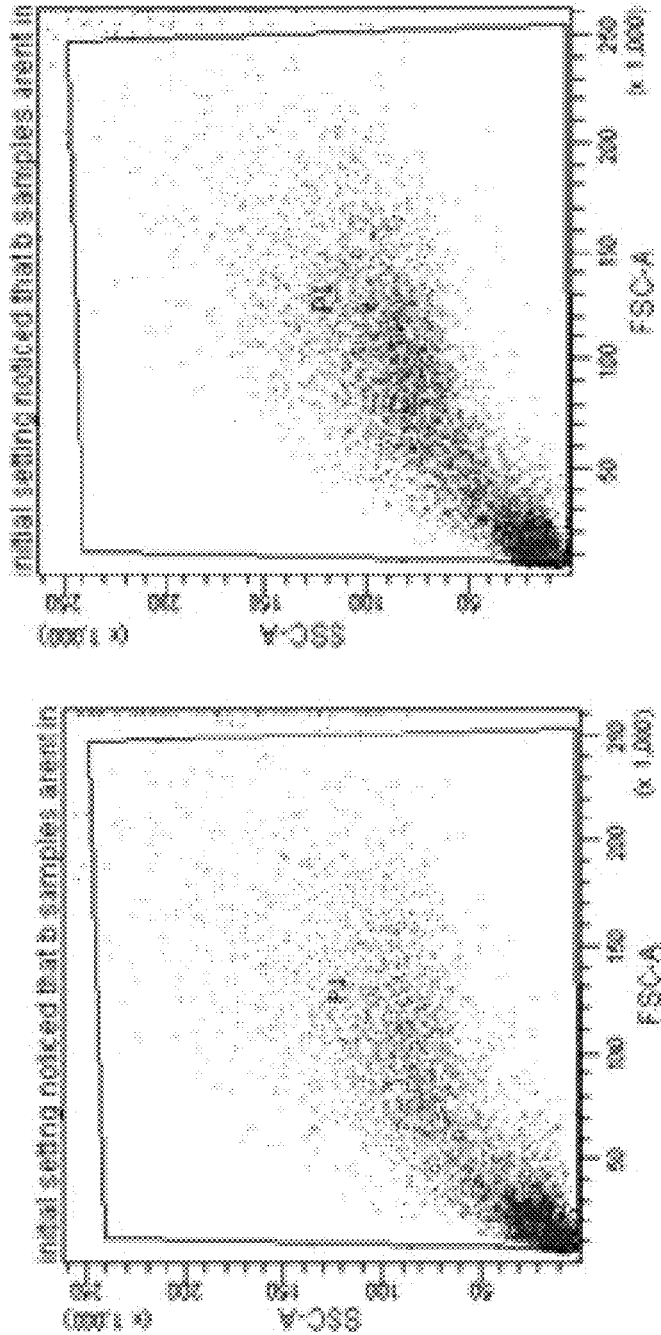
FIG. 40. Chart showing FACs analysis and table showing GFP expression in tumor cell lines One58 (human mesothelioma), Ovcar3 (human ovarian cancer), T98 (human glioblastoma multiforme), Ln229 (human glioma). Human cancer cell lines were infected with HSV1716gfp (HSV1716 modified to express GFP) at moi 0.5 and cultured for 24 hours before addition of $10^6$ human PBMCs. After 24 hours culture, PBMCs were decanted and cultured for 24-48 hours before analysed for expression of GFP. HSV1716 was found to infect and transfer to a monocyte/macrophage rich subset of PBMCs.
Figure 41:
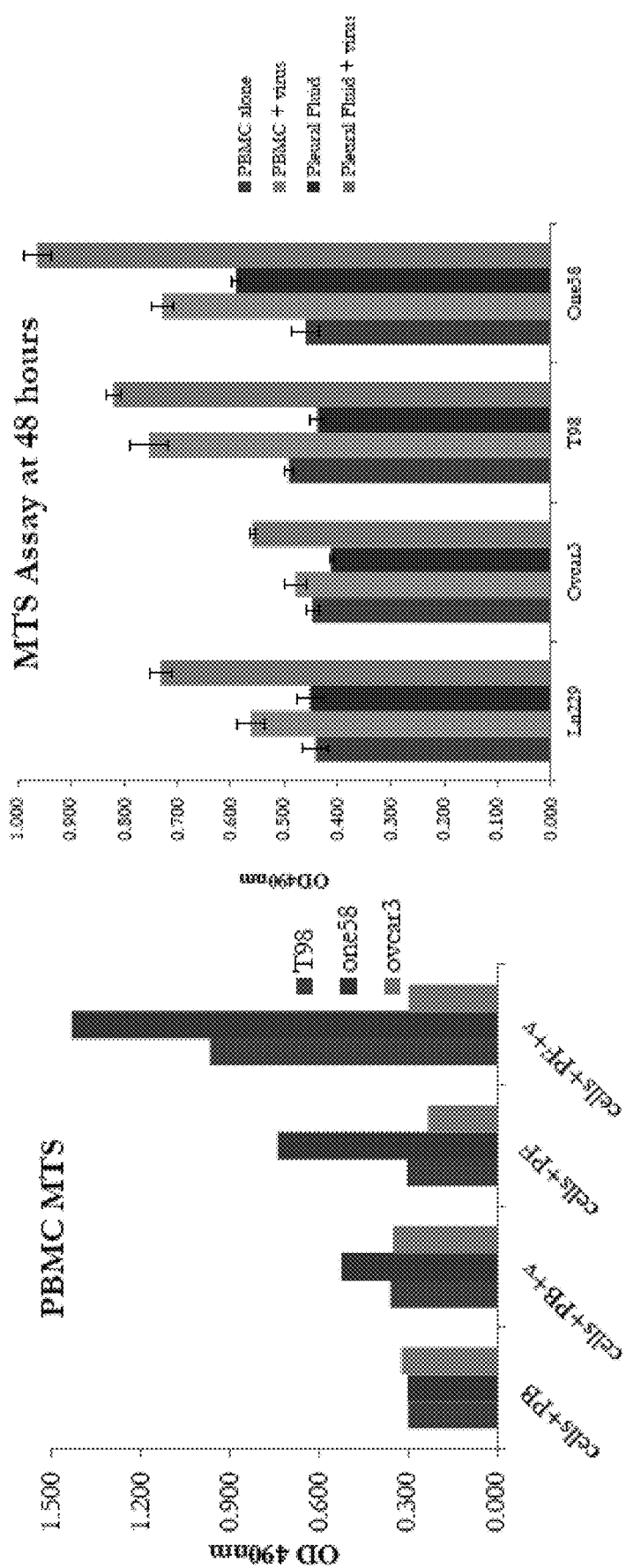
FIG. 41. HSV1716 infected human cancer cell lines stimulate PBMC and Pleural Fluid Mononuclear Cell (PFMC) growth. Two separate experiments are shown and PBMC/PFMC were decanted and cultured for 48 hours before MTS assay. Left chart, experiment 1 shows result of MTS assay of PBMC/PFMC when added to human cancer cell lines infected with HSV1716; in each entry from left to right bars indicate T98 cells, One58 cells and Ovcar3 cells +/- virus infection. Right chart shows experiment 2 result of MTS assay following treatment of tumor cells lines Ln229, Ovcar3, T98 and One58 with HSV1716 followed by the addition of PBMC/PFMC; in each entry, from left to right bars indicate PBMC alone, PBMC+HSV1716, pleural fluid mononuclear cells, pleural fluid mononuclear cells+ HSV1716.
Figure 42:
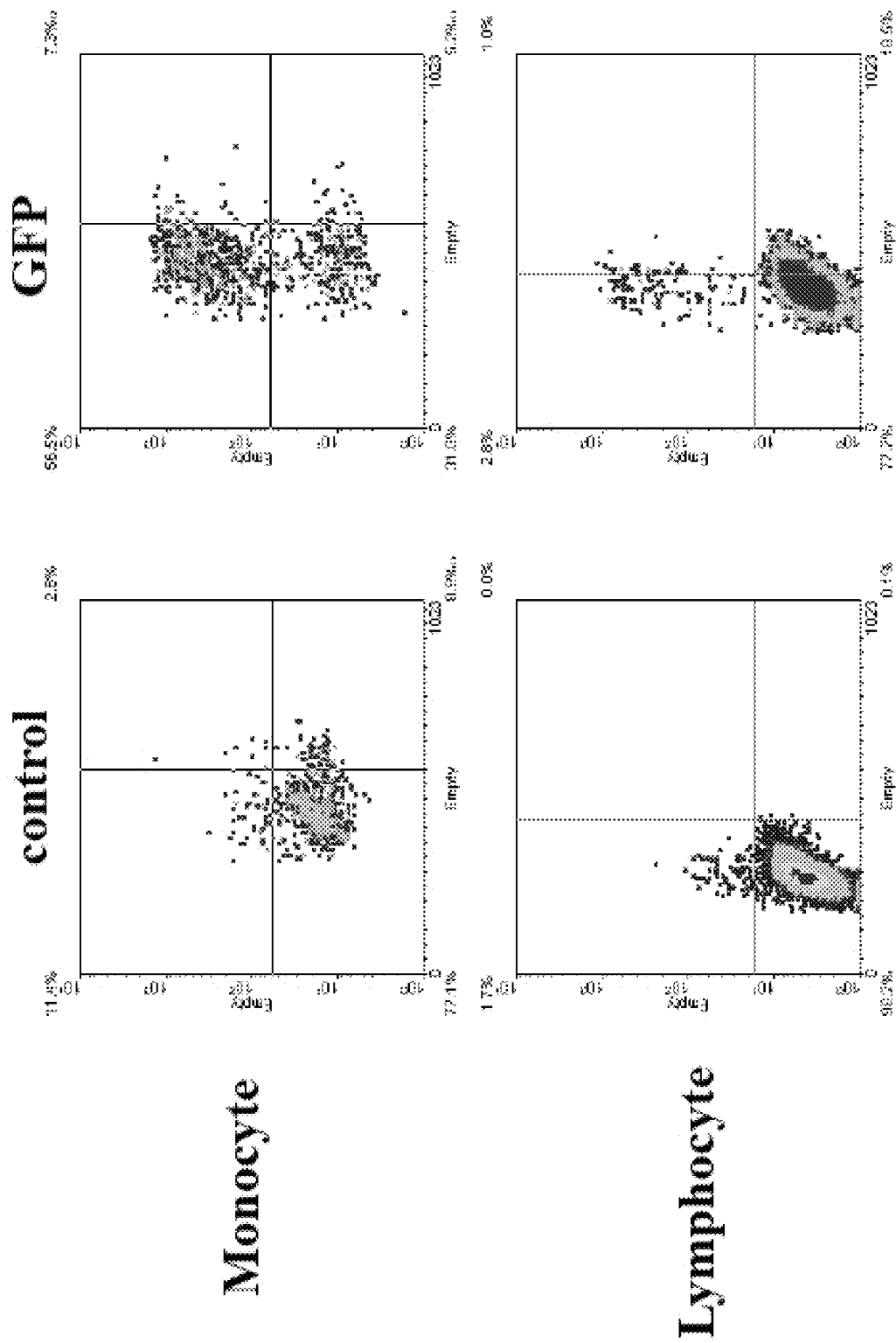
FIG. 42. Seprehvir preferentially infects monocytes in human PBMCs. Charts results of FACs analysis for human monocytes and lymphocytes infected with HSV1716gfp.

Female M3-9-M tumor-bearing mice received three doses of intra-tumoral (i.tu.) Seprehvir injection followed by intra-peritoneal (i.p.) injection of anti-PD-1 or control antibody. Tumors were harvested 72 hours post intra-peritoneal antibody injection. T-bet (Th-1-related gene), Foxp3 (Treg-related gene), IFNγ, IL-10, iNOS (M1 macrophage-related gene) and MRC-1 (M2 macrophage-related gene) were quantified by real-time PCR. FIG. 33 shows combination therapy induces higher inflammatory gene expression and lower immune suppressive gene expression. Data are represented as relative RNA expression to gapdh.

Combination of oncolytic HSV treatment with immune checkpoint inhibitor anti-PD-1 significantly prolonged survival in both male to male and male to female rhabdomyosarcoma models.

Greater antitumor efficacy was observed in male to female murine rhabdomyosarcoma, suggesting that combination therapy favors more immunogenic microenvironments.

Combination therapy did not result in more T cell recruitment or affect in vivo virus activity.

Combination therapy induces more inflammatory responses with less immune regulatory/suppressive responses.

Example 4—Seprehvir Directly Polarises PBMCs Phenotype to Th1

When human PBMCs were exposed directly to Seprehvir, the virus induced a marked Th1 phenotype with increased production of IFNα and IFNγ and TNFα. IL-6 and regulatory IL-10 production were also stimulated and HSV was more effective than Reovirus, dexamethasone, PLX4720 and ionising radiation. Thus Seprehvir could influence these cells directly following their recruitment into the tumour microenvironment. Exposure of PBMCs to Seprehvir upregulated the expression of immune checkpoints in many different subsets including NK, CD4+, CD8+ and CD14+ (monocytes) cells (FIGS. 36 to 39).

Example 5—Seprehvir Infects and Polarises Human Macrophages Potentially Inducing a Th1 Response Directly in Human PBMCs On Day 7 following infection with HSV1716 expressing gfp, human monocyte-derived macrophages demonstrated a significant increase in infection which correlated with an increase in cell death.

Figure 43:
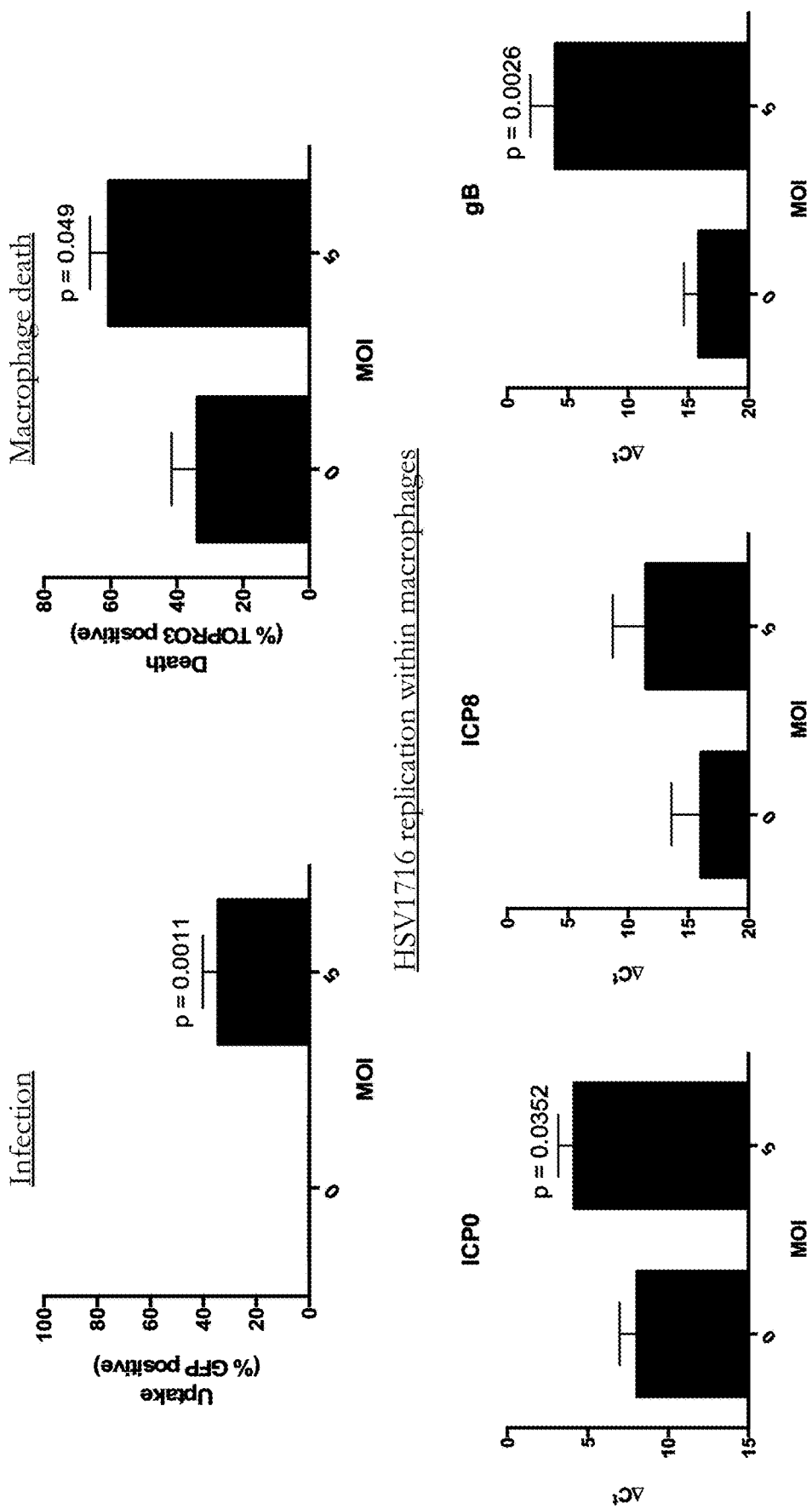
FIG. 43. Seprehvir infects and polarises human macrophages. Charts show infection of macrophages with HSV1716gfp, macrophage cell death, expression of viral genes in macrophages: ICP0, ICP8, gB. All data were normalised to the house keeping gene GAPDH and 6 independent experiments were performed (n=6). X-axis 0=macrophages (no virus).

Infection was demonstrated via investigation of the expression of viral proteins immediate early (ICP0) and late (gB) genes indicating significant gene expression in macrophages (FIG. 43).

Mechanism of Cell Death in Human Macrophages

HSV1716 kills macrophages via apoptosis and in a Fas dependent manner with both FasL and Bcl-2 gene expression up-regulated 24 hours after infection with HSV1716 at an MOI of 5.

Figure 44:
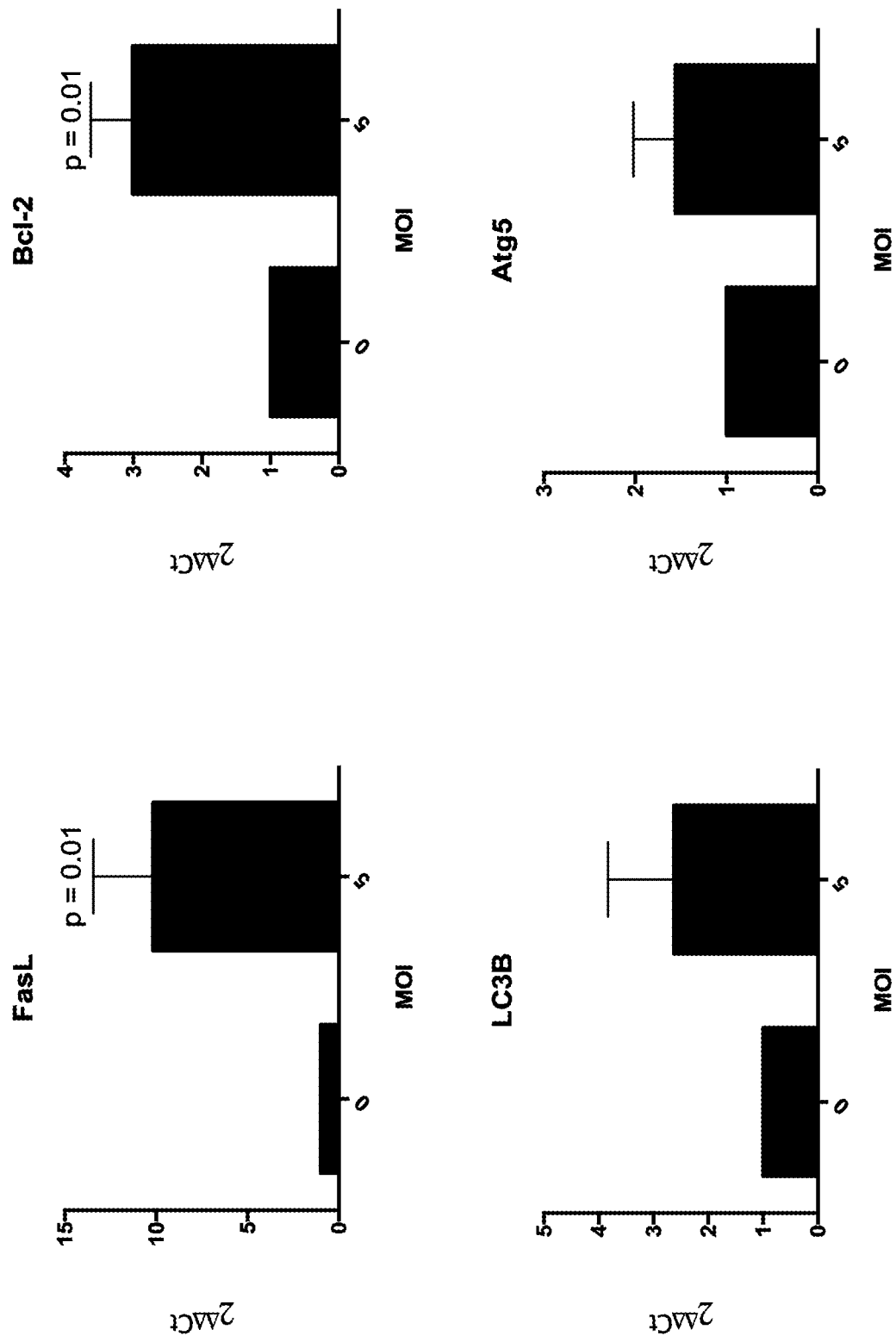
FIG. 44. Charts showing expression of FasL, Bcl-2, LC3B and Atg5 in macrophages 24 hours after infection with HSV1716 at moi of 5. All data were normalised to the house keeping gene GAPDH and 6 independent experiments were performed (n=6). X-axis 0=macrophages (no virus).

Consistent with this observation, expression of genes involved in autophagy (Atg5 and LC3B) were not significantly altered (FIG. 44).

HSV1716 Infection Induces an Inflammatory Phenotype in Macrophages

Figure 45:
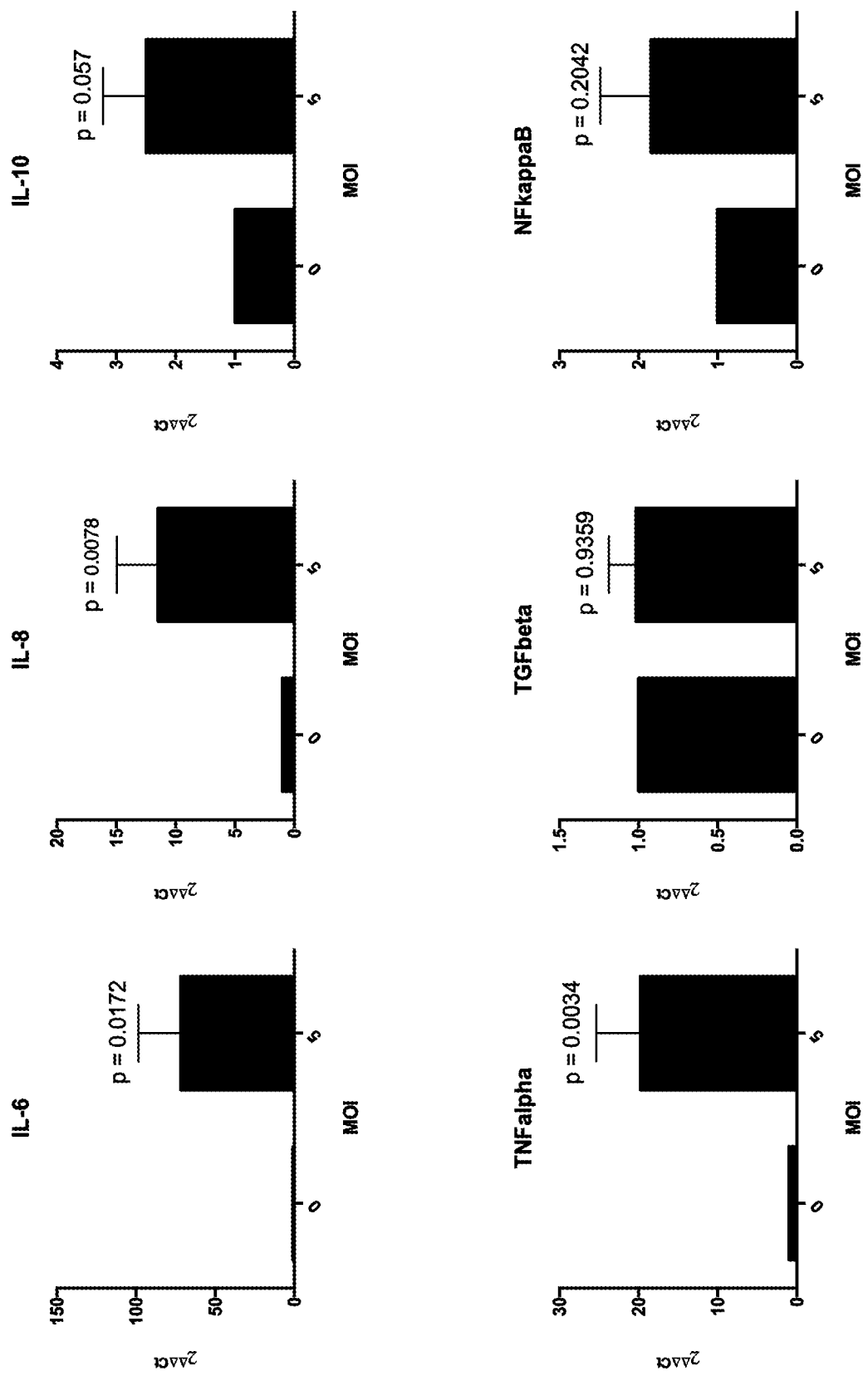
FIG. 45. Charts showing mRNA expression of markers of inflammation in human monocyte-derived macrophages 24 hours post infection. All data were normalised to the house keeping gene GAPDH and 6 independent experiments were performed (n=6). X-axis 0=macrophages (no virus).

HSV1716 infection of day 7 monocyte-derived macrophages significantly induces mRNA expression of typical markers of inflammation 24 hours post infection with significantly increased expression of IL-6, IL-8, TNFalpha. Expression of IL-10, TGFbeta and NFkappaB were not significantly enhanced (FIG. 45).

HSV1716 Infection Induces an Inflammatory Phenotype in Macrophages

Figure 46:
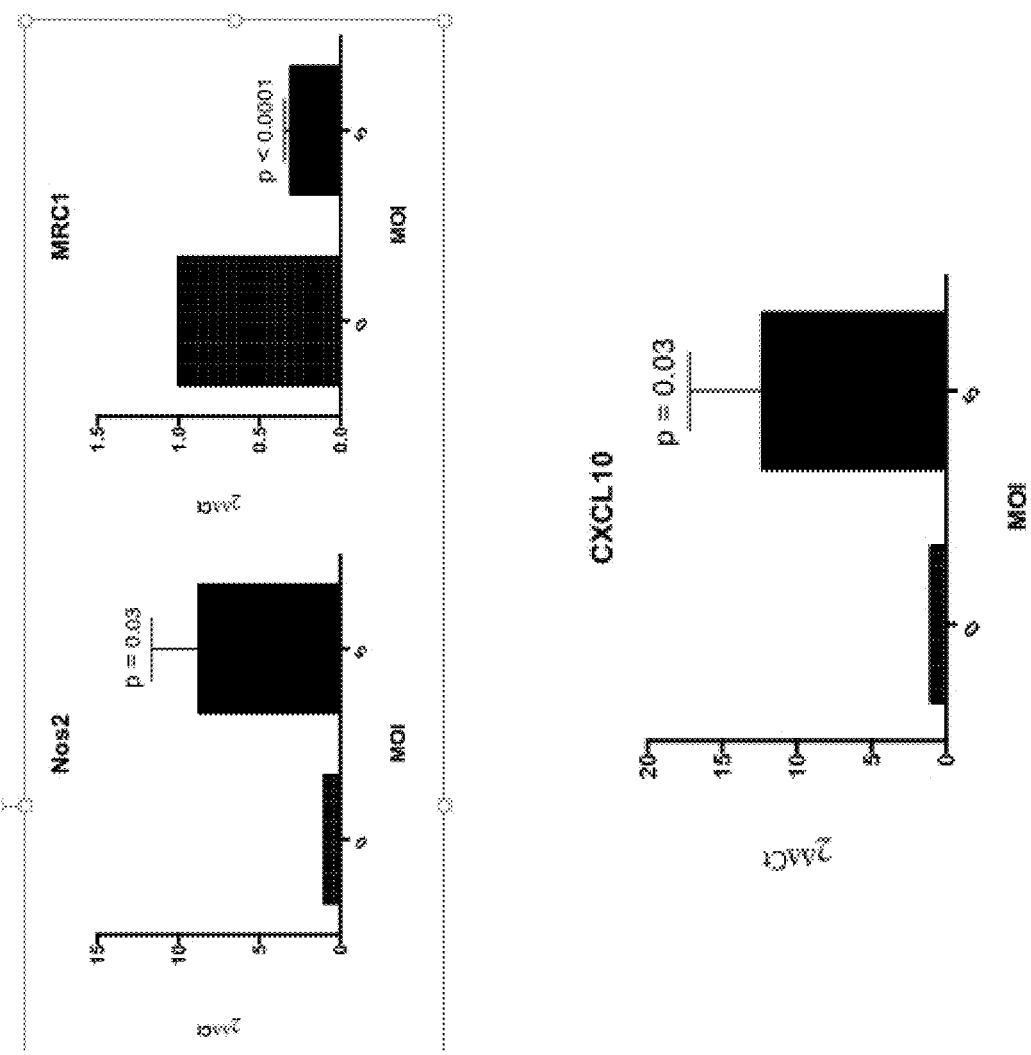
FIG. 46. Charts showing mRNA expression of M1 macrophage markers (NOS2, CXCL10) and M2 macrophage marker (MRC1) in human monocyte-derived macrophages 24 hours post infection. All data were normalised to the house keeping gene GAPDH and 6 independent experiments were performed (n=6).

HSV1716 infection of day 7 monocyte-derived macrophages significantly induces mRNA expression of typical inflammatory M1 macrophage markers (NOS2, and CXCL10) and significantly down regulated expression of the M2 marker MRC1 expressed by tumour-derived macrophages (FIG. 46). There were no significant changes in two other M2 markers, Arg1 and VEGF.

HSV1716 Infection Induces PCNA Expression in Macrophages

Figure 47:
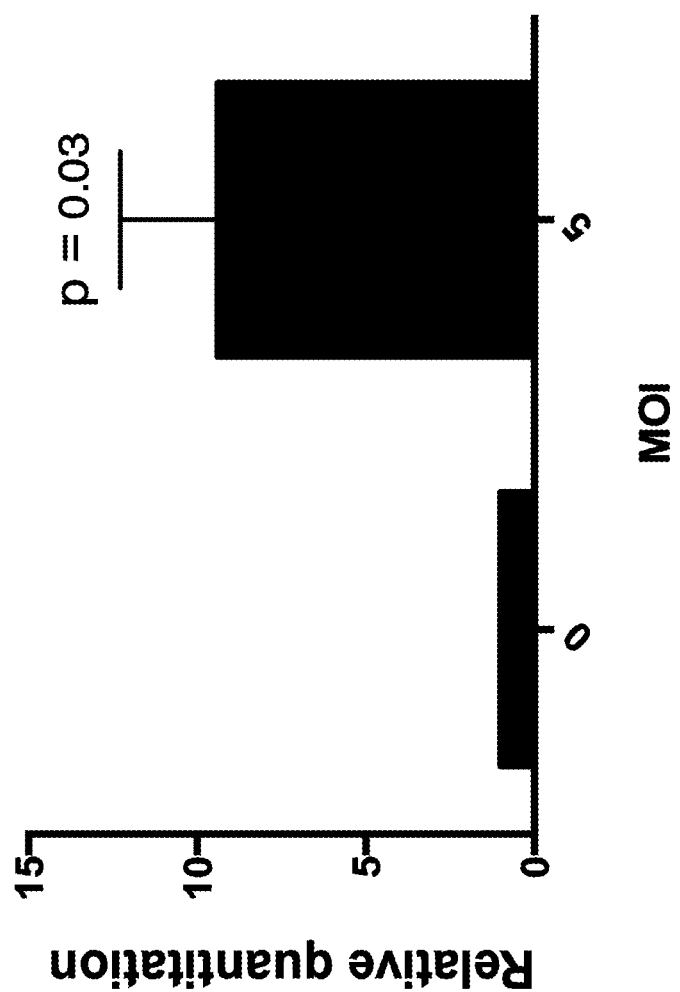
FIG. 47. Chart showing HSV1716 infection of 7 day human monocyte derived macrophages significantly induces PCNA expression. All data were normalised to the house keeping gene GAPDH and 4 independent experiments were performed (n=4).
Figure 48:
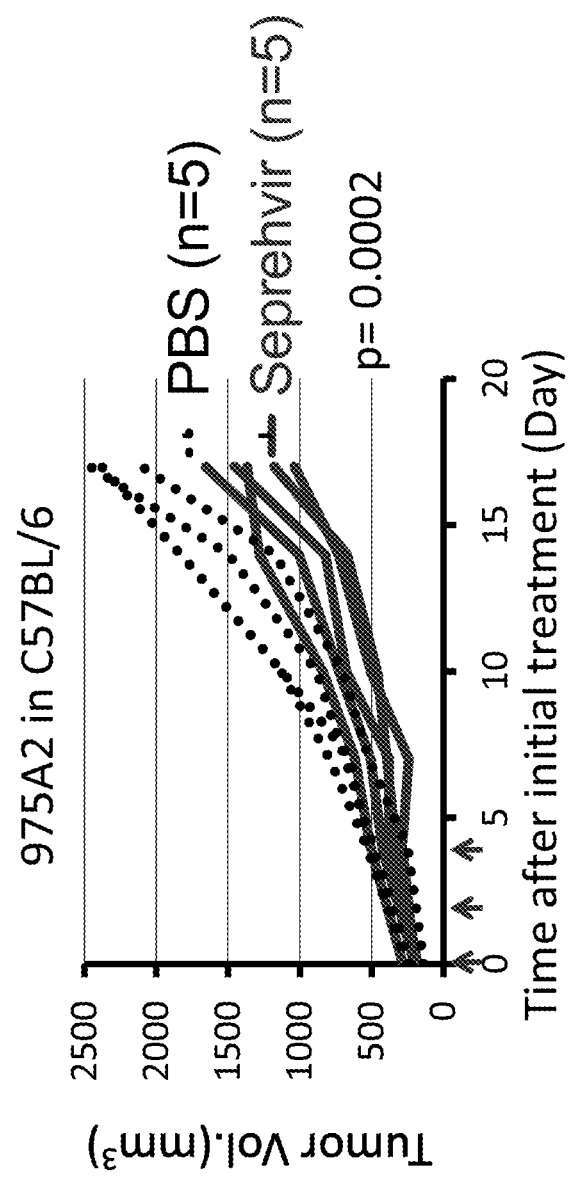
FIG. 48. Chart showing oncolytic HSV therapy significantly delays 975A2 mNB (murine neuroblastoma) tumor growth.
Figure 49:
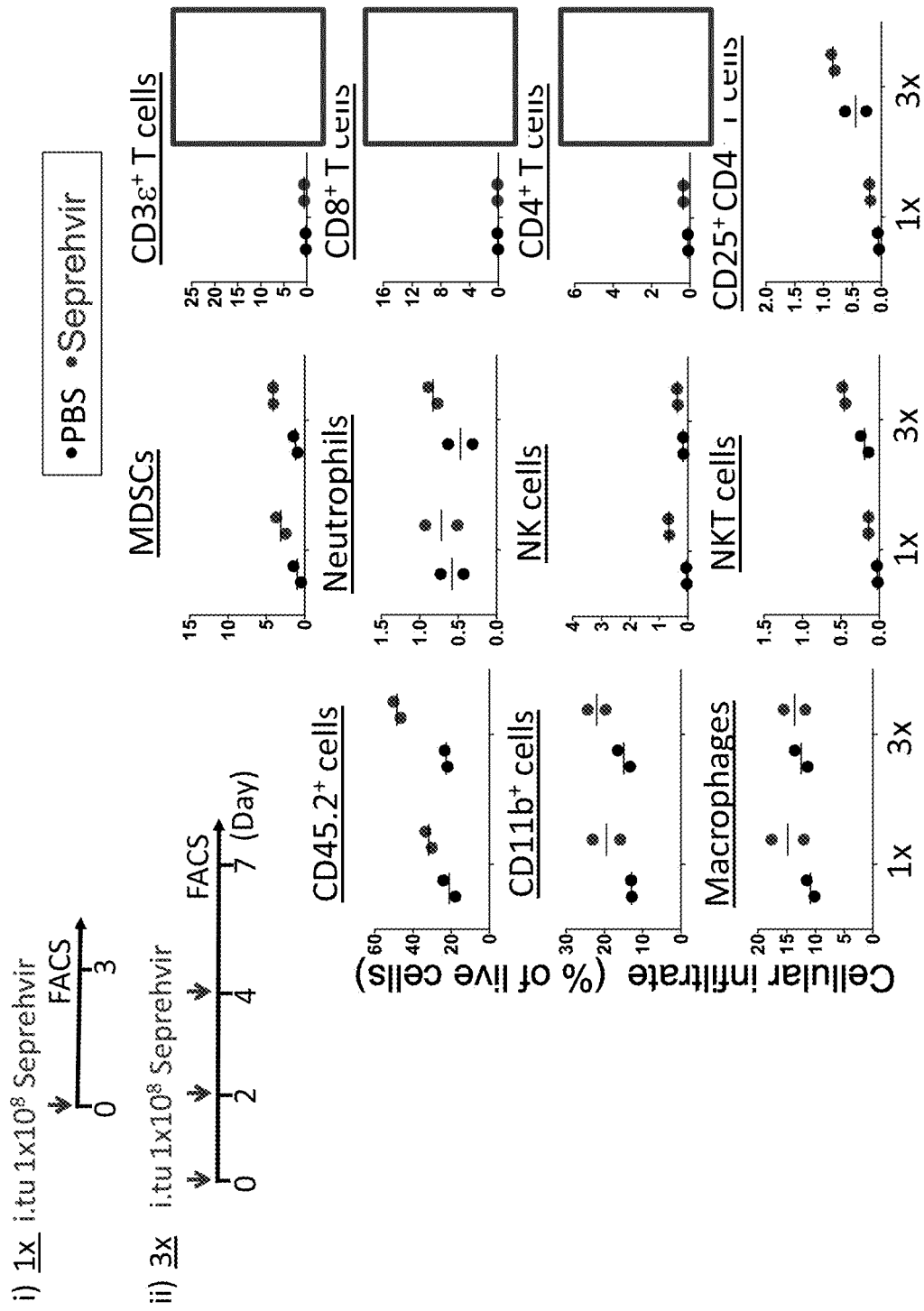
FIG. 49. Oncolytic HSV therapy recruits more T cells in 975A2 mNB tumor. Charts show cellular infiltrate into tumor of different cell types. In all charts pairs of data points are shown for treatment with PBS (left) and Seprehvir (right) for administration of 1 (1×) or 3 (3×) doses.
Figure 50:
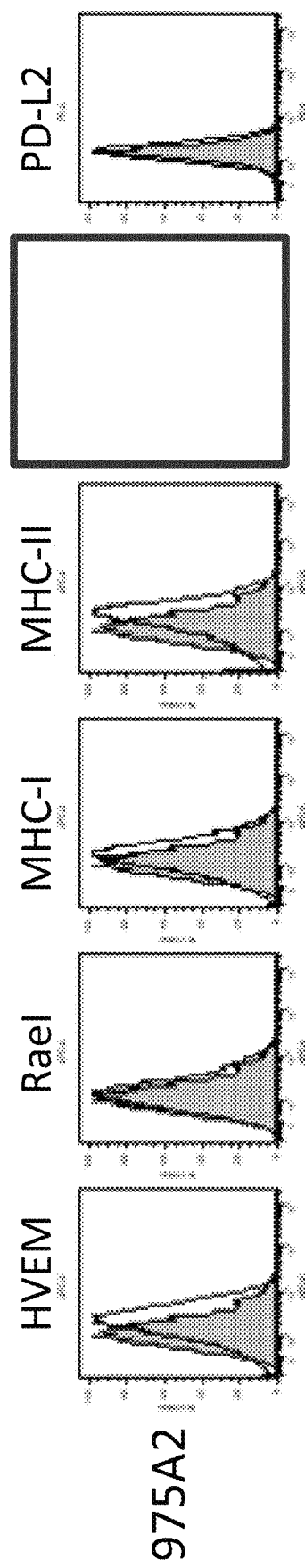
FIG. 50. FACS analysis charts show expression of HVEM, Rael, MHC-I, PD-L1 and PD-L2 on 975A2 mNB cells.
Figure 51:
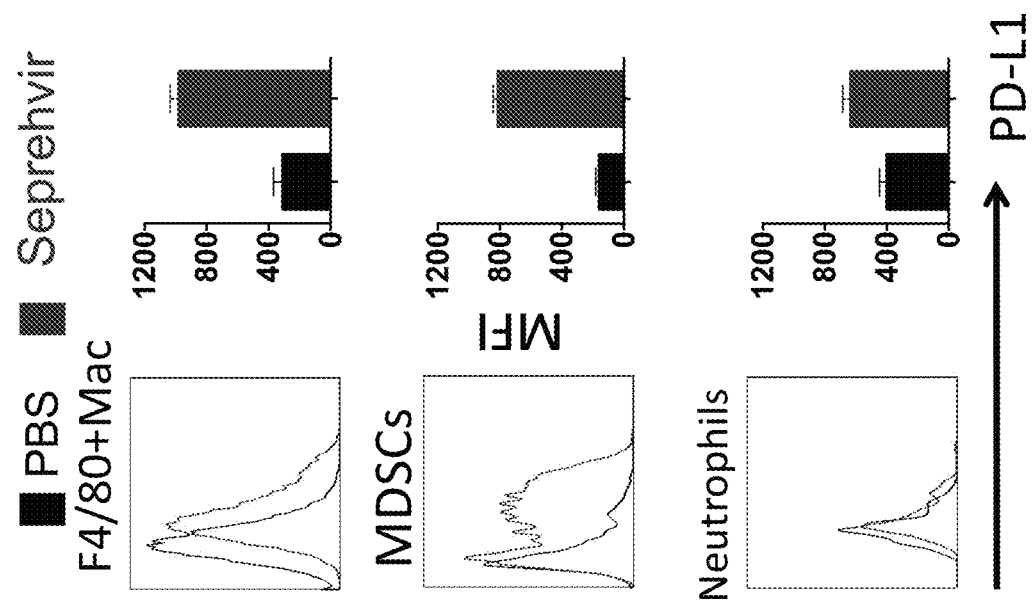
FIG. 51. Oncolytic HSV therapy induces PD-L1 expression in myeloid cells. Charts show PD-L1 expression in F4/80+ Macrophage cells, myeloid derive suppressor cells (MDSCs) and neutrophils. For bar charts, left bar=PBS, right bar=Seprehvir.
Figure 52:
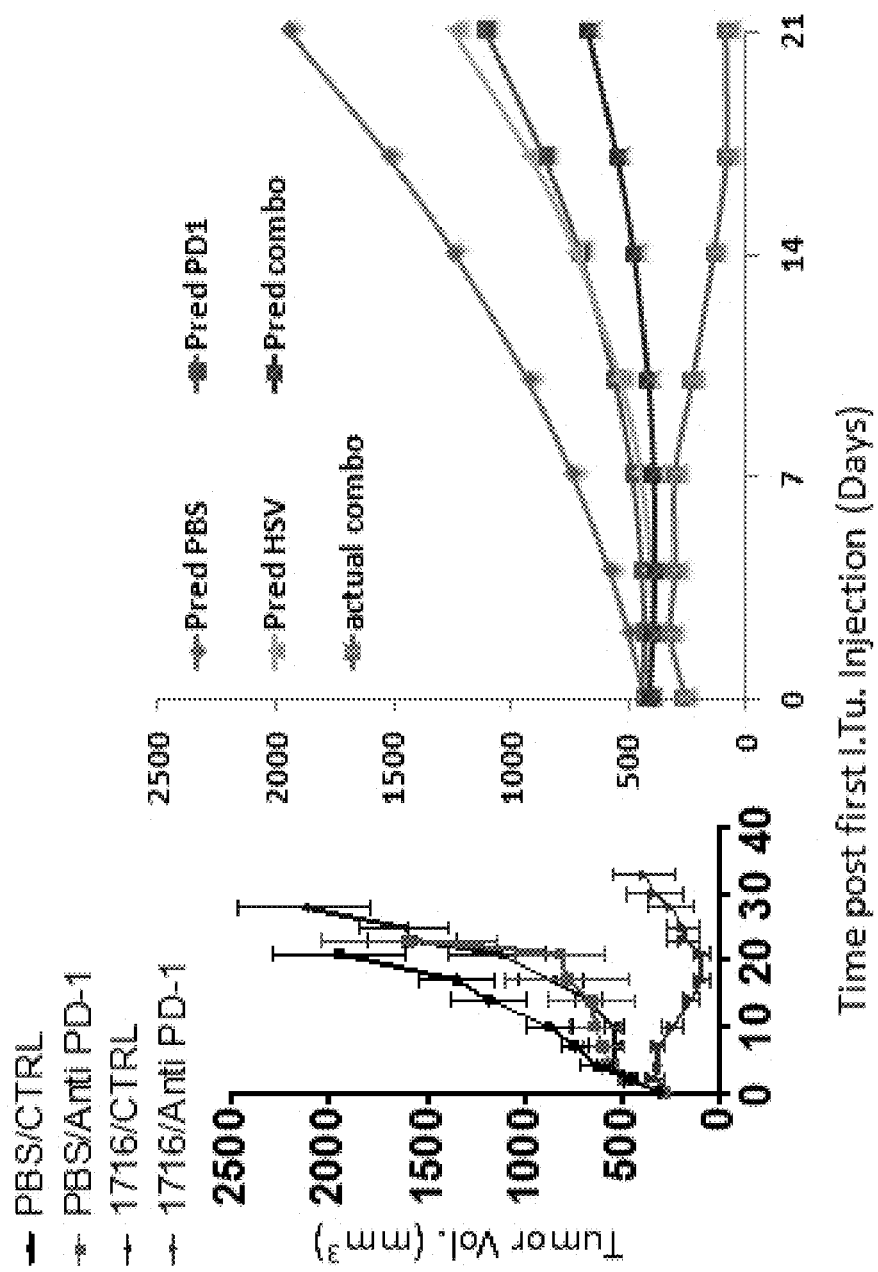
FIG. 52. Charts showing mean tumor volumes from data shown for individual mice in FIG. 29 (left) demonstrates that the combination of Seprehvir+anti-PD-1 is synergistic as the actual combination effect on tumor growth is greater than the predicted additive effect (right).

HSV1716 infection of day 7 monocyte-derived macrophages significantly induces PCNA expression which therefore could be a potential mechanism for inducing viral replication, macrophage cell death and M2 to M1 switching in tumor-dwelling monocytes and other myeloid derived suppressor cells. Further studies are currently being pursued to investigate siRNA knockdown of PCNA prior to HSV1716 infection (FIG. 47).

Taken together, examples 4 and 5 suggest that Seprehvir is capable of inducing Th1 responses leading to anti-tumor immunity by two separate but interdependent mechanisms. Oncolytic replication of cancer cells within the tumor microenvironment induces an inflammatory response which attracts circulating immune cells and initiates a Th1 response. Both tumor-resident and newly recruited immune cells, especially monocytes and other myeloid-derived cells, such as M2 macrophages (TAMs, tumor associated macrophages) are susceptible to Seprehvir infection in this localised inflammatory milieu. Their subsequent infection by Seprehvir progeny released from lytic replication of cancer cells amplifies this Th1 response as for example, macrophages are polarised to the aggressive anti-tumor M1 phenotype. Tumor antigens released by oncolysis and picked up by activated antigen presenting cells leads to the development of anti-tumor immunity.

Example 6—A Phase I Study Investigating the Safety, Tolerability and Efficacy of Intravenous Injections of the Selectively Replication-Competent Herpes Simplex Virus Seprehvir in Patients with Relapsed or Refractory Solid Tumours Summary of Clinical Experience To date ninety eight patients have received Seprehvir, in the context of locally advanced disease, via a variety routes, mostly intra-tumoural (n=83) and the remainder via intra-pleural (n=11) or intravenous (n=4) infusions, in the absence of any definitely attributable Seprehvir-related toxicity.

Forty seven patients with brain tumours have received a range of Seprehvir doses ($10^3$ to $2\times10^6$) intratumorally (n=35) or peri-tumorally post resection (n=12) in 4 clinical studies, three in primary or recurrent glioma and 1 in recurrent glioblastoma multiforme (GBM). No induction of encephalitis or any re-activation of latent wild type HSV was observed and no adverse clinical symptoms attributable to Seprehvir were identified.

Two further clinical studies of Seprehvir have been completed. The first of these, a study in melanoma patients involved five patients with metastatic melanoma and accessible soft tissue tumor nodules. No local or systemic toxicity associated with Seprehvir was observed.

The second of these studies involved 20 patients with resectable squamous cell carcinoma of the head and neck in which patients received a single preoperative intratumoral injection (either 1, 3 or 14 days prior to surgery) with Seprehvir at a dose of $10^5$ i.u. (5 patients) or $5\times10^5$ i.u. (15 patients). No toxicity was experienced by any of the patients and evidence of virus in tumor tissue was observed.

Two clinical studies are currently on-going.

A Phase I/IIa study in Malignant Pleural Mesothelioma is investigating the safety, tolerability and biological effect of single and repeat intra-pleural administration of Seprehvir at a dose of $1\times10^7$ iu. To date, three patients have received a single dose of Seprehvir through their IPC, three have received two doses and five have received four doses with recruitment of an additional one patient required at the four dose level to complete the trial. Seprehvir is well-tolerated with a limited number of transient possibly-related adverse events identified.

In the Phase I dose escalation study in non-CNS tumours, three patients have received a single intratumoral administration of $1\times10^5$ i.u. Seprehvir, two patients have received a single intratumoral administration of $2\times10^6$ i.u. Seprehvir, one patient has received a single intratumoral administration of $2\times10^6$ i.u. Seprehvir on two separate occasions and three patients have received a single intratumoral administration of $1\times10^7$ i.u. Seprehvir to date. The intratumoral arm of this study is now closed to recruitment.

Study Rationale

Seprehvir is an oncolytic virus that replicates in and lyses the dividing cells of tumours but fails to replicate in normal post-mitotic cells. Seprehvir also has anti-cancer vaccination potential with induction of anti-tumour immune responses observed in mesothelioma (MPM) patients Based on this selective replication phenotype and the lack of attributable toxicity noted in preclinical systemic dosing models, coupled with the clinical safety profile demonstrated in 96 patients treated by localised Seprehvir delivery, a study in patients with recurrent/metastatic advanced solid tumours is proposed. The starting dose will be $1\times10^7$ i.u. based on the current loco-regionally administered dose used in our MPM study and supported by a murine biodistribution studies and the maximum dose FDA-approved doses to be used in the systemic arm of the study in non-CNS solid tumours in children and adolescents.

Since it is considered highly relevant to analyse tumour tissue for evidence of Seprehvir replication and cell lysis, pre-tumour biopsies and post treatment biopsy or resection will be conducted for all patients.

Objectives and Endpoints

Primary objective: To evaluate the safety, tolerability and tumour localisation of repeat IV administration of Seprehvir in patients with relapsed or refractory solid tumours Secondary objective: To evaluate the patient's immunological response post-Seprehvir administration Primary endpoint: Safety and tolerability, in terms of the emergence of DLTs, will be assessed by conducting the following safety assessments at pre-defined time-points during the study:

Physical examination, including vital signs
ECG
Analysis of laboratory parameters as follows.
  Haematology: full blood count including differential white cell count, haemoglobin, and haematocrit; coagulation parameters including prothrombin time (PT) and activated partial thromboplastin time (APPT)
  Biochemistry: urea, creatinine, sodium, potassium, total protein, total bilirubin, alanine aminotransferase (ALT), aspartate aminotransferase (AST), γ-glutamyltranspeptidase, lactate dehydrogenase (LDH), alkaline phosphatase, albumin, calcium, phosphorus, glucose, creatine kinase
Viral shedding in urine and buccal swab samples
Evidence of Seprehvir replication will be assessed using plasma/serum samples and tumour tissue by:
  PCR for the detection of Seprehvir genomes
  IHC of Seprehvir antigens in biopsy/resected tissue
Adverse events will be recorded throughout the study period.

Secondary endpoints: The immune response to Seprehvir administration will be assessed by conducting the following at pre-defined time-points during the study:
  Measurement of circulating anti-HSV IgG and IgM in plasma samples
  Analysis of circulating and tumour localised immune cells using immune cell profiling and emergence of anti-tumour immune responses
  Pharmacodynamic assessments in plasma/serum samples and tumour tissue
    Tumour markers (CEA, Ca19-9, Ca15-3, Ca125, LDH, PSA as appropriate)
    Biomarkers of Seprehvir activity to include but not limited to IFNgamma and related Th1 cytokines and chemokines, HMGB1, HSP70 and 90
    Histology and immunohistochemistry for necrosis, apoptosis, immune infiltration Study Design This Phase I study will run at two sites in the UK.

This is a Phase I, open-label, dose-escalation study to evaluate the safety, tolerability and tumour localisation of Seprehvir, a selectively replication-competent herpes simplex virus, administered IV in 36-40 patients with histologically confirmed unresectable advanced or metastatic solid tumours that are refractory to standard therapy.

The study will follow a 3+3 design to explore the safety and tolerability and tumour localisation of up to 8× IV administrations of Seprehvir, at 2 dose levels ($1\times10^7$ iu and $1\times10^8$ iu).

The starting dose will be $1\times10^7$ iu, administered IV on 4 weekly occasions on days 1, 8, 15 and 22. The dose will then escalate to $1\times10^8$ iu and Seprehvir administered IV on 4 weekly occasions on days 1, 8, 15 and 22. Two other dosing regimen will be tested at $1\times10^8$ iu. Patients will receive either a single cycle of 4× IV Seprehvir on days 1, 5, 8 and 13 or two cycles of this dosing scheme one week apart.

The DLT assessment period will comprise the first 12 days after last IV dose. Recruitment into each cohort will be sequential, whereby the first patient to be treated must have successfully completed the DLT assessment period without experiencing a DLT, prior to the next patient being treated at that dose level. The twelve-day dosing interval will be observed for all subsequent patient(s). Initially three patients will be treated in a given cohort. If any of these 3 patients experience a DLT during their DLT assessment period, an additional 3 patients (total of six) will be treated at that dose level. Following completion of the DLT assessment period by the final patient in each cohort, all available adverse event and laboratory safety data will be collated and reviewed by the Principal Investigator and sponsor, and a decision made regarding progression to the next dose level.

Patients who do not complete the DLT assessment period for reasons other than toxicity will be replaced for the purpose of toxicity evaluation.

Dose Limiting Toxicities

The definition of Seprehvir DLT will be made according to the National Cancer Institute (NCI) Common Terminology Criteria for Adverse Events [NCI CTCAE Version 4].

Haematological DLT:
  Neutropenia <$0.5\times10^9$/L for >5 days
  Neutropenia <$1\times10^9$/L with fever
  Thrombocytopenia <$25\times10^9$/L accompanied by bleeding or thrombocytopenia <$10\times10^9$/L Non-Haematological DLT:
  Any Grade 3 or 4 toxicity that is not related to tumour progression with the exception of
    Grade 3 'flu-like symptoms (including fever, chills and malaise) in the absence of appropriate prophylaxis
    Grade 3 nausea, vomiting and abdominal pain unless persisting for >2 days despite appropriate prophylaxis
    Isolated laboratory abnormalities≥Grade 3 that resolve to ≤Grade 1 in ≤7 days without clinical sequelae or need for therapeutic intervention will not be considered a DLT If a patient develops an absolute neutrophil count (ANC) <500/μL or a platelet count<25,000/μL, blood samples must be collected every 2 to 3 days and study treatment withheld until counts resolve or until ANC returns to >1000/μL and platelet counts return to >75,000/μL.

Study Population

Figure 53:
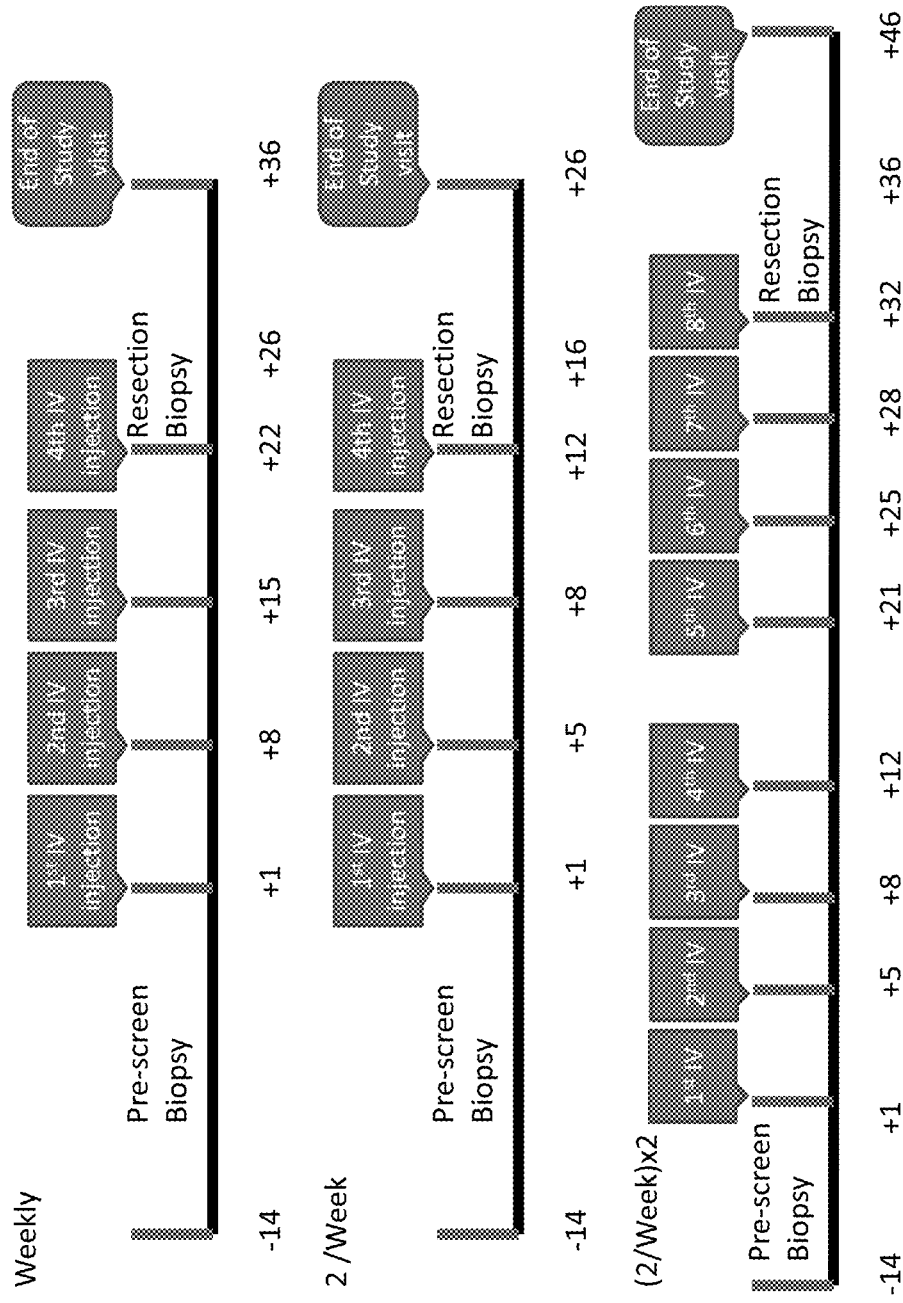
FIG. 53. Diagrammatic illustration of treatment cycles: weekly, and twice weekly (one and two cycles).

Inclusion Criteria:
  1. Patients with histologically confirmed solid tumour who have exhausted all standard lines of therapy for advanced or metastatic disease and/or for whom no standard therapy exists
  2. Previous treatment with anticancer agent(s), including chemotherapy, immunotherapy, biological or hormonal therapy (other than LHRH agonists), must be completed≥4 weeks (6 weeks for nitrosoureas or mitomycin C) prior to administration of Seprehvir, and all associated toxicity must be resolved to ≤grade 1 prior to administration of Seprehvir 3. Previous radiation therapy must be completed ≥14 days prior to administration of Seprehvir, and all associated toxicity must be resolved to ≤Grade 1 prior to administration of Seprehvir
4. Prior major surgery must be completed within 4 weeks prior to Seprehvir administration
5. Age ≥18 years (at screening)
6. ECOG performance status 0 or 1 at screening
7. Life expectancy >12 weeks (at screening) as determined by the Principal Investigator/Sub-Investigator
8. Ability to give written informed consent as evidenced by signature on the patient consent form, to communicate well with the investigator and to comply with the expectations of the study
9. Male and female patients of child-bearing potential must use an approved method of contraception during the study and for 3 months after the last dose of Seprehvir Exclusion Criteria:

A patient will be excluded from the study if any of the following apply:
1. Evidence of severe or uncontrolled systemic disease, congestive cardiac failure> New York Heart Association (NYHA) Class 2, myocardial infarction within 6 months, or any medical or surgical condition that is deemed significant by the Principal Investigator
2. Known hypersensitivity to any Seprehvir excipients
3. Brain metastases that are associated with a changing neurological deficit that has been documented to be stable for <3 months, or for which systemic corticosteroids are required
4. Laboratory values:
   a) ANC ≤1500/μL
   b) Platelet count ≤75,000/μL
   c) Haemoglobin <9 g/dL
   d) Serum bilirubin ≥1.5× upper limit of normal (ULN) unless Gilbert's Disease (≥2×ULN) is known to be the only underlying hepatic disorder
   e) Aspartate aminotransferase (AST) and alanine aminotransferase (ALT) ≥2.5× ULN (AST and ALT ≥5× ULN for subjects with liver metastasis)
   f) Creatinine clearance within the local laboratory normal range
   g) >1+ proteinuria on consecutive testing at least 24 hours apart
5. Prior investigational agents for malignant or non-malignant disease within 4 weeks or 5 half-lives (whichever is shorter) prior to Day 1
6. Previous treatment with viral therapy of any kind within 8 weeks of entry to the study
7. Active systemic bacterial or clinically proven infection with hepatitis B (HBV) or C(HCV) or evidence of Human Immunodeficiency Virus (HIV) infection
8. Pregnancy or lactation
9. History of a second malignancy except those treated with curative intent >3 years previously in the absence of relapse and basal cell skin cancer or cervical cancer in situ Treatment and Interventions Patients will attend clinic study visits at screening and on Days 1, 8, 15 and 22 for IV Seprehvir administration at the first dose level of $1 \times 10^7$ iu (FIG. 53). The dose will then be escalated to $1 \times 10^8$ iu and patients will attend clinic study visits at screening and on Days 1, 8, 15 and 22 for IV Seprehvir administration at this dose (FIG. 53). Two other dosing regimen will be tested at $1 \times 10^8$ iu. Patients will receive either a single cycle of 4× IV Seprehvir on days 1, 5, 8 and 13 or two cycles of this dosing scheme one week apart (FIG. 53). Patients will then undergo biopsy or resection, 4-7 days after the final dose.

Screening Period: Tumour biopsy within 14 days before the first dose of Seprehvir (Day 1).

Treatment Cycle: Days 1 to 22, 1 to 13 or 1 to 32 (FIG. 53).

Duration and Frequency

Seprehvir will be administered on Day 1 of each 4 to 8 dose cycle until development of severe toxicity or withdrawal of consent.

Evaluation

Physical examination, vital signs, ECG, routine blood panel (haematology, clinical chemistry coagulation), HSV immune response (IgG/IgM), urine sample and buccal swab for assessment of viral shedding taken at initiation of baseline assessment, followed by days +1, +8, +15, +22, +36 if weekly injections, days +1, +5, +8, +13, +26 if 2 injections/week or days +1, +5, +8, +13, +21, +25, +28, +32 and +46 if 2×2 injections per week.

HSV bloods (IgG/IgM) and immune cell profiling (FACS) taken at pre-screen, at time of biopsy/surgery, and at end of study visit.

Additional viremia assessment (HSV-1 PCR blood) conducted at 3, 6 and 24 hrs post administration.

Seprehvir replication and immune cell recruitment (HSV-1 PCR and IHC)—tumour tissue samples taken in pre-treatment biopsy and post treatment surgery or biopsy.

Follow up: The End of Study Visit is to occur 14 days after the subject has discontinued study treatment. All Seprehvir-related toxicities will be followed until the End of Study Visit or until all treatment-related toxicities have resolved to ≤Grade 2, stabilized, or returned to baseline.

Example 7—Phase I Trial of HSV1716 in Patients with Non-Central Nervous System (Non-CNS) Solid Tumors Clinical trial NCT00931931 is an investigation into the use of HSV1716 in patients with non-central nervous system (non-CNS) solid tumors (typically sarcomas and neuroblastoma) and has a two part study design. Part 1 of the study specifies a single dose of virus. Participants who experience at least stable disease or relapse following a determination of stable disease, may qualify for subsequent doses in Part 2. There are two treatment arms: an intratumoral route in which participants with localised disease receive HSV1716 as an intratumoral injection; and an intravenous route in which participants with metastatic disease receive HSV1716 intravenously.

FDA approval for systemic administration of Seprehvir in clinical trial was supported by FDA-approved in vivo toxicology & biodistribution studies for IV Seprehvir and extensive preclinical efficacy studies in murine xenograft models.

Participants enrolled in the trial have now started to receive HSV1716. 9 patients are enrolled in the intravenous arm. Intravenous infusion has started at a conservative level with a single dose of $2 \times 10^6$ i.u. HSV1716. Initial results from the first 4 patients demonstrate evidence that HSV1716 is reaching tumor and is replicating therein.

Figure 61:
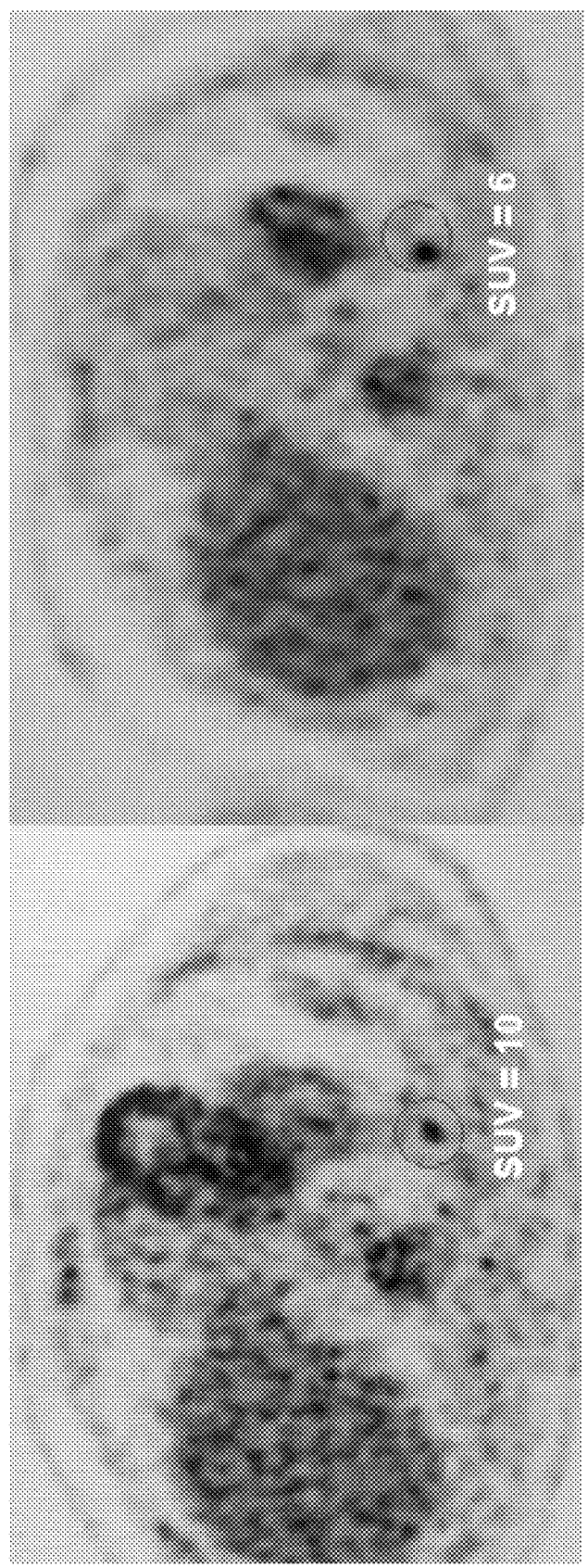
FIG. 61. Digital PET/CT images for patient HSV13 enrolled on NCT00931931 at day 14 and day 28 post intravenous administration of Seprehvir. Transverse image through body. Lesion is circled and SUV indicated.

PCR analysis of blood samples obtained from the patients at several time points was used to identify the presence ("Pos") or absence ("Neg") of HSV-1 DNA. Results are shown in FIGS. 58 and 61 and indicate no evidence of HSV1716 in the circulation immediately following intravenous infusion (day 0 post infusion).

Blood samples were subjected to shell vial culture. All cultures for viable HSV1716 were also negative at all time points However, by Day 4, it is notable that in 2/4 patients a signal reappears in blood samples collected and analysed for HSV DNA by PCR. This signal is consistent with an initial burst of HSV1716 replication in tumor post administration and shedding of HSV1716 DNA back into the circulation. In 1 of 4 patients, the signal persisted to Day 14. This is encouraging given the treatment involved a single dose at low titre. In 1 patient, the signal did not materialise until day 28.

This data shows that herpes simplex virus administered to the blood is immediately absorbed such that intact viral particles are not detectable in the blood. Viral DNA is also not detectable immediately following administration but is detectable several days after administration. This supports the theory that HSV1716 is quickly absorbed by cells or is neutralised following intravenous administration, but is able to reach tumor tissue where it may infect, replicate and lyse cells, lysis of tumor cells releasing viral DNA which is detectable in the blood. Similar PCR results have been seen at Day 4 following image-guided intratumoral administration of HSV1716 in some patients in this study and the similarity in pattern between the PCR bloods by both intratumoral injection and IV infusion is significant.

Pharmacokinetic data from the first two patients treated with intravenous Seprehvir indicates an initial loss of the input signal during the first 24 hrs post IV infusion with subsequent re-emergence of signal at day 4. The fourth IV patient had a positive signal on day 28 (FIG. 59). Supportive of intratumoral replication (intratumoral patients have also shown this pattern of HSV emergence in the circulation).

To date, no virus has been detected in the circulation of third IV patient.

Case Study—Patient HSV13.

This is the fourth patient to receive Seprehvir by intravenous administration. The patient is a 25 year old Caucasian male diagnosed with Ewing's Sarcoma (primary lesion in tibia, metastatic lesion in lung) and enrolled on the study on Apr. 21, 2016. HSV13 received a single dose of $2 \times 10^6$ pfu Seprehvir by intravenous infusion.

PET/CT screening (FIGS. 60 and 61) revealed a low level of standardized uptake value (SUV) at prescreen (no digital PET available), day 14 post Seprehivir administration a flare up (pseudo-progression) was noted with an increased SUV. At day 28 post Seprehivir administration a return to low level SUV was noted. The effect of "pseudo-progression" shortly after treatment is acknowledged for biologic agents.

A similar pattern has been seen in patient HSV06 (receiving intratumoral Seprehvir).

Case Study—Patent HSV07

This patient received Seprehvir by intratumoral administration. Patient is an 8 year old male with a diagnosis of recurrent rhabdomyosarcoma (13 cm Stage III eRMS) in a retroperitoneal location. Prior treatment includes surgery, radiation (41.4 Gy tumor bed/36 Gy LN), chemotherapy (VAC per D9803—remission; Relapse: VI, Cyclo/Topo, IE per ARST0121; PD: Vinorelbine, oral cytox, temsirolimus; PD: Vinorelbine, oral cytox, Avastin). Complications include AKI from obstructive uropathy and ureteral stents, nephrostomies.

Figure 62:
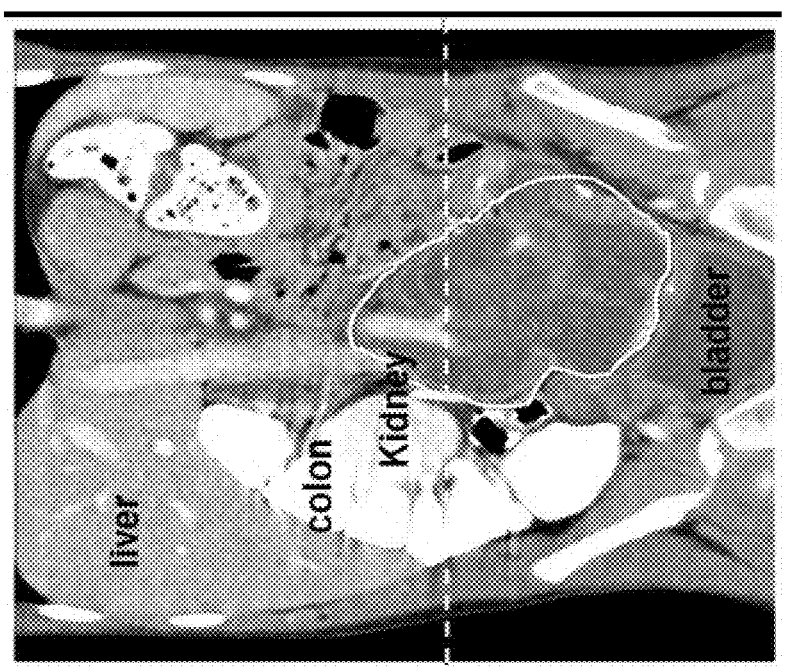
FIG. 62. Digital PET/CT image for patient HSV07 enrolled on NCT00931931 showing regions of tumor.
Figure 63:
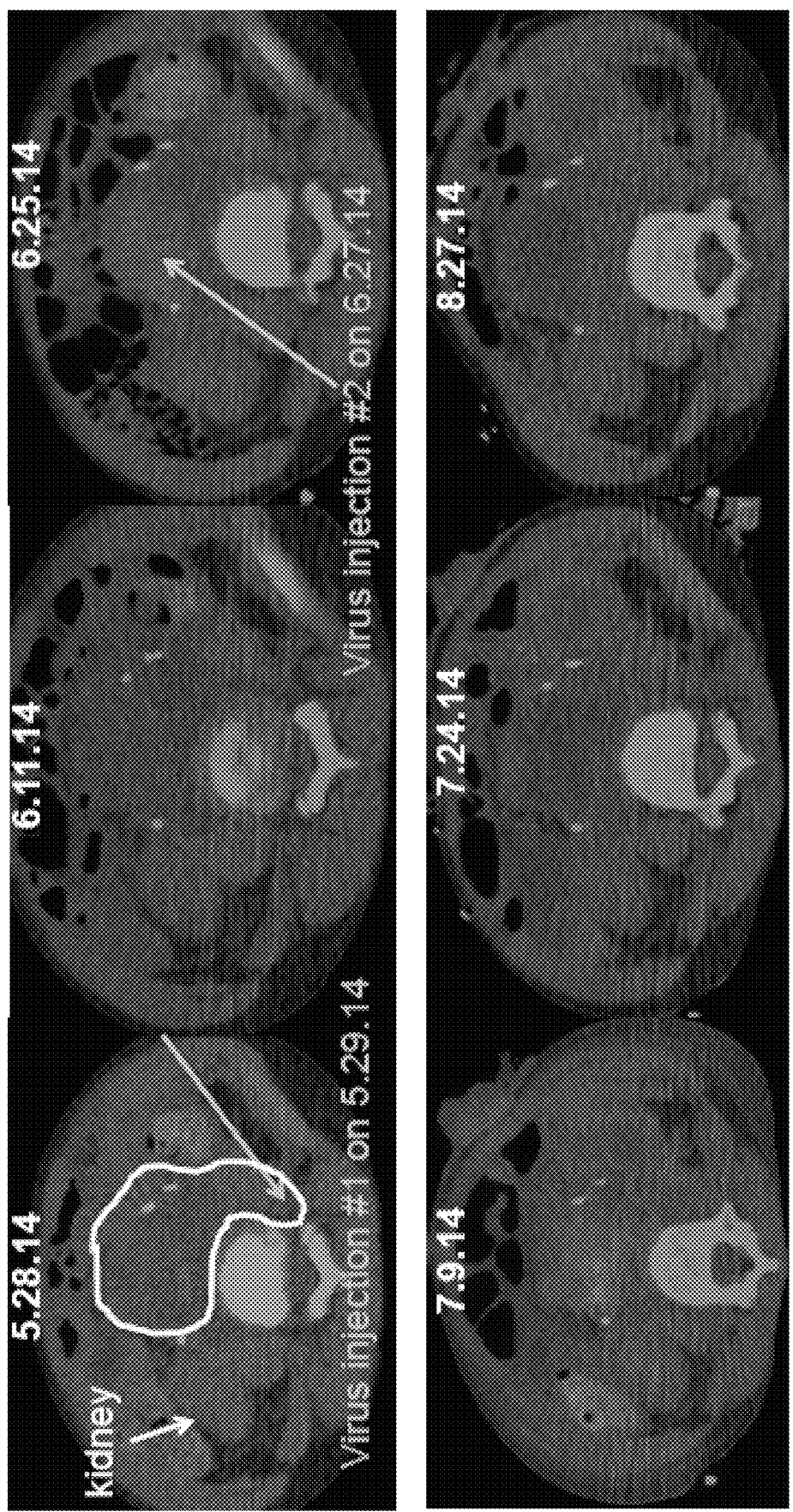
FIG. 63. Digital PET/CT images for patient HSV07 enrolled on NCT00931931 prior to intratumoral administration of Seprehvir (top left), at day 14 post intratumoral administration of Seprehvir (top middle) two days prior to second intratumoral injection of virus on Jun. 27, 2014 (top right) and post second intratumoral injection (bottom row).

HSV07 showed interesting PET/CT findings (FIGS. 62 and 63). A pre-injection PET on 28 May 2014 identified a site in tumour mass for injection. PET scan day 14 post $1^{st}$ injection indicated stable disease at injection site—$2^{nd}$ injection administered. PET hot spot at site distant from $1^{st}$ injection on day 28. Hot spot chosen as site for $2^{nd}$ injection on 27 Jun. 2014. PET hot spot gone on 24 Jul. 2014.

DISCUSSION

HSV is being detected in patients receiving a single intravenous low dose ($2 \times 10^6$ pfu) of Seprehvir. This is a low dose, similar to doses normally used in experiments with mice. Experiments in mice typically use a dose of $1 \times 10^6$ or greater, meaning that following scale up for human administration (considering human mass and blood volume) the expected dose required would be about $1 \times 10^9$ pfu or higher. Such a dose would provide new challenges to (i) prove the safety of such a high dose and (ii) manufacture sufficient quantities of virus. The finding that an effect is present at a dose as low as $1 \times 10^6$ pfu means that intravenous administration of doses in the range $1 \times 10^7$ to $1 \times 10^8$ represents a viable approach to treatment of tumors in human patients. Results from our study of patients having mesothelioma (Example 1) are also consistent with multiple systemic doses of Seprehvir leading to a sustained Th1 response.

No HSV is being detected immediately following administration of virus but, surprisingly, an HSV signal is re-emerging in 3 out of 4 patients after at least several days. The re-emergence of signal is consistent with results seen in patients receiving intra-tumoral administration of Seprehvir by image guided technology (compare IV and ITu arms in FIG. 59).

The levels of HSV DNA detected by quantitative PCR are approximately equivalent to the administered dose, which is a clear indicator that virus is replicating. Our experiments on the stability of Seprehvir in human blood (Examples 11 to 13) show that Seprehvir has a short half-life in human blood. Our observation is therefore consistent with sufficient virus reaching the tumor and replicating therein.

Our intravenous infusion protocol has been well tolerated, with no adverse reactions so far.

These observations are significant. Contrary to the established view (e.g. see Russell et al., (Oncolytic virotherapy. Nature Biotechnology Vol. 30 No. 7 Jul. 2012) and Seymour and Fisher (British Journal of Cancer (2016) 114, 357-361)), the data emerging from this trial indicates that Seprehvir can successfully circumvent the innate obstacles presented by human blood and the human immune system, can replicate and expand the viral population to therapeutically effective levels and reach tumor tissue. This opens the door to an alternative treatment of tumors that are difficult to access by intratumoral injection.

Description of NCT00931931

Official Title:

A Phase I Dose Escalation Study of Intratumoral or Intravenous Herpes Simplex Virus-1 Mutant HSV1716 in Patients with Refractory Non-Central Nervous System (Non-CNS) Solid Tumors.

Purpose

Patients with relapsed solid tumors such as sarcomas and neuroblastoma have a poor survival, generally <20%. There is an urgent need for new treatments that are safe and effective.

HSV1716, an oncolytic virus, is a mutant herpes simplex virus (HSV) type I, deleted in the RL1 gene which encodes the protein ICP34.5, a specific determinant of virulence. Mutants lacking the RL1 gene are capable of replication in actively dividing cells but not in terminally differentiated cells—a phenotype exploited to selectively kill tumor cells. In previous clinical studies, HSV1716 has been shown to be safe when injected at doses up to $10^5$ plaque forming units (pfu) directly into human high-grade glioma and into normal brain adjacent to tumour, following excision of high-grade glioma. In an extension study, HSV1716 has been shown to be safe when injected at a dose of up to $10^6$ pfu directly into brain tumours.

Replication of HSV1716 in human glioblastoma in situ has been demonstrated. Following a single administration of HSV1716 by direct injection into active recurrent tumor or brain adjacent to tumor, some patients have lived longer than might have been expected. In part, this study seeks to evaluate the safety of a single injection of HSV1716 in the treatment of extracranial solid tumors in adolescents and young adults.

HSV1716 has also proved safe when given by direct intra-tumoural injection in patients with squamous carcinoma of the head and neck, and in patients with malignant melanoma.

Replication of HSV mutants in human sarcomas and neuroblastoma in cultured cells and human xenograft models has been demonstrated. This study is designed in two parts. PART 1 of the study specifies a single dose of virus. Participants who experience at least stable disease or relapse following a determination of stable disease, may qualify for subsequent doses in PART 2. PART 2 requires signing of a separate consent.

Primary Outcome Measures:

To determine whether intratumoral injection or intravenous infusions of HSV1716 is safe in adolescents and young adults with non-CNS solid tumors.

Secondary Outcome Measures:

To measure antiviral immune response in patients with refractory cancer treated with HSV1716.

Treatment Arms

Intratumoral route—participants with localized disease receive HSV1716 as an intratumoral injection.

Intravenous route—participants with metastatic disease receive HSV1716 intravenously.

Condition

Participants may have one of the following conditions: Rhabdomyosarcoma, Osteosarcoma, Ewing Sarcoma, Soft Tissue Sarcoma, Neuroblastoma, Wilms Tumor, Malignant Peripheral Nerve Sheath Tumor, Clival Chordoma, Non-CNS Solid Tumors.

Eligibility

Ages Eligible for Study: 7 Years to 30 Years
Genders Eligible for Study: Both
Accepts Healthy Volunteers: No Inclusion Criteria:

Inclusion of Women and Minorities: The study is open to all participants regardless of gender or ethnicity.

Inclusion for intratumoral injection: Subject must have 1-3 lesions amenable to HSV1716 administration by needle if superficial; by needle and/or catheter if deep or pulmonary, via interventional radiology without undue risk. Lesion(s) must meet specific size criteria.

Inclusion for intravenous administration: Subject must have metastatic disease or a lesion not deemed suitable for direct injection.

Age: Subjects must be greater than or equal to 7 years and less than or equal to 30 years of age at the time of signing consent (study entry).

Histologic Diagnosis: Subjects must have had histologic verification of a non-CNS solid tumor at original diagnosis. The tumor must be amenable to HSV1716 administration without undue risk. Disease must be considered refractory to conventional therapy or for which no conventional therapy exists.

Metastatic Disease: Subjects who have metastasis to the brain are eligible for the intratumoral arm of this study; however, no metastatic sites within the brain will be considered for injection. Subjects who have metastasis to the brain are eligible for the intravenous arm of this study only if those metastases have been treated and are no longer active.

Performance Level: Karnofsky greater than or equal to 50. Subjects who are unable to walk because of paralysis, but who are up in a wheelchair will be considered ambulatory for the purpose of assessing the performance score.

Subjects must have fully recovered from the acute toxic effects of all prior chemotherapy, immunotherapy, or radiotherapy prior to entering this study;

Myelosuppressive chemotherapy: Must not have received within 28 days of entry onto this study (42 days if prior nitrosourea) accompanied by hematopoietic recovery, or 14 days of stopping non-myelosuppressive therapy as long as hematopoietic requirements are met;

Biologic (anti-neoplastic agent): Must not have received within 7 days of entry onto this study (21 days if prior VEGF-Trap and at least 3 half lives after last dose of a monoclonal antibody). For biologic agents that have known adverse events occurring beyond 7 days after administration, this period must be extended beyond the time during which adverse events are known to occur;

No Radiation Therapy greater than or equal to 14 days for local palliative XRT (small port): greater than or equal to 6 months must have elapsed if prior craniospinal XRT or if greater than or equal to 50% radiation of pelvis; greater than or equal to 42 days must have elapsed if other substantial bone marrow radiation;

Immunoablative or myeloablative Stem Cell Transplant (SCT): greater than or equal to 6 months must have elapsed from prior autologous transplant. Subjects must not have graft versus host disease post autologous transplant;

Investigational agent: greater than or equal to 28 days must have elapsed from treatment with a different phase I agent;

Subjects with seizure disorder may be enrolled if on anticonvulsants and well controlled. At the time of enrollment, specified CNS conditions must be less than or equal to Grade II toxicity per CTCAE 3.0 criteria;

All subjects must have adequate blood counts defined as: peripheral absolute neutrophil count (ANC) greater than or equal to 750/uL, Platelet count greater than or equal to 100,000/uL (may be a post transfusion value), Hemoglobin greater than or equal to 9.0 gm/dL (may be a post transfusion value)

Adequate renal function defined as: Serum creatinine less than or equal to 1.5× upper limit of normal (ULN) for age or creatinine clearance or radioisotope GFR greater than or equal to 70 ml/min/1.73 m2;

Adequate liver function defined as: Total bilirubin less than or equal to 2.0×ULN for age, and SGPT (ALT) less than or equal to 2.5×ULN for age and albumin greater than or equal to 2 g/dL, GGT<2.5×ULN Adequate cardiac function as defined by: Shortening fraction>25% by echocardiogram or ejection fraction above the institutional lower limit of normal by MUGA, No focal wall motion abnormalities as determined by either of the above studies, EKG without evidence of ischemia or significant arrhythmia Adequate coagulation as defined by: PT/INR and PTT<1.5×ULN for age;

Infectious Disease: Documented evidence of negative tests for the presence of Hepatitis B surface antigen, Hepatitis C antibody, HIV1 and HIV2 antibodies within the three months preceding study entry. Subjects who do not have such evidence must undergo appropriate testing prior to virus administration;

Exclusion Criteria:

Stem cell transplant: No subjects who have received an allogeneic hematopoietic stem cell transplant are eligible;

Pregnancy or Breast-Feeding: There is no available information regarding human fetal or teratogenic toxicities. Pregnant women are excluded and pregnancy tests must be obtained in girls who are post-menarchal. Males or females of reproductive potential may not participate unless they have agreed to use an effective contraceptive method from the time of study entry to a period of no less than four months post the final HSV1716 injection. For the same period of time, women who participate in this study must agree not to breast feed;

Consent: Unable or unwilling to give voluntary informed consent/assent;

Leukemia: Subjects with leukemia are not eligible for study participation;

Infection or any other severe systemic disease or medical or surgical condition deemed significant by the principal investigator;

Administration of any unlicensed or investigational agent within 4 weeks of entry to the study;

Growth factor(s): No PEG-GCSF within 14 days of virus injection (day 0);

Anti-HSV antivirals: Subjects whose physicians determine that anti-HSV antiviral therapy (such as acyclovir, ganciclovir, foscarnet, etc.) cannot be safely discontinued from 2 days prior to the injection to 28 days following the injection should not be in the study.

Subjects who have other conditions which in the opinion of the investigator contra-indicate the receipt of HSV1716 or indicate subject's inability to follow protocol requirements.

Example 8—a Phase Ib/2 Open-Label Evaluation of the Safety and Efficacy of Intravenous Administration of Oncolytic Herpes Simplex Virus HSV1716 and Pembrolizumab Compared to Pembrolizumab Alone and HSV1716 Alone in Subjects with Stage III or Stage IV Head and Neck Cancer In the Phase Ib part of this study, the objective of the study is to demonstrate tumor targeting of HSV1716 when administered by intravenous administration in patients with any operable head and neck cancer who are indicated to receive a tumor resection. Each patient will receive up to 4 doses of HSV1716 by intravenous infusion at two dose levels ($1\times10^7$ i.u. and $1\times10^8$ i.u.). Each dose will be administered within 1 to 7 days of the previous dose. The final dose will be administered within 1 to 14 days of the tumor resection. Patient tumor material will be collected during the procedure and will be stored for analysis to confirm evidence of HSV1716 localisation to tumor and anti-tumor immunological or biological effect. Analysis will involve shell vial culture, immunohistochemical analysis of tumor tissue, qPCR to detect HSV DNA, and detection of immunological response, e.g. infiltrating immune cells, cytokine response.

In addition, the safety and tolerability of the two dose levels will be carefully monitored and compared during the period up to tumor resection to confirm the maximum tolerated dose (MTD) for the Phase II part of the Study. 3 patients will be recruited to each dose level but in the event of a single Dose Limiting Toxicity at any dose level, the cohort will be expanded to 6 patients according to the usual "3+3" dose-escalation design.

In the Phase 2 part of this study, the objectives of this study are to evaluate the following measures in an open-label, multi-center, controlled study. Approximately 180 patients are to be recruited and randomized 1:1:1 across each of the 3 treatment arms:

Arm 1: pembrolizumab alone;
Arm 2: HSV1716 alone;
Arm 3: HSV1716 and pembrolizumab.

Pembrolizumab (also known as MK-3475; lambrolizumab, Keytruda™; Merck, USA) is a humanised antibody that binds PD-1.

Primary Outcome Measures:
Progression-free Survival (PFS) per immune related response criteria ("irRC") for All Participants
Overall Survival (OS) for All Participants Secondary Outcome Measures:
PFS per irRC in Participants with PD-L1-Positive Expression
OS in Participants with PD-L1-Positive Expression
Objective Response Rate (ORR) per irRC in All Participants
ORR per irRC in Participants with PD-L1-Positive Expression
Time to Tumor Progression (TTP) per irRC in All Participants
TTP per irRC in Participants with PD-L1-Positive Expression
Percentage of Participants Experiencing Grade 3-5 AEs
Time to First Grade 3-5 Adverse Event (AE)
Percentage of Participants Experiencing Viral Shedding of HSV1716
Percentage of Participants Experiencing an Anti-viral immune response to HSV1716

In Arm 1, pembrolizumab is administered intravenously at a dose of 200 mg on day 1 of each 3 week cycle.

In Arms 2 and 3, HSV1716 is administered by intravenous infusion at a dose of up to $1\times10^8$ i.u. on each occasion or at the dose of HSV1716 established as the MTD in the Phase 1b part of the study. For intravenous infusion of HSV1716, vials of HSV1716 will be diluted into 250 mL lactated Ringer's solution and administered over one hour. Virus will be infused via peripheral IV access. Standard hospital contact and respiratory precautions will be followed, per institutional standards of operations for this type of product. The dosing schedule for HSV1716 commences on day 1 and continues every week thereafter until up to 8 doses have been administered (i.e. Days 1, 8, 15, 22, 29, 36, 43 and 50).

In Arm 3, pembrolizumab at a dose of 200 mg and HSV1716 at up to $1\times10^8$ i.u. are administered according to the following schedule. The treatment may occur on the same day. Where a delay in commencement of pembrolizumab is clinically justified, 1 cycle of HSV1716 may be given prior to commencement of pembrolizumab.

|  | Day | | | | | | | |
|---|---|---|---|---|---|---|---|---|
| Agent | 1 | 8 | 15 | 22 | 29 | 36 | 43 | 50 |
| HSV1716 | + | + | + | + | + | + | + | + |
| Pembrolizumab |  | + |  |  | + |  |  | + |

In Arms 1 and 3, subjects shall continue dosing with pembrolizumab therapy until a predetermined number of doses is reached, dose limiting toxicity is observed or disease progression is observed.

Times specified above are all subject to a tolerance of +/−3 days.

Results may be stratified by stage of disease, PD-L-1 status of tumor, treatment cycles and anti-viral immune response.

Subjects are treated in each arm of the study until the first to occur of: complete response; disease progression as per the irRC; or intolerance of study treatment.

For intravenous infusion of HSV1716, vials of HSV1716 will be diluted into 250 mL lactated Ringer's and administered over one hour. Virus will be infused via peripheral IV access. Standard hospital contact and respiratory precautions will be followed, per institutional standards of operations for this type of product.

Example 9—Method for Selecting Patients for Treatment with a Combination of HSV1716 and Pembrolizumab Patients with head and neck cancer who are indicated for surgery may receive up to 4 doses of HSV1716 by intravenous infusion prior to surgical resection. Tumor tissue from the resection may be analysed for evidence of HSV1716 targeting the tumor and for an immunological or biological activity in response to oncolytic immunotherapy. Patients demonstrating such activity may be selected for cycles of HSV1716 therapy following surgery with the aim of targeting residual tumor cells at the site of surgical resection and/or metastatic disease.

Example 10—Preparation of a Vial of HSV1716 for Intravenous Infusion

The total virus dose for each patient will be diluted into 250 mL lactated Ringer's and administered over one hour according to the following instructions. Virus will be infused via peripheral IV access. Standard hospital contact and respiratory precautions will be followed, per institutional standards of operations for this type of product.

Frozen vials of HSV1716 will be dispensed from the Pharmacy. Preparation for intravenous administration will be performed within an appropriate 'clean' room. If transport to a 'clean' room is required, vials will be placed into a secondary container, labeled appropriately and transported on dry ice. The label will include "Route of administration—intravenous".

A 250 mL bag of lactated Ringer's solution for intravenous infusion will also be dispensed from the Pharmacy and transported as needed to the 'clean' room in preparation for intravenous administration. The lactated Ringer's solution to be maintained at room temperature.

Defrost the vials of HSV1716 according to the manufacturer's instructions. Once the vials are defrosted, they must be used immediately.

Place the re-suspended vials and the bag containing 250 mL of lactated Ringer's solution (IV bag) in a biosafety cabinet to prepare the HSV1716 final drug product for intravenous administration, Aspirate 1 mL of the virus suspension from each vial into a syringe ready for injection into the 250 mL bag of lactated Ringer's via the inlet port. Gently mix the contents of the IV bag using a backwards and forwards rocking motion.

Immediately following dilution of the investigational product in the 250 ml of lactated Ringer's solution, label the IV bag containing the HSV1716 final investigational drug product for intravenous administration according to institutional policies and applicable state and federal regulations. Immediately transfer to the Principal Investigator or other staff as appropriate for use.

Intravenous administration must be completed within a three hour time period following preparation of the HSV1716 final drug product.

Following the preparation of HSV1716 for intravenous use, immediately place used vials on ice and return to the study biosafety team for appropriate research purposes or deactivation.

The invention claimed is:

1. A pharmaceutical composition comprising an oncolytic herpes simplex virus and an immune checkpoint inhibitor, wherein the oncolytic herpes simplex virus does not contain a functional $\gamma_1 34.5$ gene, encodes a functional ICP47 gene, and does not express GMCSF, wherein the oncolytic herpes simplex virus is a mutant of HSV-1 strain 17, and wherein the immune checkpoint inhibitor is an antibody or small molecule inhibitor of PD-1 or PD-L1.

2. The pharmaceutical composition of claim 1, wherein the oncolytic herpes simplex virus is HSV1716.

3. A kit comprising a predetermined amount of oncolytic herpes simplex virus and a predetermined amount of an immune checkpoint inhibitor, wherein the oncolytic herpes simplex virus does not contain a functional $\gamma_1 34.5$ gene, encodes a functional ICP47 gene, and does not express GMCSF, wherein the oncolytic herpes simplex virus is a mutant of HSV-1 strain 17, and wherein the immune checkpoint inhibitor is an antibody or small molecule inhibitor of PD-1 or PD-L1.

4. A kit according to claim 3, wherein the oncolytic herpes simplex virus is HSV1716.

5. A product containing therapeutically effective amounts of (i) an oncolytic herpes simplex virus, and (ii) an immune checkpoint inhibitor, wherein the oncolytic herpes simplex virus does not contain a functional $\gamma_1 34.5$ gene, encodes a functional ICP47 gene and does not express GMCSF, wherein the oncolytic herpes simplex virus is a mutant of HSV-1 strain 17, and wherein the immune checkpoint inhibitor is an antibody or small molecule inhibitor of PD-1 or PD-L1.

6. The product according to claim 5, wherein the oncolytic herpes simplex virus is HSV1716.

7. A method of treating a PD-L1 expressing cancer in a subject, the method comprising simultaneous or sequential administration of oncolytic herpes simplex virus and an immune checkpoint inhibitor, wherein the oncolytic herpes simplex virus is a mutant of HSV-1 strain 17 and the oncolytic herpes simplex virus does not contain a functional $\gamma_1 34.5$ gene, encodes a functional ICP47 gene, and does not express GMCSF, and wherein the immune checkpoint inhibitor is an antibody or small molecule inhibitor of PD-1 or PD-L1.

8. The method according to claim 7, wherein the oncolytic herpes simplex virus is HSV1716.

9. The method according to claim 7, wherein the method comprises administering one or more doses of the oncolytic herpes simplex virus effective to induce a Th1 immune response.

10. The method of claim 7, wherein the method further comprises determining the presence of a Th1 immune response in the subject.

* * * * *